(12) United States Patent
Norikane

(10) Patent No.: US 9,126,899 B2
(45) Date of Patent: Sep. 8, 2015

(54) PHOTOSENSITIVE AZOBENZENE DERIVATIVE

(71) Applicant: NATIONAL INSTITUTE OF ADVANCED INDUSTRIAL SCIENCE AND TECHNOLOGY, Tokyo (JP)

(72) Inventor: Yasuo Norikane, Ibaraki (JP)

(73) Assignee: NATIONAL INSTITUTE OF ADVANCED INDUSTRIAL SCIENCE AND TECHNOLOGY, Tokyo (JP)

(*) Notice: Subject to any disclaimer, the term of this patent is extended or adjusted under 35 U.S.C. 154(b) by 0 days.

(21) Appl. No.: 14/361,599

(22) PCT Filed: Nov. 30, 2012

(86) PCT No.: PCT/JP2012/081215
§ 371 (c)(1),
(2) Date: May 29, 2014

(87) PCT Pub. No.: WO2013/081155
PCT Pub. Date: Jun. 6, 2013

(65) Prior Publication Data
US 2014/0323704 A1 Oct. 30, 2014

(30) Foreign Application Priority Data
Dec. 1, 2011 (JP) ................. 2011-263292

(51) Int. Cl.
C07C 245/08 (2006.01)
C09K 9/02 (2006.01)
C09J 201/00 (2006.01)
C09J 11/06 (2006.01)
C08K 5/23 (2006.01)

(52) U.S. Cl.
CPC ............. *C07C 245/08* (2013.01); *C09J 11/06* (2013.01); *C09J 201/00* (2013.01); *C09K 9/02* (2013.01); *C08K 5/23* (2013.01); *C09K 2211/1007* (2013.01); *C09K 2211/1014* (2013.01)

(58) Field of Classification Search
CPC .................................................. C07C 245/08
USPC ...................................................... 534/843
See application file for complete search history.

(56) References Cited

U.S. PATENT DOCUMENTS 6,740,255 B2 5/2004 Kato

FOREIGN PATENT DOCUMENTS

JP 2000-328051 A 11/2000
JP 2003-238962 A 8/2003

WO 2011/142124 A1 11/2011

OTHER PUBLICATIONS

Tamura et al., "Synthesis and Photochemistry of Stillbene Ionic Liquids", Chem. Lett., 2010, 39, p. 240-241.
Norikane et al., "Photoinduced isothermal phase transitions of liquid-crystalline macrocyclic azobenzenesw", Chem. Commun., 2011, 47, p. 1770-1772.
Norikane et al., "Unconventional thermodynamically stable cis isomer and trans to cis thermal isomerization in reversibly photoresponsive [0.0](3,30)-azobenzenophane", Chem. Commun., 2008, p. 1898-1900.
Norikane et al., "Photochemical and Thermal cis/trans Isomerization of Cyclic and Noncyclic Azobenzene Dimers: Effect of a Cyclic Structure on Isomerization", J. Org. Chem., 2006, p. 1296-1302.
Nagamani et al., "Photoinduced Hinge-Like Molecular Motion: Studies on Xanthene-Based Cyclic Azobenzene Dimers", J.Org. Chem. 2005, 70, p. 9304-9313.
Norikane et al., "Light-Driven Molecular Hinge: A New Molecular Machine Showing a Light-Intensity-Dependent Photoresponse that Utilizes the Trans-Cis Isomerization of Azobenzene", Org. Lett., 2004, vol. 6, No. 15, p. 2595-2598.
Norikane et al., "Novel Crystal Structure, Cis-Trans Isomerization, and Host Property of Meta-Substituted Macrocyclic Azobenzenes with the Shortest Linkers", J. Org. Chem., 2003, vol. 68, No. 22, p. 8291-8304.
Norikane et al., "Azobenzenophane: NovelCrystal Structure and Cis-TransIsomerization of Distorted Azobenzene", Org. Lett., 2002, vol. 4, No. 22, p. 3907-3910.
Kobatake et al., "Photochromism of 1,2-Bis(2,5-dimethyl-3-thienyl)perfluorocyclopentene in a Single Crystalline Phase", J. Am. Chem. Soc. 1999, 121, 2380-2386.
Kunihiro Ichimura, "Reversible photoisomerisability and particle size changes of mill-dispersed azobenzene crystals in water", Chem. Commun., 2009, 1496-1498.

(Continued)

*Primary Examiner* — Robert Havlin
(74) *Attorney, Agent, or Firm* — Greenblum & Bernstein, P.L.C.

(57) ABSTRACT

The present invention addresses the problem of providing with a simple production process and with high efficiency a new photosensitive azobenzene derivative which is capable of freely controlling phase transition by photostimulation, and the problem is solved by using an azobenzene derivative represented by general formula (1). (1) (In the formula, $R_1$ and $R_6$ are independently an alkoxyl group having 6-18 carbon atoms, $R_2$-$R_5$ and $R_7$-$R_{10}$ are independently a hydrogen atom or an alkyl group having 1-4 carbon atoms which may have branches, provided that not all of $R_2$-$R_5$ and $R_7$-$R_{10}$ are hydrogen).

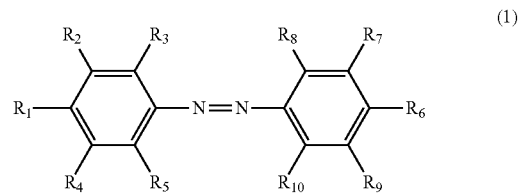

(1)

12 Claims, 15 Drawing Sheets

(56) References Cited

OTHER PUBLICATIONS

Kitagawa et al., "Control of Surface Wettability and Photomicropatterning with a Polymorphic Diarylethene Crystal upon Photoirradiation", Chem. Eur. J. 2011, 17, p. 9825-9831.

Koshima et al., "Mechanical Motion of Azobenzene Crystals upon Photoirradiation", J. Am. Chem. Soc. 2009, 131, p. 6890-6891.

Ikeda et al., "Optical Switching and Image Storage by Means od Azobenzene Liquid-Crystal Films", Science, vol. 268, Jun. 30, 1995, p. 1873-1875.

Grim et al., "Molecular organization of azobenzene derivatives at the liquid/graphite interface observed with scanning tunneling microscopy", J.Vac. Sci. Technol. B, vol. 15, No. 4, Jul./Aug. 1997, p. 1419-1424.

International search report from PCT/JP2012/081215, mail date is Feb. 12, 2013.

(a)

(b)

(c)

(d)

(a)

(b)

(c)

(d)

(a)

(b)

(c)

(d)

PHOTOSENSITIVE AZOBENZENE DERIVATIVE

TECHNICAL FIELD

The present invention relates to a photosensitive azobenzene derivative. More specifically, the present invention relates to a photosensitive azobenzene derivative capable of controlling phase transition in an adjustable manner by light exposure.

BACKGROUND ART

A photoprocessing technique that utilizes a photosensitive material has played an important role in industry. The greatest advantage of such a photoprocessing technique is that a fine pattern can be quickly formed in a contactless manner. For example, a photosensitive material that changes in solubility or the like by light exposure (photoresist) is used for plate making in the field of printing or for microfabrication in the field of electronics, wherein a printing pattern or a circuit pattern is formed by the presence or absence of light exposure.

However, since an existing material normally utilizes an irreversible photoreaction (polymerization or decomposition), it is difficult in principle to restore the material to its original state after light exposure. Actually, the material has been disposed of after use. Therefore, development of a photosensitive material that can be used repeatedly has been one of the most important subjects for green innovation that implements energy conservation and resource saving.

A photoisomerization reaction has been known as a reversible (repeatable) photoreaction, and azobenzenes have been known as typical compounds that can undergo a photoisomerization reaction. The molecule of azobenzenes changes from the trans-configuration to the cis-configuration (isomer) by exposure to ultraviolet light, and restores to the trans-configuration by exposure to blue light or by placement in a dark place. In principle, this reaction (photoisomerization reaction) can repeatedly occur any number of times.

However, it has been known that the reaction easily occurs in a solution state, but rarely occurs in solid (both in pure substance and in mixture). The reason is considered that a free volume is insufficient in solid where molecules are densely packed. The term "solid" used herein refers to both amorphous solid and crystalline solid.

In recent years, deformation of crystals along with photoisomerization (Non-patent Document 1) and photoisomerization of microcrystals (Non-patent Document 2) have been reported as rare examples of photoisomerization of azobenzenes in crystals. However, a change from a solid state to a liquid state due to photoisomerization has not been reported. Non-patent Document 3 and Non-patent Document 4 propose diarylethenes as compounds that undergo a reversible photoreaction in crystals. However, it has not been reported that this molecular system undergoes solid-liquid phase transition.

In view of the above situation, it has been desired to develop a technique that improves the photoreactivity of azobenzenes in solid and that dramatically changes the properties (solid/liquid) of azobenzenes, in order to apply the photoisomerization reaction of azobenzenes to a solid photosensitive material.

Regarding compounds in which a plurality of azobenzenes are bonded to form a ring (macrocyclic azobenzenes), Non-patent Documents 5 to 10 suggest that the compounds differ in photoreactivity from normal azobenzenes due to a special environmental field caused by the ring structure and that the shape of the molecule (i.e., the shape of the ring) changes from a planar shape to a significantly distorted shape along with a photoisomerization reaction.

The inventor of the present invention found and reported a photo-induced melting phenomenon in crystals of compounds which have a long-chain alkoxy group that is radially introduced into the cyclic skeleton of a dimer or a trimer of macrocyclic azobenzenes (Patent Document 1 and Non-patent Document 11). Specifically, the inventor found a phenomenon in which the compounds (azobenzene derivatives) change into liquid by exposure of solid (crystals) to light and the produced liquid restores to solid when heated. The azobenzene derivatives are characterized in that they can repeatedly undergo phase transition between a solid state and a liquid state any number of times.

Non-patent Document 12 suggests stilbene derivatives as compounds that change from liquid into solid due to a photoisomerization reaction. However, the stilbene derivatives do not change from solid to liquid by exposure to light.

RELATED-ART DOCUMENT

Non-Patent Document

Non-patent Document 1: H. Koshima, N. Ojima, H. Uchimoto, J. Am. Chem. Soc., 131, 6890 (2009)
Non-patent Document 2: K. Ichimura, Chem. Commun., 1496 (2009)
Non-patent Document 3: K. Kitagawa, I. Yamashita, S. Kobatake, Chem. Eur. J. 17, 9825 (2011)
Non-patent Document 4: S. Kobatake, T. Yamada, K. Uchida, N. Kato, M. Irie, J. Am. Chem. Soc. 121, 2380 (1999)
Non-patent Document 5: Y. Norikane, K. Kitamoto, N. Tamaoki, Org. Lett., 4, 3907 (2002)
Non-patent Document 6: Y. Norikane, K. Kitamoto, N. Tamaoki, J. Org. Chem., 68, 8291 (2003)
Non-patent Document 7: Y. Norikane, N. Tamaoki, Org. Lett., 6, 2595 (2004)
Non-patent Document 8: S. A. Nagamani, Y. Norikane, N. Tamaoki, J. Org. Chem., 70, 9304 (2005)
Non-patent Document 9: Y. Norikane, N. Tamaoki, Eur. J. Org. Chem., 1296 (2006)
Non-patent Document 10: Y. Norikane, R. Katoh, N. Tamaoki, Chem. Commun., 1898 (2008)
Non-patent Document 11: Y. Norikane, Y. Hirai, M. Yoshida, Chem. Commun., 47, 1770 (2011)
Non-patent Document 12: H. Tamura, Y. Shinohara, T. Arai, Chem. Lett., 39, 240 (2010)

Patent Document

Patent Document 1: WO 2011/142124

SUMMARY OF THE INVENTION

Technical Problem

Since a material that changes from solid into liquid by exposure to light has not been known, the azobenzene derivatives disclosed in Patent Document 1 have not only academic significance but also expectation of application to an industrial material of a new concept. A known photosensitive material has been disposed of after use. The azobenzene derivatives which undergo photo-induced melting have expectation not only of wide-ranged application as an alternative to known photosensitive materials but also of application as an adhesive material that can be affixed and removed by exposure to light, for example.

However, the azobenzene derivatives disclosed in Patent Document 1 have problems in that the synthesis is difficult and in that the yield of cyclic compounds is about 1%, and thus the production efficiency is insufficient. The azobenzene derivatives disclosed in Patent Document 1 have another problem in that they change into liquid by exposure to light and need application of heat to restore to solid.

The present invention was conceived in order to solve the above problems. An object of the present invention is to provide novel photosensitive azobenzene derivatives which can be efficiently produced by a simple production process and undergo phase transition that can be arbitrarily controlled by photostimulation. Another object of the present invention is to provide novel photosensitive azobenzene derivatives which change from solid (crystals) into liquid by exposure to ultraviolet light; reversibly restore to solid by exposure to visible light; and can repeatedly undergo phase transition between solid and liquid any number of times. Another object of the present invention is to provide novel photosensitive azobenzene derivatives which can be used in various fields (e.g., printing field, electronics field, display field, optoelectronics field, and photonics field).

Solution to Problem

The inventor of the present invention conducted research on photosensitive azobenzene derivatives that undergo phase transition from solid to liquid by light exposure. Unlike the past, the inventor focused on linear azobenzenes in the molecular design instead of cyclic azobenzenes. As a result of further extensive studies, the inventor found that, by introducing an appropriate substituent into the benzene ring site of the azobenzene molecule, packing in a crystal state can be controlled and that a free volume required for photoisomerization can be provided, and finally completed the present invention.

According to the present invention, the following inventions are provided.

(1) An azobenzene derivative represented by the general formula (1),

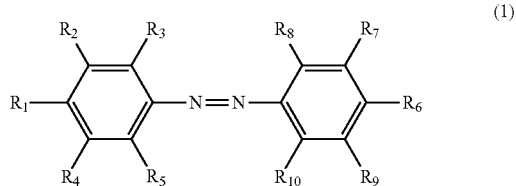

(1)

wherein $R_1$ and $R_6$ are independently an alkoxy group with 6 to 18 carbon atoms, and $R_2$ to $R_5$ and $R_7$ to $R_{10}$ are independently a hydrogen atom or an optionally branched alkyl group with 1 to 4 carbon atoms, with the proviso that the case where all of $R_2$ to $R_5$ and $R_7$ to $R_{10}$ are hydrogen atoms is excluded.
(2) The photosensitive azobenzene derivative according to (1), wherein at least one of $R_2$, $R_4$, $R_7$, and $R_9$ is an optionally branched alkyl group with 1 to 4 carbon atoms.
(3) The photosensitive azobenzene derivative according to (1) or (2), the photosensitive azobenzene derivative being capable of undergoing phase transition between a solid phase and a liquid phase by light exposure.

(4) The azobenzene derivative according to (3), the azobenzene derivative undergoing phase transition from a solid phase to a liquid phase by exposure to ultraviolet light with a wavelength of 300 to 400 nm.
(5) The azobenzene derivative according to (4), the azobenzene derivative undergoing reversible phase transition to the solid phase by exposure of the liquid phase to visible light with a wavelength of 400 to 700 nm.
(6) An optical device comprising the azobenzene derivative according to any one of (3) to (5).
(7) A display device comprising the azobenzene derivative according to any one of (3) to (5).
(8) A recording device comprising the azobenzene derivative according to any one of (3) to (5).
(9) A pattern-forming material comprising the azobenzene derivative according to any one of (3) to (5).
(10) The photosensitive azobenzene derivative according to (1) or (2), the photosensitive azobenzene derivative changing in adhesion by light exposure.
(11) The azobenzene derivative according to (9), wherein an adhesion thereof decreases by exposure to ultraviolet light with a wavelength of 300 to 400 nm and is restored by exposure to visible light with a wavelength of 400 to 700 nm.
(12) An adhesive comprising the azobenzene derivative according to (10) or (11).

Advantageous Effects of the Invention

The present invention provides novel photosensitive azobenzene derivatives which can be efficiently produced by a simple production process and which undergo phase transition that can be arbitrarily controlled by photostimulation. The photosensitive azobenzene derivatives according to the present invention change into liquid by exposure of solid (crystals) to ultraviolet light, reversibly restores to solid by exposure of liquid to visible light, and can repeatedly undergo phase transition between solid and liquid any number of times. Accordingly, the present invention contributes to energy conservation and resource saving.

The photosensitive azobenzene derivatives according to the present invention may be used in the form of a thin film, a photoresist material, an optical device, an adhesive, or a pressure-sensitive adhesive, and may be used in various fields such as printing field, electronics field, display field, optoelectronics field, photonics field, and the like.

DESCRIPTION OF EMBODIMENTS

Figure 1:
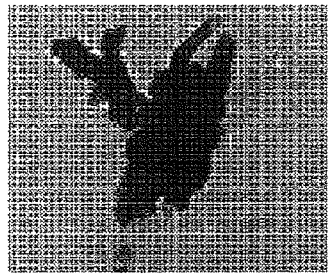
FIG. 1 represents an optical micrograph showing the crystal-isotropic phase transition of Compound A1B1-C12 at 40° C.
Figure 1:
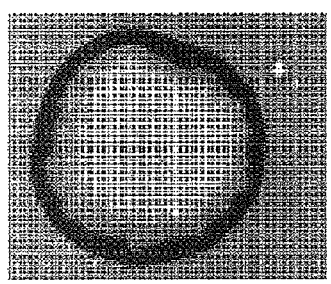
Figure 1:
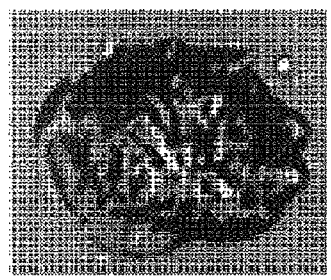
Figure 1:
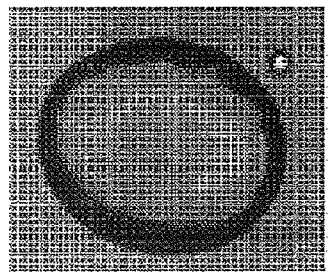

The photosensitive azobenzene derivatives according to the present invention are represented by the following general formula (1).

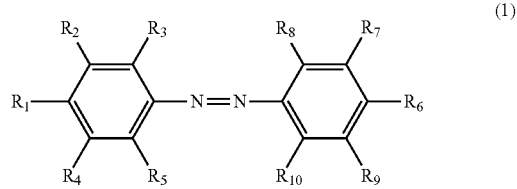

(1)

wherein $R_1$ and $R_6$ are independently an alkoxy group with 6 to 18 carbon atoms, and $R_2$ to $R_5$ and $R_7$ to $R_{10}$ are independently a hydrogen atom or an optionally branched alkyl group with 1 to 4 carbon atoms, with the proviso that the case where all of $R_2$ to $R_5$ and $R_7$ to $R_{10}$ are hydrogen atoms is excluded.

According to the present invention, packing in a crystal state can be controlled and a free volume required for photoisomerization can be provided, by introducing an alkoxy group with 6 to 18 carbon atoms to $R_1$ and $R_6$ of the benzene rings of the azobenzene molecule and by introducing an optionally branched alkyl group with 1 to 4 carbon atoms to as at least one of $R_2$ to $R_5$ and $R_7$ to $R_{10}$. This makes it possible to obtain novel photosensitive azobenzene derivatives capable of arbitrarily controlling their phase transition by photostimulation.

The above compounds can undergo photo-induced phase transition, and the temperature, where the photo-induced phase transition occurs, differs depending on each compound. In order to achieve photo-induced phase transition at room temperature, it is preferable to introduce an optionally branched alkyl group with 1 to 4 carbon atoms to at least one of $R_2$, $R_4$, $R_7$, and $R_9$ (i.e., the positions adjacent to the alkoxy group).

As to the photosensitive azobenzene derivatives according to the present invention, it is preferable to undergo phase transition from a crystal phase to a liquid phase by exposure to ultraviolet light or visible light.

The photosensitive azobenzene derivatives according to the present invention change from solid (crystals) into liquid by exposure to ultraviolet light or visible light, reversibly restore to a solid by exposure of the liquid to visible light, and can repeatedly undergo phase transition between solid and liquid any number of times. This contributes to energy conservation and resource saving.

A material according to the present invention is a thin film, a photoresist material, an optical device, an adhesive, or a pressure-sensitive adhesive which utilizes the photosensitive azobenzene derivatives, and can be used in various fields (e.g., printing field, electronics field, display field, optoelectronics field, and photonics field).

Preferred embodiments of the photosensitive azobenzene derivatives according to the present invention are shown below, however, the present invention is not limited by such typical embodiments.

A1BX series: one of the benzene rings is not substituted with an additional substituent A1B1-C12
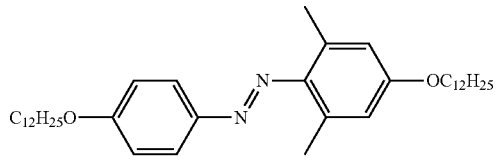

A1B2-C12
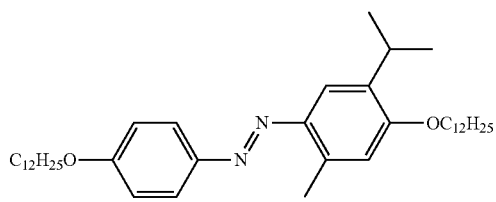

A1B3-C12
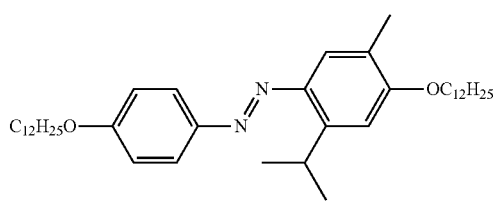

A1B4-C12
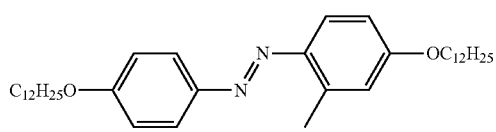

A1B5-C12
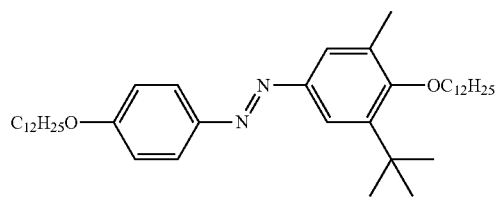

A1B6-C12
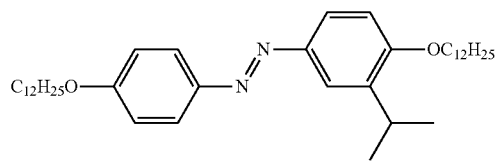

A1B7-C12
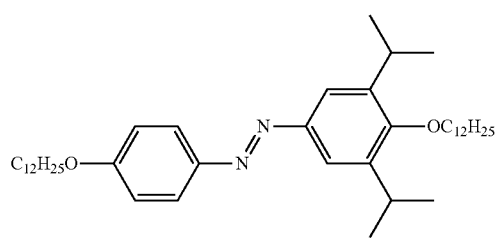

A1B8-C12
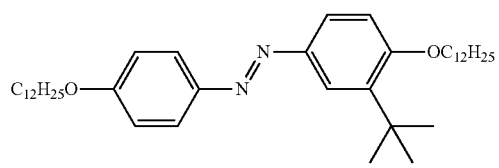

A1B9-C12
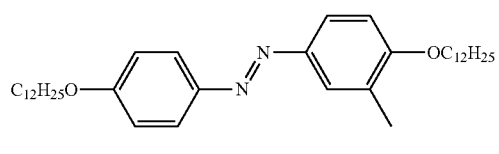

A1B9-C6
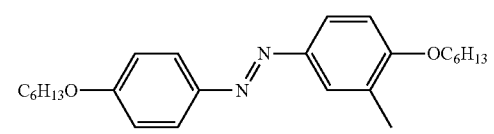

A1B9-C18
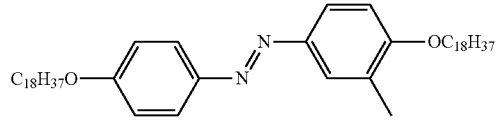

A3BX series: one of the benzene rings is substituted with a methyl group at a position adjacent to the azo bonding A3B1-C12
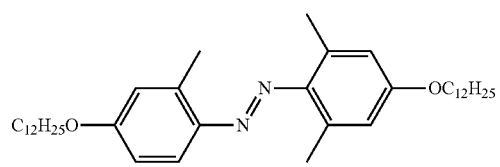

A3B2-C12

A3B3-C12

A3B4-C12
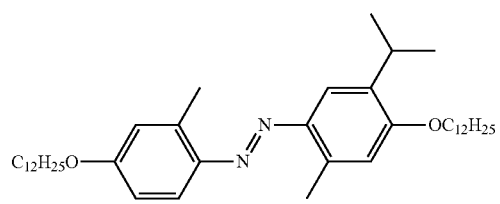

A3B5-C12
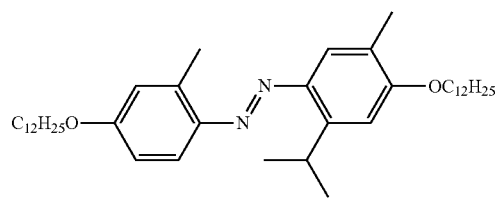

A4BX series: one of the benzene rings is substituted with a methyl group at a position adjacent to the alkoxy group A4B1-C12
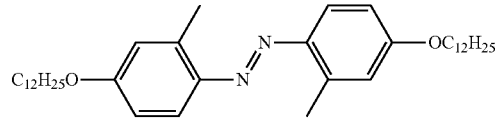

A4B2-C12
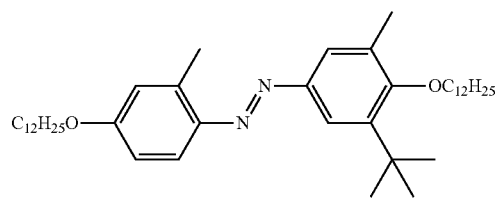

A4B3-C12

A4B4-C12

A4B5-C12

A4B6-C12

A4B7-C12
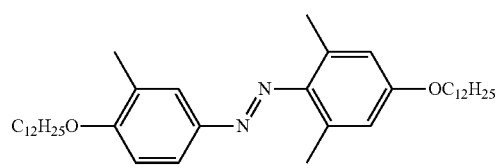

A4B8-C12

A4B9-C12
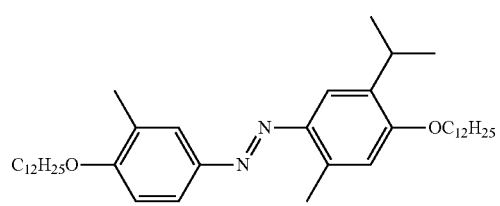

The photosensitive azobenzene derivatives represented by the general formula (1) may generally be synthesized by reductively dimerizing nitro compounds (precursor). The photosensitive azobenzene derivatives represented by the general formula (1) may also be synthesized by oxidatively dimerizing amino compounds (precursor). The photosensitive azobenzene derivatives represented by the general formula (1) may also be synthesized by a diazo coupling reaction between amino compounds (precursor) and phenol derivatives.

The nitro compounds (precursor) which are used for the reductive synthesis of the photosensitive azobenzene derivatives represented by the general formula (1) may be produced by (a) introducing a substituent into nitrobenzene derivatives, for example. Examples of the nitro compounds include, but are not limited to, 3-dodecyloxy-2-nitrotoluene, 3-methyl-4-nitrophenol and the like.

The amino compounds (precursor) which are used for the oxidative synthesis of the photosensitive azobenzene derivatives represented by the general formula (1) may be produced by (b) reducing the nitro compounds obtained by the step (a), for example. Examples of the amino compounds include, but are not limited to, 2-amino-3-dodecyloxytoluene and the like.

Examples of the phenol derivatives which are subjected to a diazo coupling reaction with the amino compounds (precursor) include, but are not limited to, 3-methyl-4-nitrophenol, 3,5-dimethylphenol and the like. Examples of the amino compounds include, but are not limited to, 4-aminophenol, 4-amino-3-methylphenol and the like.

The photosensitive azobenzene derivatives according to the present invention show a crystal phase. The photosensitive azobenzene derivatives according to the present invention undergo reversible phase transition from a crystal phase to a liquid phase along with isomerization of the azo bonding (—N=N—) by exposure to ultraviolet light or visible light. The term "crystal phase" used herein refers to a solid state in which the molecules of the photosensitive azobenzene derivatives are regularly arranged, and the term "liquid phase" used herein refers to a fluid state in which the molecules of the photosensitive azobenzene derivatives are irregularly arranged. The term "reversible" used herein means a capability that substances which have changed into liquid can be restored to solid.

The liquid phase which has produced by light exposure changes into a crystal phase by exposure to ultraviolet light or visible light. The wavelength of light that causes phase transition differs depending on the electronic effects, the steric effects, and the intermolecular interaction effects of the substituents $R_1$ to $R_{10}$ in the general formula (1). The term "ultraviolet light" used herein refers to light with a wavelength of 200 to 400 nm, and the term "visible light" used herein refers to light with a wavelength of 400 to 700 nm.

As described above, the novel photosensitive azobenzene derivatives according to the present invention (1) undergo phase transition from a crystal phase to a liquid phase along with isomerization of the azo bonding (—N=N—) by exposure to ultraviolet light or visible light, and the liquid phase which has produced by light exposure changes into a crystal phase by exposure to ultraviolet light or visible light; (2) can be arbitrarily controlled in phase transition by photostimulation; (3) change from solid (crystals) into liquid by exposure to ultraviolet light, reversibly restore to solid by exposure of the liquid to visible light, and can repeatedly undergo phase transition between solid and liquid any number of times; and (4) can be produced by a simple production process with high productivity since the photosensitive azobenzene derivatives are produced from a raw material solution through an intermediate, and thus the production cost can be reduced.

A photosensitive material, a thin film, a photoresist material, a printing plate material, or an optical device that can form a pattern by light exposure; or an adhesive or pressure-sensitive adhesive that changes in adhesion (tackiness) by light exposure may be prepared using the photosensitive azobenzene derivatives produced as above.

Specifically, since the hardness, the viscosity, and the fluidity of the compounds differ between a crystal phase and a liquid phase, the photosensitive azobenzene derivatives according to the present invention may be applied to a material that is capable of arbitrarily controlling the hardness, the viscosity, the fluidity, and the diffusion coefficient by light exposure.

Since the refractive index of the compound differs between a crystal phase and a liquid phase, the photosensitive azobenzene derivatives according to the present invention may be applied to a material that is capable of arbitrarily controlling the refractive index by light exposure.

Since the birefringence of the compound differs between a crystal phase and a liquid phase, the photosensitive azobenzene derivatives according to the present invention may be applied to a material that is capable of arbitrarily controlling the birefringence by light exposure.

Since the light scattering intensity differs between a crystal phase and a liquid phase, the photosensitive azobenzene derivatives according to the present invention may be applied to a material that is capable of arbitrarily controlling the scattering intensity by light exposure.

Since the properties of the photosensitive azobenzene derivatives according to the present invention are changed by light exposure, the properties can be changed in an arbitrary area. Specifically, it is possible to arbitrarily change (control or pattern) hardness, viscosity, fluidity, a diffusion coefficient, a refractive index, birefringence, and scattering intensity.

A display or a recording device may be produced by combining the photosensitive azobenzene derivatives with a polarizer, utilizing the difference in birefringence between a crystal phase and a liquid phase. Specifically, when the photosensitive azobenzene derivatives according to the present invention are placed between polarizers that are orthogonal to each other, light passes through the photosensitive azobenzene derivatives in a crystal state that has birefringence, whereas light does not pass through in a liquid state that does not have birefringence. A display or a recording device may be produced by patterning the photosensitive azobenzene derivatives.

A pattern can be formed by exposing the photosensitive azobenzene derivatives according to the invention to patterning light; patterning a crystal phase and a liquid phase; and removing the liquid phase by utilizing the difference in fluidity or diffusion coefficient. This makes it possible to form a resist pattern.

EXAMPLES

The present invention is further described based on the following examples, but the present invention is not limited by such typical examples.

Synthesis and Property Evaluation

The above compounds were synthesized, and the thermophysical properties, the photoresponsivity, and the rheological properties of the synthesized compounds were evaluated. An outline of the examined compounds is shown below.

A pattern-forming experiment using a photomask, a pattern-forming experiment in which an area subjected to photo-induced melting was removed, and an adhesion test were performed as application examples.

Reagents and Devices Used for Experiment

Commercially available reagents and solvents were used directly for synthesis and property evaluation. Silica gel 60 (manufactured by Kanto Kagaku Co., Ltd.) was used for column chromatography.

The NMR (nuclear magnetic resonance) spectrum was measured using an NMR analyzer "Avance 400" (manufactured by Bruker). Mass spectrometry was performed using an Autoflex MALDI-TOF mass spectrometer (manufactured by Bruker).

The thermal behavior of the synthesized compounds was analyzed by differential scanning calorimetry (DSC) ("DSC6100" manufactured by SII Nanotechnology) under dark conditions. The phase transition temperature of each compound is indicated by symbols. For example, "Cr 65 Iso, Iso 53 Cr" means that crystals (Cr) were melted at 65° C. during heating and changed into liquid (Iso), and the liquid solidified at 53° C. during cooling. "Cr 66 LC 72 Iso, Iso 72 LC 53 Cr" means that crystals (Cr) changed into a liquid crystalline phase (LC) at 66° C. during heating, the liquid crystalline phase changed into liquid at 72° C., the liquid changed into a liquid crystalline phase at 72° C. during cooling, and then the liquid crystalline phase changed into crystals at 53° C.

The light exposure experiment for each compound was performed using a sample prepared by enclosing the crystals of the compound in a glass sandwich cell or by placing the crystals of the compound on a slide. Light was applied under observation using a polarizing optical microscope while arbitrarily controlling the temperature on a hot stage. A microscope "BX51" (manufactured by Olympus Corporation) was used as the polarizing optical microscope. A high-pressure mercury lamp was used as a source for light exposure. The light was allowed to pass through a filter so as to carry out the light exposure with an arbitrary wavelength.

Example 1-1

Synthesis of Compound A1B1 (Intermediate 1)

40 mL of distilled water and 10 mL of concentrated hydrochloric acid were added to 4-aminophenol (4.37 g, 40 mmol). After the addition of a solution prepared by dissolving sodium nitrite (3.31 g, 48 mmol) in 10 mL of distilled water to the mixture while stirring the mixture at 0° C., the resulting mixture was stirred at 0° C. for 15 minutes. The resulting solution was added to 60 mL of an aqueous solution of 3,5-dimethylphenol (4.89 g, 40 mmol) and 14 g of sodium hydroxide, and the mixture was stirred for 16 hours. The resulting solution was made acidic using hydrochloric acid under cooling, and a brown precipitate was filtered off. The resulting solid was purified by silica gel column chromatography (eluant: hexane:chloroform=1:1) to obtain Intermediate 1 shown below (brown solid, 6.50 g, yield: 67.1%).

(5)

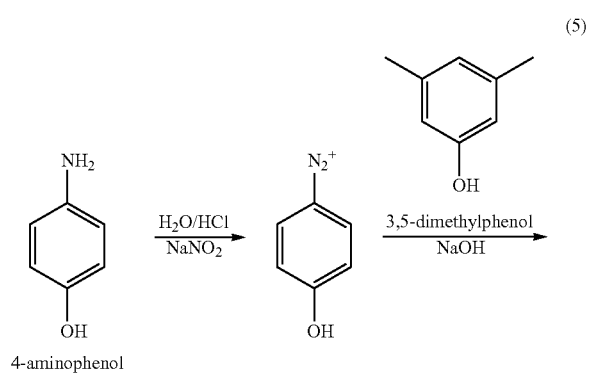
4-aminophenol

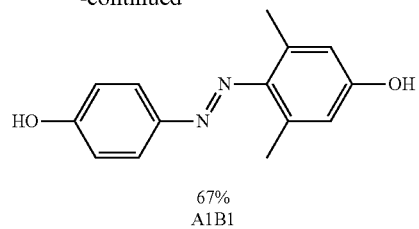
67%
A1B1

Intermediate 1 was subjected to $^1$H NMR analysis and $^{13}$C NMR analysis to determine the structure.

TLC: Rf=0.50 (Ethyl acetate-Hexane, 1:1),
$^1$H NMR (400 MHz, DMSO-$d_6$):
10.05 (s, 1H), 9.70 (s, 1H), 7.67 (d, J=8.8 Hz, 2H), 6.90 (d, J=8.8 Hz, 2H), 6.55 (s, 2H), 2.34 (s, 6H);
$^{13}$C NMR (100 MHz, DMSO-$d_6$):
159.8, 157.3, 145.9, 142.5, 133.8, 123.6, 115.7, 115.6, 19.8.

Example 1-2

Synthesis of Compound A1B1-C12 (Azobenzene Derivative 1)

50 mL of N,N-dimethylformamide (DMF), 1-bromododecane (15 g, 60 mmol), and potassium carbonate (13.8 g, 100 mmol) were added to Compound A1B1 (Intermediate 1) (2.42 g, 10 mmol), and the mixture was stirred at room temperature for 16 hours. After confirming disappearance of Intermediate 4 by thin-layer chromatography (TLC), distilled water was poured into the mixture under cooling, following by extraction with n-hexane. The organic phase was washed once with distilled water, and washed once with a saturated sodium chloride aqueous solution.

The organic phase was dried over anhydrous magnesium sulfate. After removing a solid by filtration, the solvent was evaporated under reduced pressure. The resulting orange solid was purified by silica gel column chromatography (eluant: hexane:chloroform=7:3) to obtain photosensitive Azobenzene Derivative 1 (orange solid, 4.61 g, yield: 79.6%).

(6)

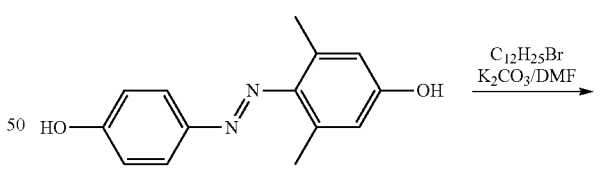
A1B1

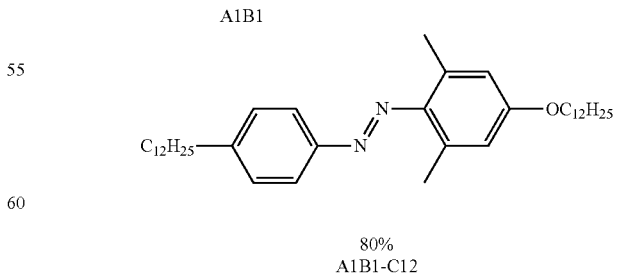
80%
A1B1-C12

Photosensitive Azobenzene Derivative 1 was subjected to $^1$H NMR analysis and $^{13}$C NMR analysis to determine the structure.

TLC: Rf=0.58 (CHCl$_3$-Hexane, 1:1),
$^1$H NMR (400 MHz, CDCl$_3$):
7.88 (d, J=9.0 Hz, 2H), 6.98 (d, J=9.0 Hz, 2H), 6.64 (s, 2H), 4.03 (t, J=6.6 Hz, 2H), 3.97 (t, 6.6 Hz, 2H), 2.44 (s, 6H), 1.74-1.84 (m, 4H), 1.43-1.47 (m, 4H), 1.20-1.38 (m, 32H), 0.87 (t, J=6.8 Hz, 6H);
$^{13}$C NMR (100 MHz, CDCl$_3$):
162.1, 159.8, 147.2, 145.0, 135.1, 124.8, 115.7, 115.4, 69.1, 68.8, 32.6, 30.4, 30.3, 30.3, 30.3, 30.1, 30.0, 30.0, 29.9, 26.7, 26.7, 23.4, 20.7, 14.8.
MS (MALDI-TOF MS): m/z 579.600 (calc. [M+H]$^+$=579.489).

Example 1-3

DSC Measurement of Compound A1B1-C12

The thermal phase transition temperature of Compound A1B1-C12 was determined by differential scanning calorimetry.
Cr 65 Iso, Iso 53 Cr Example 1-4

Light Exposure Experiment 1 for Compound A1B1-C12

The crystal-isotropic phase transition of Compound A1B1-C12 at 40° C. was observed using an optical microscope. The results are shown in FIG. 1.
In FIG. 1, (a) represents an optical micrograph showing a crystal phase at 40° C.; (b) represents an optical micrograph showing a state after exposure to ultraviolet light (365 nm) at 40° C.; (c) represents an optical micrograph showing a state where the sample is exposed to visible light (436 nm) at 40° C. after exposure to ultraviolet light; and (d) represents an optical micrograph showing a state where the compound is second exposed to ultraviolet light at 40° C. after exposure to visible light.
As is clear from FIG. 1, trans-to-cis photoisomerization and phase transition from a crystal phase to an isotropic phase were induced by exposure to ultraviolet light, and the shape changed into a droplet (see (b)). Cis-to-trans photoisomerization and phase transition from an isotropic phase to a crystal phase were induced by exposure of the isotropic phase to visible light, and crystal was produced (see (c)). Isomerization and phase transition from a crystal phase to an isotropic phase, as observed in the first exposure to ultraviolet light, were induced by second exposure of the sample (crystal phase) to ultraviolet light, and the shape changed into a droplet (see (d)).

Example 1-5

Light Exposure Experiment 2 for Compound A1B1-C12

Figure 2:
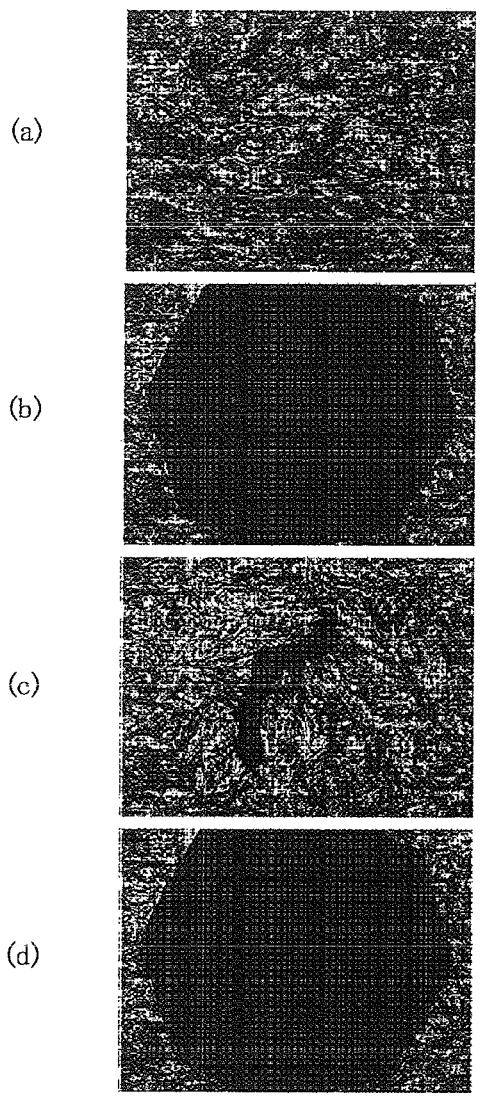
FIG. 2 represents a polarizing optical micrograph showing the crystal-isotropic phase transition of Compound A1B1-C12 at 40° C.

The crystal-isotropic phase transition of Compound A1B1-C12 at 40° C. was observed using a polarizing optical microscope. The results are shown in FIG. 2.
In FIG. 2, (a) represents a polarizing optical micrograph showing a crystal phase at 40° C.; (b) represents a polarizing optical micrograph showing a state where the sample is exposed to ultraviolet light (365 nm) at 40° C.; (c) represents a polarizing optical micrograph showing a state where the sample is exposed to visible light (436 nm) at 40° C. after exposure to ultraviolet light; and (d) represents a polarizing optical micrograph showing a state where the sample is second exposed to ultraviolet light at 40° C. after exposure to visible light.
As is clear from FIG. 2, photoisomerization and phase transition from a crystal phase to an isotropic phase were induced by exposure to ultraviolet light, and a dark field was observed in crossed nicols observation (see (b)). Cis-to-trans photoisomerization and phase transition from an isotropic phase to a crystal phase were induced by exposure of the isotropic phase to visible light, and crystal was produced (see (c)). Isomerization and phase transition from a crystal phase to an isotropic phase, as observed in the first exposure to ultraviolet light, were induced by second exposure of the sample (crystal phase) to ultraviolet light, and a dark field was observed in crossed nicols observation (see (d)).

Example 1-6

Light Exposure Experiment 3 for Compound A1B1-C12

Figure 3:
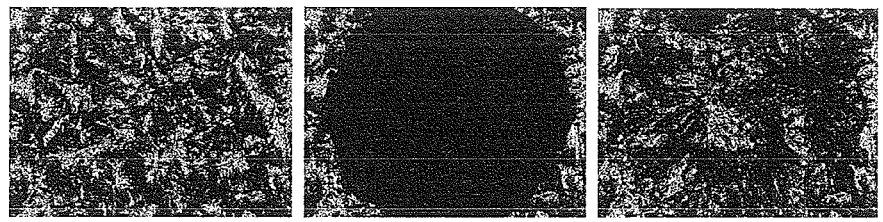
FIG. 3 represents a polarizing optical micrograph showing the crystal-isotropic phase transition of Compound A1B1-C12 at 35° C.

The crystal-isotropic phase transition of Compound A1B1-C12 at 35° C. was observed using a polarizing optical microscope. The results are shown in FIG. 3.
In FIG. 3, the left represents a polarizing optical micrograph before light exposure; the center represents a polarizing optical micrograph just after exposure to ultraviolet light (365 nm) for 110 seconds; and the right represents a polarizing optical micrograph after exposure to visible light (436 nm) for 2 seconds wherein the sample was exposed to ultraviolet light as stated above.
These phenomena suggest that the crystal-isotropic phase transition of Compound A1B1-C12 is reversible and that this azobenzene derivative can form a photosensitive material which is capable of reversible use.

Example 2-1

Synthesis of Compound A1B2 (Intermediate 2)

50 mL of 2.4N hydrochloric acid was added to 4-aminophenol (4.36 g, 40 mmol). After the addition of a solution prepared by dissolving sodium nitrite (3.31 g, 48 mmol) in 5 mL of distilled water to the mixture while stirring the mixture at 0° C., the resulting mixture was stirred at 0° C. for 15 minutes. The resulting solution was added to a mixture of 6-isopropyl-m-cresol (6.01 g, 40 mmol) and 60 mL of a 20% sodium hydroxide aqueous solution, and the mixture was stirred for 16 hours. The resulting solution was made acidic using hydrochloric acid under cooling, and a brown precipitate was filtered off. The resulting solid was purified by silica gel column chromatography (eluant: ethyl acetate:hexane=1:4), and recrystallized from hexane to obtain Compound A1B2 (brown solid, 9.86 g, yield: 91%).

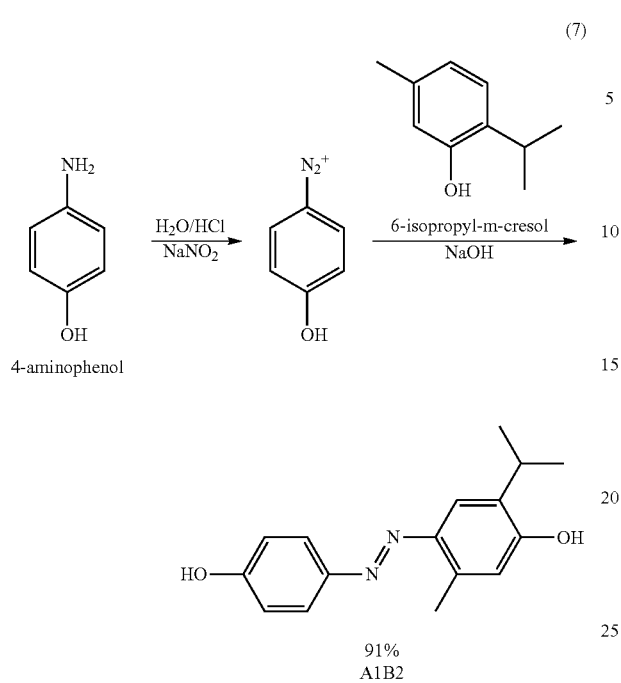

(7)

Compound A1B2 (Intermediate 2) was subjected to $^1$H NMR analysis to determine the structure.

$^1$H NMR (400 MHz, DMSO-d$_6$):

9.99 (s, 2H), 7.70 (d-d, J$_1$=6.8 Hz, J$_2$=2.0 Hz, 2H), 7.47 (s, 1H), 6.88 (d-d, J$_1$=6.8 Hz, J$_2$=2.0 Hz, 2H), 6.75 (s, 1H), 3.15 (septet, J=6.9 Hz, 1H), 2.59 (s, 3H), 2.53 (s, 3H), 1.16 (d, J=6.9 Hz, 6H).

Example 2-2

Synthesis of Compound A1B2-C12 (Azobenzene Derivative 2)

10 mL of DMF, 1-bromododecane (16.5 g, 66 mmol), and potassium carbonate (15.2 g, 110 mmol) were added to Compound A1B2 (2.97 g, 11.0 mmol), and the mixture was stirred at 80° C. for 2 hours, and then stirred at room temperature for 16 hours. The solvent was evaporated under reduced pressure, followed by recrystallization from hexane to obtain Compound A1B2-C12 (orange solid, 2.79 g, yield: 42%).

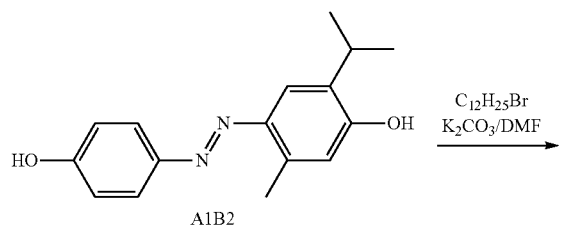

(8)

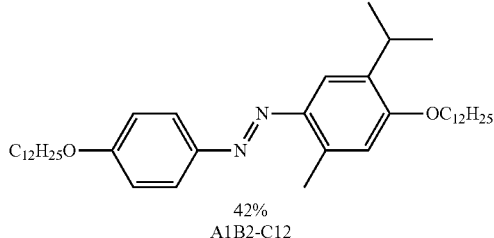

Compound A1B2-C12 was subjected to $^1$H NMR analysis and $^{13}$C NMR analysis to determine the structure.

$^1$H NMR (400 MHz, CDCl$_3$):

7.95 (d-d, J$_1$=7.0 Hz, J$_2$=2.0 Hz, 2H), 7.86 (s, 1H), 6.96 (d-d, J$_1$=7.0 Hz, J$_2$=2.0 Hz, 2H), 6.72 (s, 1H), 4.02 (q, J=6.4 Hz, 4H), 3.26 (septet, J=6.9 Hz, 1H), 2.66 (s, 3H), 1.78-1.85 (m, 4H), 1.41-1.52 (m, 4H), 1.22-1.40 (m, 38H), 0.84-0.88 (m, 6H).

$^{13}$C NMR (100 MHz, CDCl$_3$):

160.9, 159.0, 147.1, 144.2, 137.9, 135.6, 124.2, 114.6, 113.8, 112.8, 68.3, 68.1, 31.9, 29.7, 29.6, 29.6, 29.6, 29.4, 29.3, 29.3, 29.2, 27.2, 26.2, 26.0, 22.7, 22.5, 17.5, 14.1.

MS (MALDI-TOF MS): m/z 607.796 (calc. [M+H]$^+$=607.520).

Example 2-3

DSC Measurement of Compound A1B2-C12

The thermal phase transition temperature of Compound A1B2-C12 was determined by differential scanning calorimetry.

Cr 79 Iso, Iso 50 Cr

Example 2-4

Light Exposure Experiment for Compound A1B2-C12

The crystal-isotropic phase transition of Compound A1B2-C12 at 50° C. was observed using a polarizing optical microscope. The results are shown in FIG. 4.

Figure 4:
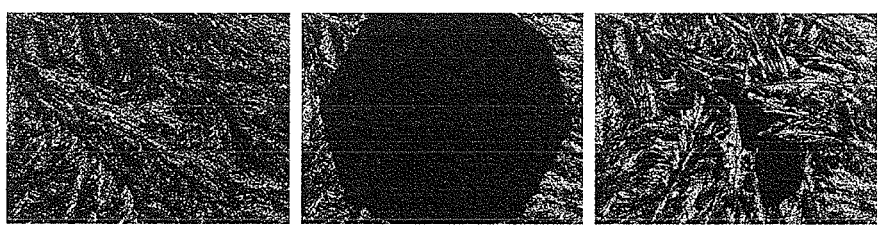
FIG. 4 represents a polarizing optical micrograph showing the crystal-isotropic phase transition of Compound A1B2-C12 at 50° C.

In FIG. 4, the left represents a polarizing optical micrograph before light exposure; the center represents a polarizing optical micrograph just after exposure to ultraviolet light (365 nm) for 311 seconds; and the right represents a polarizing optical micrograph after exposure to visible light (436 nm) for 75 seconds wherein the sample was exposed to ultraviolet light as stated above.

Example 3-1

Synthesis of Compound A1B3 (Intermediate 3)

25 mL of 2.4N hydrochloric acid was added to 4-aminophenol (2.18 g, 20 mmol). After the addition of a solution prepared by dissolving sodium nitrite (1.66 g, 24 mmol) in 5 mL of distilled water to the mixture while stirring the mixture at 0° C., the resulting mixture was stirred at 0° C. for 15 minutes. The resulting solution was added to a mixture of 5-isopropyl-o-cresol (3.00 g, 20 mmol) and 30 mL of a 20% sodium hydroxide aqueous solution, and the mixture was stirred for 16 hours. The resulting solution was made acidic using hydrochloric acid under cooling, and a brown precipitate was filtered off. The resulting solid was purified by silica gel column chromatography (eluant: ethyl acetate:hexane=3:7), and recrystallized from hexane to obtain Compound A1B3 (brown solid, 3.80 g, yield: 70%).

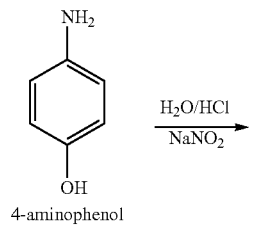

4-aminophenol

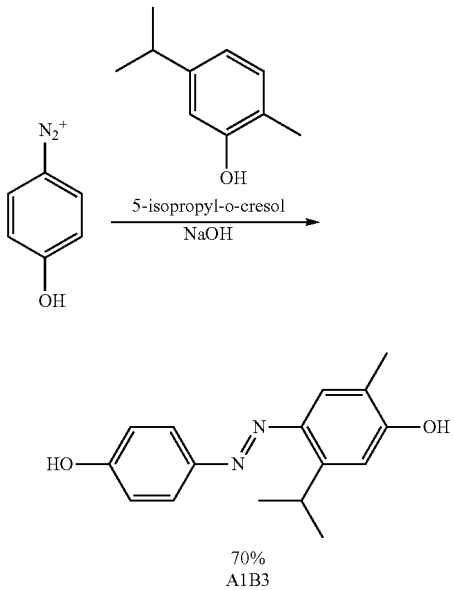

70%
A1B3

Compound A1B3 (Intermediate 3) was subjected to $^1$H NMR analysis to determine the structure.

$^1$H NMR (400 MHz, DMSO-d$_6$):

10.02 (s, 2H), 7.68 (d-d, J$_1$=6.8 Hz, J$_2$=2.0 Hz, 2H), 7.41 (s, 1H), 6.89 (d-d, J$_1$=6.8 Hz, J$_2$=2.0 Hz, 2H), 6.83 (s, 1H), 3.98 (septet, J=6.9, 1H), 2.11 (s, 3H), 1.23 (d, J=6.9, 6H).

Example 3-2

Synthesis of Compound A1B3-C12 (Azobenzene Derivative 3)

27.5 mL of DMF, 1-bromododecane (8.25 g, 33 mmol), and potassium carbonate (7.59 g, 55 mmol) were added to Compound A1B3 (1.90 g, 5.0 mmol), and the mixture was stirred at 80° C. for 2 hours, and then stirred at room temperature for 16 hours. After evaporating the solvent under reduced pressure, the resulting solid was purified by silica gel column chromatography (eluant: ethyl acetate:hexane=1:9), and recrystallized from acetone to obtain Compound A1B3-C12 (orange solid, 2.81 g, yield: 66%).

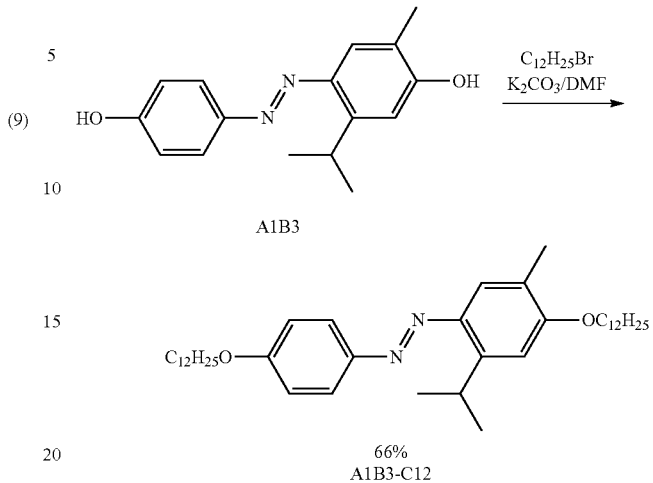

66%
A1B3-C12

The compound A1B3-C12 was subjected to $^1$H NMR analysis and $^{13}$C NMR analysis to determine the structure.

$^1$H NMR (400 MHz, CDCl$_3$):

7.84 (d-d, J$_1$=7.0 Hz, J$_2$=2.0 Hz, 2H), 7.56 (s, 11-1), 6.96 (d-d, J$_1$=7.0 Hz, J$_2$=2.0 Hz, 2H), 6.78 (s, 1H), 4.13 (septet, J=6.9 Hz, 1H), 3.99-4.05 (m, 4H), 2.20 (s, 3H), 1.76-1.85 (m, 4H), 1.41-1.52 (m, 4H), 1.21-1.40 (m, 38H), 0.84-0.88 (m, 6H).

$^{13}$C NMR (100 MHz, CDCl$_3$):

160.9, 160.3, 148.3, 147.0, 142.7, 125.2, 124.3, 117.8, 114.7, 107.8, 68.4, 68.2, 31.9, 29.7, 29.6, 29.6, 29.4, 29.3, 29.3, 29.2, 27.7, 26.1, 26.0, 24.0, 22.7, 15.9, 14.1.

MS (MALDI-TOF MS): m/z 607.643 (calc. [M+H]$^+$=607.520).

Example 3-3

DSC Measurement of Compound A1B3-C12

The thermal phase transition temperature of Compound A1B3-C12 was determined by differential scanning calorimetry.

Cr 64 Iso, Iso 31 Cr

Example 3-4

Light Exposure Experiment for Compound A1B3-C12

The crystal-isotropic phase transition of Compound A1B3-C12 at 40° C. was observed using a polarizing optical microscope. The results are shown in FIG. 5.

Figure 5:
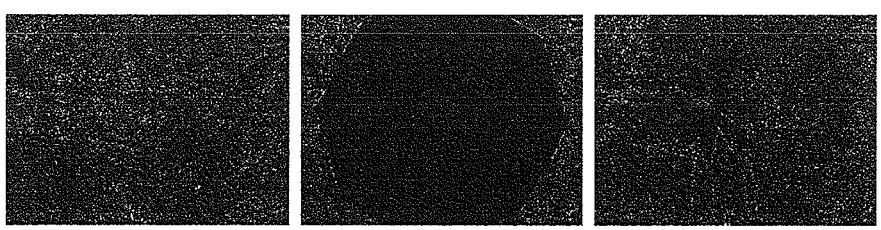
FIG. 5 represents a polarizing optical micrograph showing the crystal-isotropic phase transition of Compound A1B3-C12 at 40° C.

In FIG. 5, the left represents a polarizing optical micrograph before light exposure; the center represents a polarizing optical micrograph just after exposure to ultraviolet light (365 nm) for 111 seconds; and the right represents a polarizing optical micrograph after exposure to visible light (436 nm) for 235 seconds wherein the sample was exposed to ultraviolet light as stated above.

Example 4-1

Synthesis of Compound A1B4 (Intermediate 4)

12.5 mL of 2.4N hydrochloric acid was added to 4-aminophenol (1.09 g, 10 mmol). After the addition of a solution prepared by dissolving sodium nitrite (0.828 g, 12 mmol) in 5 mL of distilled water to the mixture while stirring the mixture at 0° C., the resulting mixture was stirred at 0° C. for 15 minutes. The resulting solution was added to a mixture of m-cresol (1.08 g, 10 mmol) and 18.5 mL of a 20% sodium hydroxide aqueous solution, and the mixture was stirred for 16 hours. The resulting solution was made acidic using hydrochloric acid under cooling, and a brown precipitate was filtered off. The resulting solid was purified by silica gel column chromatography (eluant: ethyl acetate:hexane=1:1) to obtain Compound A1B4 (brown solid, 1.07 g, yield: 47%).

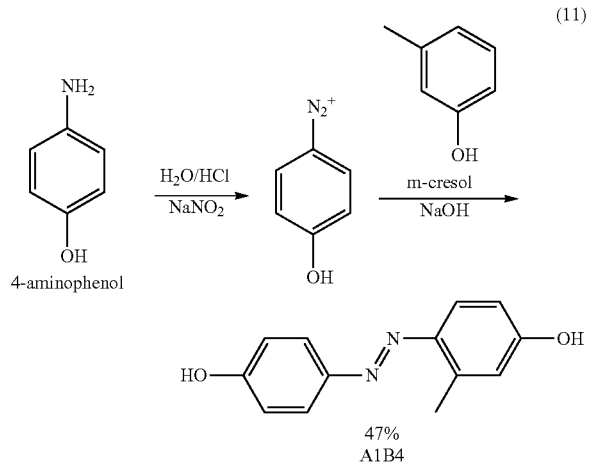

(11)

47%
A1B4

Compound A1B4 (Intermediate 4) was subjected to $^1$H NMR analysis to determine the structure.

$^1$H NMR (400 MHz, DMSO-$d_6$):

10.05 (s, 2H), 7.69 (d-d, $J_1$=6.8 Hz, $J_2$=2.0 Hz, 2H), 7.50 (d, J=8.8 Hz, 1H), 6.89 (d-d, $J_1$=6.8 Hz, $J_2$=2.0 Hz, 2H), 6.73 (d, J=2.4 Hz, 1H), 6.66 (d-d, $J_1$=8.8 Hz, $J_2$=2.6 Hz, 1H), 2.57 (s, 3H).

Example 4-2

Synthesis of Compound A1B4-C12 (Azobenzene Derivative 4)

5.0 mL of DMF, 1-bromododecane (1.3 g, 5.2 mmol), and potassium carbonate (3.4 g, 25 mmol) were added to Compound A1B4 (0.214 g, 0.9 mmol), and the mixture was stirred at 80° C. for 2 hours, and then stirred at room temperature for 16 hours. After evaporating the solvent under reduced pressure, the resulting solid was purified by gel permeation chromatography (GPC) to obtain Compound A1B4-C12 (orange solid, 0.129 g, yield: 26%).

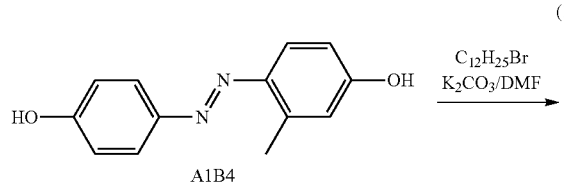

(12)

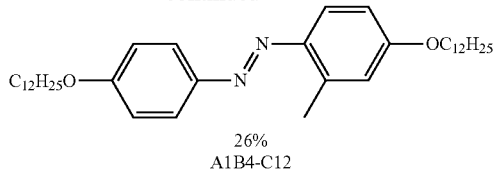

26%
A1B4-C12

Compound A1B4-C12 was subjected to $^1$H NMR analysis and $^{13}$C NMR analysis to determine the structure.

$^1$H NMR (400 MHz, CDCl$_3$):

7.87 (d-d, $J_1$=6.8 Hz, $J_2$=2.0 Hz, 2H), 7.73 (d, J=8.9 Hz, 1H), 6.96 (d-d, $J_1$=6.8 Hz, $J_2$=2.0 Hz, 2H), 6.80 (d, J=2.7 Hz, 1H), 6.76 (d-d, $J_1$=8.9 Hz, $J_2$=2.7 Hz, 1H), 3.97-4.02 (m, 4H), 2.67 (s, 3H), 1.74-1.83 (m, 4H), 1.19-1.52 (m, 36H), 0.85-0.88 (m, 6H).

$^{13}$C NMR (100 MHz, CDCl$_3$):

161.4, 161.1, 146.8, 144.7, 140.5, 124.3, 117.4, 116.0, 114.7, 112.9, 68.4, 68.3, 31.9, 29.7, 29.6, 29.6, 29.6, 29.4, 29.3, 29.2, 26.0, 22.7, 17.8, 14.1.

MS (MALDI-TOF MS): m/z 565.672 (calc. [M+H]$^+$=565.473).

Example 4-3

DSC Measurement of Compound A1B4-C12

The thermal phase transition temperature of Compound A1B4-C12 was determined by differential scanning calorimetry.

Cr 75 Iso, Iso 70 Cr

Example 4-4

Light Exposure Experiment for Compound A1B4-C12

The crystal-isotropic phase transition of Compound A1B4-C12 at 45° C. was observed using a polarizing optical microscope. The results are shown in FIG. 6.

Figure 6:
FIG. 6 represents a polarizing optical micrograph showing the crystal-isotropic phase transition of Compound A1B4-C12 at 45° C.

In FIG. 6, the left represents a polarized light micrograph before light exposure; the center represents a polarizing optical micrograph just after exposure to ultraviolet light (365 nm) for 360 seconds; and the right represents a polarizing optical micrograph after exposure to visible light (436 nm) for 7 seconds wherein the sample was exposed to ultraviolet light as stated above.

Example 5-1

Synthesis of Compound A1B5 (Intermediate 5)

12.5 mL of 2.4N hydrochloric acid was added to 4-aminophenol (1.09 g, 10 mmol). After the addition of a solution prepared by dissolving sodium nitrite (0.828 g, 12 mmol) in 5 mL of distilled water to the mixture while stirring the mixture at 0° C., the resulting mixture was stirred at 0° C. for 15 minutes. The resulting solution was added to a mixture of 6-tert-butyl-o-cresol (1.64 g, 10 mmol) and 18.5 mL of a 20% sodium hydroxide aqueous solution, and the mixture was stirred for 16 hours. The resulting solution was made acidic using hydrochloric acid under cooling, and extracted with ethyl acetate. The resulting solid was purified by silica gel column chromatography (eluant: ethyl acetate:hexane=3:7) to obtain Compound A1B5 (brown solid, 1.89 g, yield: 67%).

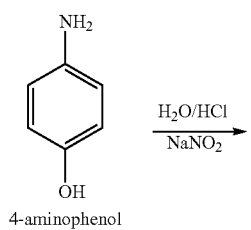

4-aminophenol

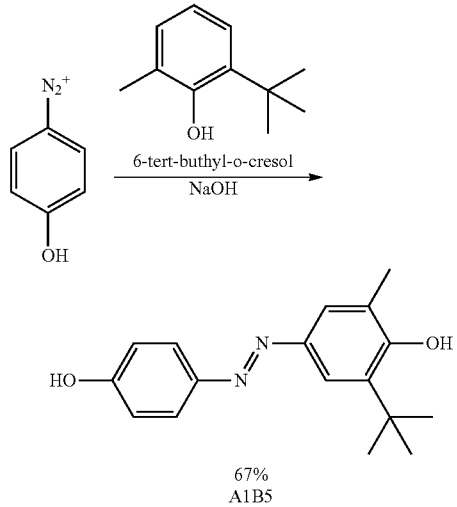

67%
A1B5

Compound A1B5 (Intermediate 5) was subjected to $^1$H NMR analysis to determine the structure.

$^1$H NMR (400 MHz, DMSO-$d_6$):

10.07 (s, 1H), 8.81 (s, 1H), 7.68 (d-d, $J_1$=6.7 Hz, $J_2$=2.0 Hz, 2H), 7.60 (d, J=2.4 Hz, 1H), 7.48 (d, J=2.4 Hz, 1H), 6.87 (d-d, $J_1$=6.7 Hz, $J_2$=2.0 Hz, 2H), 2.27 (s, 3H), 1.41 (s, 9H).

Example 5-2

Synthesis of Compound A1B5-C12 (Azobenzene Derivative 5)

27.5 mL of DMF, 1-bromododecane (8.25 g, 33 mmol), and potassium carbonate (7.59 g, 55 mmol) were added to Compound A1B5 (0.571 g, 2.0 mmol), and the mixture was stirred at 80° C. for 2 hours, and then stirred at room temperature for 16 hours. After evaporating the solvent under reduced pressure, the resulting solid was purified by gel permeation chromatography (GPC) to obtain Compound A1B5-C12 (orange solid, 1.03 g, yield: 83%).

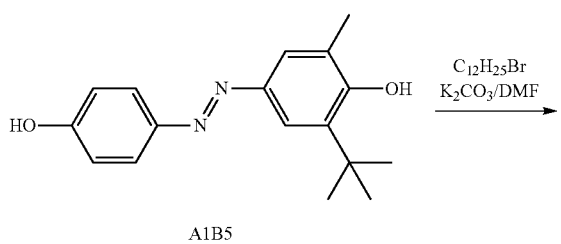

A1B5

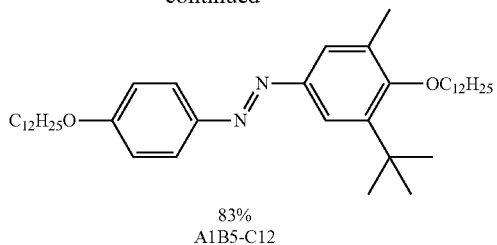

83%
A1B5-C12

Compound A1B5-C12 was subjected to $^1$H NMR analysis and $^{13}$C NMR analysis to determine the structure.

$^1$H NMR (400 MHz, CDCl$_3$):

7.90 (d, J=8.9 Hz, 2H), 7.79 (d, J=2.4 Hz, 1H), 6.97 (d, J=8.9 Hz, 2H), 4.02 (t, J=6.6 Hz, 2H), 3.84 (t, J=6.7 Hz, 2H), 2.36 (s, 3H), 1.70-1.88 (m, 4H), 1.20-1.53 (m, 45H), 0.85-0.88 (m, 6H).

$^{13}$C NMR (100 MHz, CDCl$_3$):

161.5, 159.6, 147.8, 146.7, 143.5, 132.3, 124.6, 122.3, 121.6, 114.7, 72.6, 68.4, 35.3, 31.9, 31.0, 30.0, 29.7, 29.6, 29.6, 29.4, 29.3, 29.2, 26.0, 26.0, 22.7, 17.6, 14.1.

MS (MALDI-TOF MS): m/z 621.697 (calc. [M+H]$^+$=621.536).

Example 5-3

DSC Measurement of Compound A1B5-C12

The thermal phase transition temperature of Compound A1B5-C12 was determined by differential scanning calorimetry.

Cr 25 Cr 47 Iso (Note: A clear crystallization peak was not observed during cooling since the crystallization rate was low).

Example 5-4

Light Exposure Experiment 1 for Compound A1B5-C12

The crystal-isotropic phase transition of Compound A1B5-C12 at 27° C. was observed using a polarizing optical microscope. The results are shown in FIG. 7.

Figure 7:
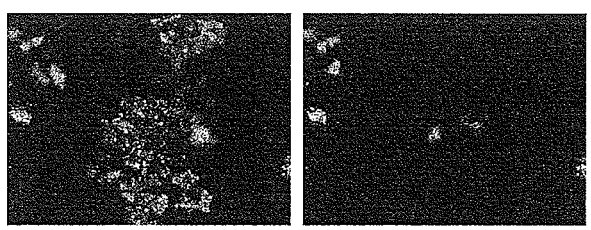
FIG. 7 represents a polarizing optical micrograph showing the crystal-isotropic phase transition of the compound A1B5-C12 at 27° C.

In FIG. 7, the left represents a polarizing optical micrograph before light exposure; and the right represents a polarizing optical micrograph just after exposure to ultraviolet light (365 nm) for 170 seconds.

Example 5-5

Light Exposure Experiment 2 for Compound A1B5-C12

The crystal-isotropic phase transition of Compound A1B5-C12 at 23° C. was observed using a polarizing optical microscope. The results are shown in FIG. 8.

Figure 8:
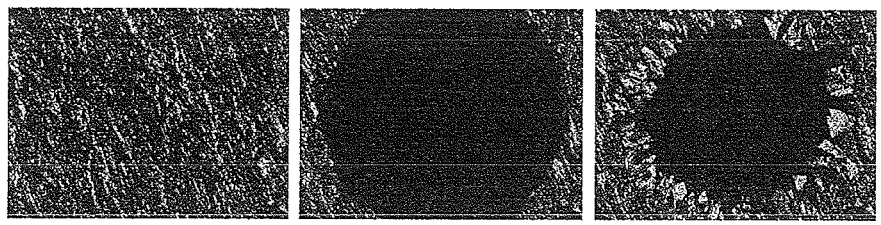
FIG. 8 represents a polarizing optical micrograph showing the crystal-isotropic phase transition of Compound A1B5-C12 at 23° C.

In FIG. 8, the left represents a polarizing optical micrograph before light exposure; the center represents a polarizing optical micrograph just after exposure to ultraviolet light (365 nm) for 19 seconds; and the right represents a polarizing optical micrograph after exposure to visible light (436 nm) for 300 seconds wherein the sample was exposed to ultraviolet light as stated above.

Example 6-1

Synthesis of Compound A1B6 (Intermediate 6)

25 mL of 2.4N hydrochloric acid was added to 4-aminophenol (2.18 g, 20 mmol). After the addition of a solution prepared by dissolving sodium nitrite (1.66 g, 24 mmol) in 2 mL of distilled water to the mixture while stirring the mixture at 0° C., the resulting mixture was stirred at 0° C. for 15 minutes. The resulting solution was added to a mixture of 2-isopropylphenol (2.72 g, 20 mmol) and 8 mL of a 20% sodium hydroxide aqueous solution, and the mixture was stirred for 16 hours. The resulting solution was made acidic using hydrochloric acid under cooling, and a brown precipitate was filtered off. The resulting solid was purified by silica gel column chromatography (eluant: ethyl acetate:hexane=1:2), and recrystallized from hexane to obtain Compound A1B6 (brown solid, 2.42 g, yield: 47%).

(15)

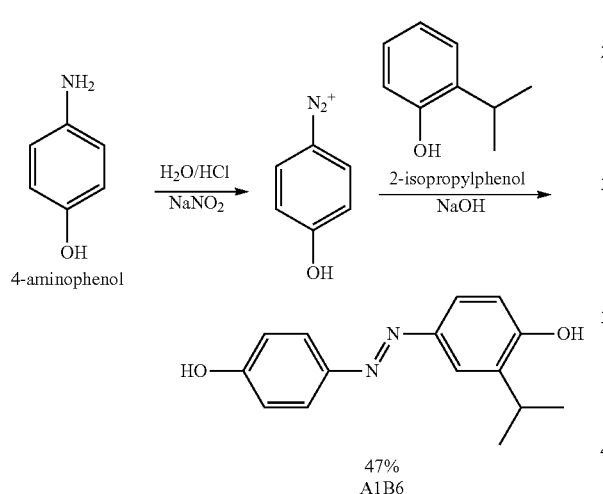

Compound A1B6 (Intermediate 6) was subjected to $^1$H NMR analysis to determine the structure.

$^1$H NMR (400 MHz, DMSO-d$_6$):

10.08 (s, 1H), 10.06 (s, 1H), 7.71 (d, J=6.8 Hz, 2H), 7.66 (d, J=2.4 Hz, 1H), 7.54 (d-d, J$_1$=8.6 Hz, J$_2$=2.4 Hz, 1H), 6.93 (d, J=8.6 Hz, 1H), 6.90 (d, J=6.8 Hz, 2H), 3.25 (septet, J=6.9 Hz, 1H), 1.22 (d, J=6.9 Hz, 6H).

Example 6-2

Synthesis of Compound A1B6-C12 (Azobenzene Derivative 6)

10 mL of acetone, 1-bromododecane (0.548 g, 2.2 mmol), and potassium carbonate (1.10 g, 8 mmol) were added to Compound A1B6 (0.256 g, 1.0 mmol), and the mixture was stirred at 60° C. for 18 hours. After evaporating the solvent under reduced pressure, the resulting solid was purified by silica gel column chromatography (eluant: ethyl acetate:hexane=1:9) to obtain Compound A1B6-C12 (orange solid, 0.487 g, yield: 82%).

(16)

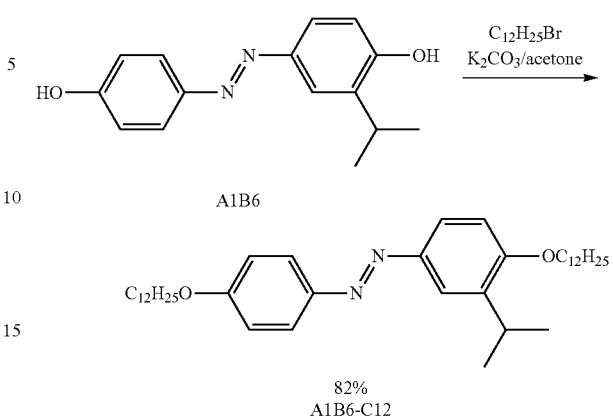

Compound A1B6-C12 was subjected to $^1$H NMR analysis and $^{13}$C NMR analysis to determine the structure.

$^1$H NMR (400 MHz, CDCl$_3$):

7.92 (d, J=8.9 Hz, 2H), 7.86 (d, J=2.4 Hz, 1H), 7.78 (d-d, J$_1$=8.6 Hz, J$_2$=2.4 Hz, 1H), 7.01 (d-d, J$_1$=6.9 Hz, J$_2$=2.1 Hz, 2H), 6.94 (d, J=8.8 Hz, 1H), 4.03-4.08 (m, 4H), 3.38 (septet, J=6.9 Hz, 1H), 1.79-1.89 (m, 4H), 1.43-1.56 (m, 4H), 1.24-1.40 (m, 38H), 0.88-0.92 (m, 6H).

$^{13}$C NMR (100 MHz, CDCl$_3$):

161.2, 158.8, 146.7, 146.5, 137.8, 124.3, 122.2, 120.7, 114.7, 111.0, 68.4, 68.3, 31.9, 29.7, 29.6, 29.6, 29.6, 29.4, 29.3, 29.3, 29.2, 27.2, 26.2, 26.0, 22.7, 22.5, 14.1.

MS (MALDI-TOF MS): m/z 593.605 (calc. [M+H]$^+$=593.505).

Example 6-3

DSC measurement of Compound A1B6-C12

The thermal phase transition temperature of Compound A1B6-C12 was determined by differential scanning calorimetry.

Cr 66 Iso, Iso 43 Cr

Example 6-4

Light Exposure Experiment for Compound A1B6-C12

The crystal-isotropic phase transition of Compound A1B6-C12 at 40° C. was observed using a polarizing optical microscope. The results are shown in FIG. 9.

Figure 9:
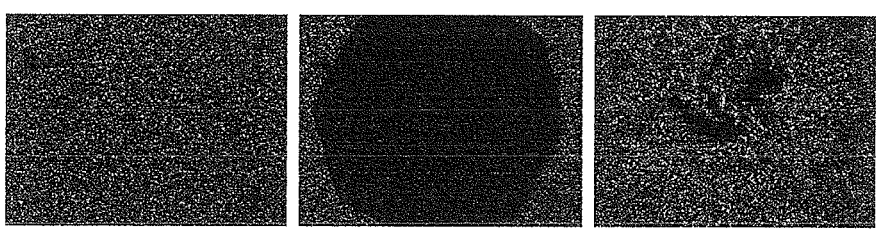
FIG. 9 represents a polarizing optical micrograph showing the crystal-isotropic phase transition of Compound A1B6-C12 at 40° C.

In FIG. 9, the left represents a polarizing optical micrograph before light exposure; the center represents a polarizing optical micrograph just after exposure to ultraviolet light (365 nm) for 51 seconds; and the right represents a polarizing optical micrograph after exposure to visible light (436 nm) for 86 seconds wherein the sample was exposed to ultraviolet light as stated above.

Example 7-1

Synthesis of Compound A1B7 (Intermediate 7)

25 mL of 2.4N hydrochloric acid was added to 4-aminophenol (2.18 g, 20 mmol). After the addition of a solution prepared by dissolving sodium nitrite (1.66 g, 24 mmol) in 2 mL of distilled water to the mixture while stirring the mixture at 0° C., the resulting mixture was stirred at 0° C. for 15 minutes. The resulting solution was added to a mixture of 2,6-diisopropylphenol (3.56 g, 20 mmol) and 8 mL of a 20% sodium hydroxide aqueous solution, and the mixture was stirred for 16 hours. The resulting solution was made acidic using hydrochloric acid under cooling, and a brown precipitate was filtered off. The resulting solid was washed with water, dissolved in acetone, and dehydrated using anhydrous sodium sulfate, and the solvent was evaporated under reduced pressure. The resulting brown solid was purified by silica gel column chromatography (eluant: ethyl acetate:hexane=1:2), and recrystallized from hexane to obtain a compound A1B7 (brown solid, 1.89 g, yield: 32%).

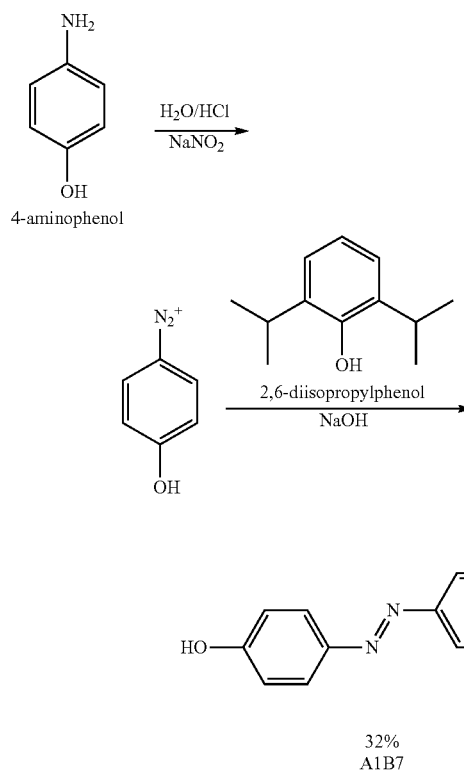

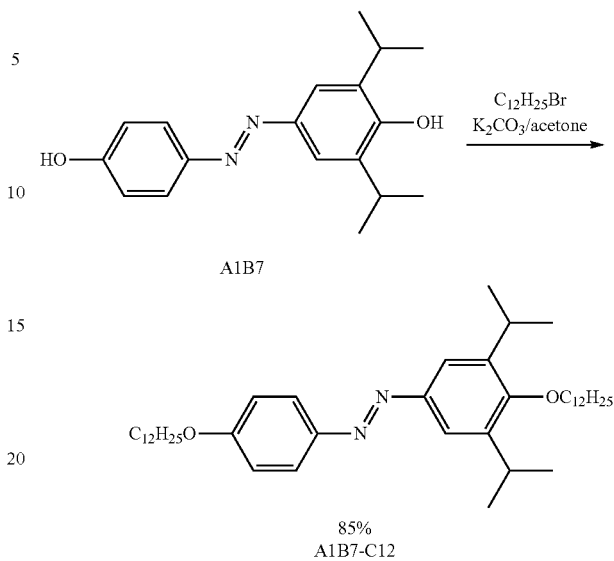

Compound A1B7 (Intermediate 7) was subjected to $^1$H NMR analysis to determine the structure.

$^1$H NMR (400 MHz, DMSO-$d_6$):

10.09 (s, 1H), 8.80 (s, 1H), 7.73 (d-d, $J_1$=6.8 Hz, $J_2$=2.0 Hz, 2H), 7.53 (s, 2H), 6.90 (d-d, $J_1$=6.8 Hz, $J_2$=2.0 Hz, 1H), 3.36 (septet, J=6.8 Hz, 2H), 1.21 (d, J=6.8 Hz, 12H).

Example 7-2

Synthesis of Compound A1B7-C12 (Azobenzene Derivative 7)

10 mL of acetone, 1-bromododecane (0.548 g, 2.2 mmol), and potassium carbonate (1.10 g, 8 mmol) were added to Compound A1B7 (0.298 g, 1.0 mmol), and the mixture was stirred at 60° C. for 18 hours. After evaporating the solvent under reduced pressure, the resulting solid was purified by silica gel column chromatography (eluant: ethyl acetate:hexane=1:9) to obtain Compound A1B7-C12 (orange solid, 0.540 g, yield: 85%).

Compound A1B7-C12 was subjected to $^1$H NMR analysis and $^{13}$C NMR analysis to determine the structure.

$^1$H NMR (400 MHz, CDCl$_3$):

7.92 (d-d, $J_1$=7.0 Hz, $J_2$=2.0 Hz, 2H), 7.69 (s, 2H), 7.01 (d-d, $J_1$=7.0 Hz, $J_2$=2.0 Hz, 2H), 4.05 (t, J=6.6 Hz, 2H), 3.79 (t, J=6.6 Hz, 2H), 3.37 (septet, J=6.9 Hz, 2H), 1.79-1.90 (m, 4H), 1.46-1.58 (m, 4H), 1.27-1.40 (m, 42H), 0.88-0.92 (m, 6H).

$^{13}$C NMR (100 MHz, CDCl$_3$):

161.5, 156.0, 149.3, 146.8, 142.9, 124.6, 118.8, 114.7, 75.1, 68.4, 31.9, 30.4, 29.6, 29.6, 29.6, 29.5, 29.4, 29.3, 29.2, 26.8, 26.1, 26.0, 24.0, 22.7, 14.1.

MS (MALDI-TOF MS): m/z 635.624 (calc. [M+H]$^+$=635.552).

Example 7-3

DSC Measurement of Compound A1B7-C12

The thermal phase transition temperature of Compound A1B7-C12 was determined by differential scanning calorimetry.

Cr 26 Cr 51 Iso, Iso 21 Cr

Example 7-4

Light Exposure Experiment for Compound A1B7-C12

The crystal-isotropic phase transition of Compound A1B7-C12 at 25° C. was observed using a polarizing optical microscope. The results are shown in FIG. 10.

Figure 10:
FIG. 10 represents a polarizing optical micrograph showing the crystal-isotropic phase transition of Compound A1B7-C12 at 25° C.

In FIG. 10, the left represents a polarizing optical micrograph before light exposure; the center represents a polarizing optical micrograph just after exposure to ultraviolet light (365 nm) for 30 seconds; and the right represents a polarizing optical micrograph after exposure to visible light (436 nm) for 190 seconds wherein the sample was exposed to ultraviolet light as stated above.

Example 8-1

Synthesis of Compound A1B8 (Intermediate 8)

25 mL of 2.4N hydrochloric acid was added to 4-aminophenol (2.18 g, 20 mmol). After the addition of a solution prepared by dissolving sodium nitrite (1.66 g, 24 mmol) in 2 mL of distilled water to the mixture while stirring the mixture at 0° C., the resulting mixture was stirred at 0° C. for 15 minutes. The resulting solution was added to a mixture of 2-tert-butylphenol (3.00 g, 20 mmol) and 8 mL of a 20% sodium hydroxide aqueous solution, and the mixture was stirred for 16 hours. The resulting solution was made acidic using hydrochloric acid under cooling, a brown precipitate was filtered off, and the resulting solid was washed with water. The resulting reddish brown solid was purified by silica gel column chromatography (eluant: ethyl acetate:hexane=1:2), and recrystallized from hexane to obtain Compound A1B8 (brown solid, 2.22 g, yield: 41%).

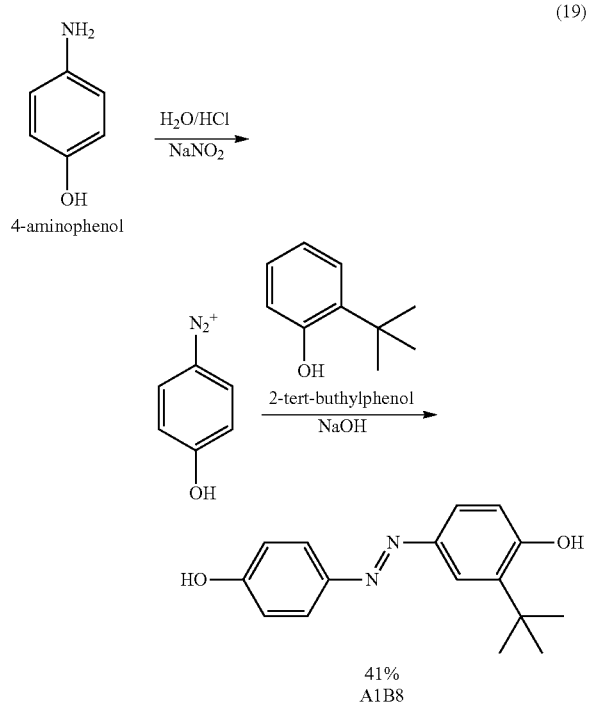

(19)

Compound A1B8 (Intermediate 8) was subjected to $^1$H NMR analysis to determine the structure.

$^1$H NMR (400 MHz, DMSO-$d_6$):
10.12 (s, 1H), 10.08 (s, 1H), 7.69-7.72 (m, 3H), 7.55 (d-d, $J_1$=8.4 Hz, $J_2$=2.3 Hz, 1H), 6.93 (d, J=8.5 Hz, 1H), 6.89 (d-d, $J_1$=6.8 Hz, $J_2$=1.9 Hz, 2H), 1.40 (s, 9H).

Example 8-2

Synthesis of Compound A1B8-C12 (Azobenzene Derivative 8)

10 mL of acetone, 1-bromododecane (0.548 g, 2.2 mmol), and potassium carbonate (1.10 g, 8 mmol) were added to Compound A1B8 (0.270 g, 1.0 mmol), and the mixture was stirred at 60° C. for 18 hours. After evaporating the solvent under reduced pressure, the resulting solid was purified by silica gel column chromatography (eluant: ethyl acetate:hexane=1:9), and recrystallized from acetone to obtain Compound A1B8-C12 (orange solid, 0.579 g, yield: 95%).

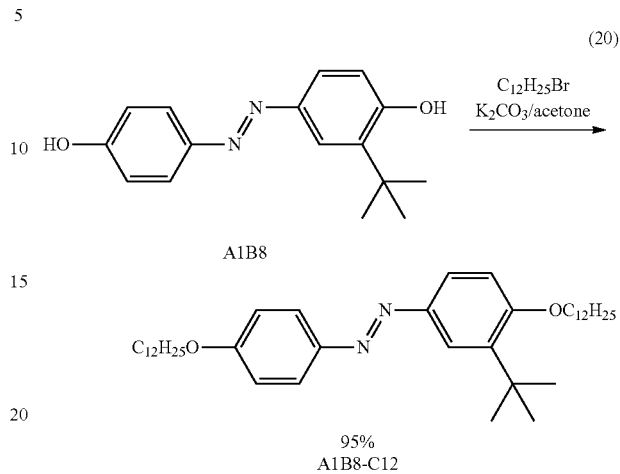

(20)

Compound A1B8-C12 was subjected to $^1$H NMR analysis and $^{13}$C NMR analysis to determine the structure.

$^1$H NMR (400 MHz, CDCl$_3$):
7.92-7.95 (m, 3H), 7.83 (d, J=8.6, 1H), 7.00 (d, J=9.0 Hz, 2H), 6.97 (d, J=8.8 Hz, 1H), 4.03-4.10 (m, 4H), 1.79-1.91 (m, 4H), 1.26-1.58 (m, 45H), 0.88-0.92 (m, 6H).

$^{13}$C NMR (100 MHz, CDCl$_3$):
161.2, 160.4, 146.6, 146.0, 138.8, 124.4, 122.2, 121.8, 114.7, 111.8, 68.4, 68.3, 35.1, 31.9, 29.7, 29.6, 29.6, 29.6, 29.5, 29.4, 29.4, 29.3, 29.2, 26.3, 26.0, 22.7, 14.1.

MS (MALDI-TOF MS): m/z 607.606 (calc. [M+H]$^+$=607.520).

Example 8-3

DSC Measurement of Compound A1B8-C12

The thermal phase transition temperature of Compound A1B8-C12 was determined by differential scanning calorimetry.
Cr 67 Iso, Iso 41 Cr

Example 8-4

Light Exposure Experiment for Compound A1B8-C12

The crystal-isotropic phase transition of Compound A1B8-C12 at 30° C. was observed using a polarizing optical microscope. The results are shown in FIG. 11.

Figure 11:
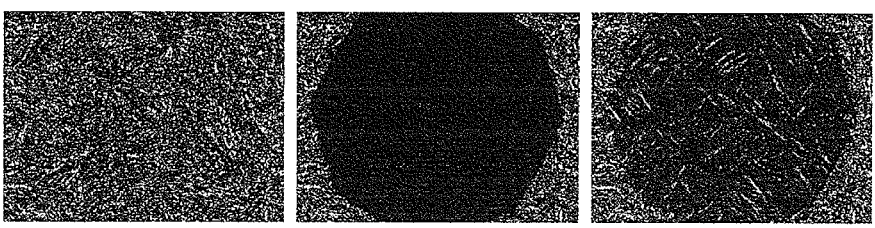
FIG. 11 represents a polarizing optical micrograph showing the crystal-isotropic phase transition of Compound A1B8-C12 at 30° C.

In FIG. 11, the left represents a polarizing optical micrograph before light exposure; the center represents a polarizing optical micrograph just after exposure to ultraviolet light (365 nm) for 413 seconds; and the right represents a polarizing optical micrograph after exposure to visible light (436 nm) for 5 seconds wherein the sample was exposed to ultraviolet light as stated above.

Example 9-1

Synthesis of Compound A1B9 (Intermediate 9)

25 mL of 2.4N hydrochloric acid was added to 4-aminophenol (2.18 g, 20 mmol). After the addition of a solution prepared by dissolving sodium nitrite (1.66 g, 24 mmol) in 2 mL of distilled water to the mixture while stirring the mixture at 0° C., the resulting mixture was stirred at 0° C. for 15 minutes. The resulting solution was added to a mixture of o-cresol (2.16 g, 20 mmol) and 8 mL of a 20% sodium hydroxide aqueous solution, and the mixture was stirred for 16 hours. The resulting solution was made acidic using hydrochloric acid under cooling, a brown precipitate was filtered off, and the resulting solid was washed with water. The resulting black solid was purified by silica gel column chromatography (eluant: ethyl acetate:hexane=1:2), and recrystallized from a mixed solvent of acetone and hexane to obtain Compound A1B9 (brown solid, 2.40 g, yield: 53%).

(21)

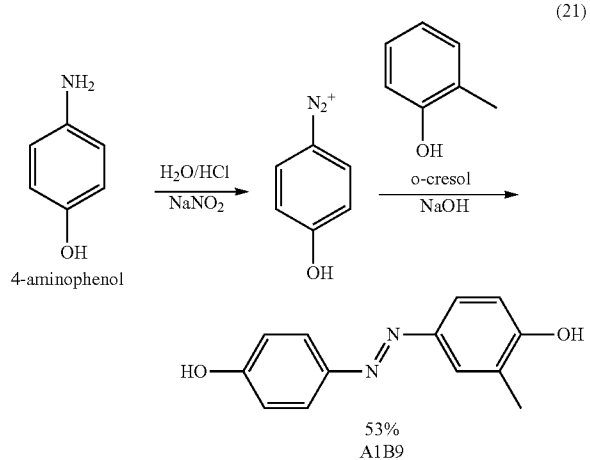

Compound A1B9 (Intermediate 9) was subjected to $^1$H NMR analysis to determine the structure.

$^1$H NMR (400 MHz, DMSO-d$_6$):

10.08 (s, 1H), 10.04 (s, 1H), 7.70 (d-d, J$_1$=6.84 Hz, J$_2$=1.9 Hz, 2H), 7.60 (d, J=2.0 Hz, 1H), 7.55 (d-d, J$_1$=8.4 Hz, J$_2$=2.4 Hz, 1H), 6.92 (d, J=8.4 Hz, 1H), 6.90 (d-d, J$_1$=6.8 Hz, J$_2$=1.9 Hz, 2H), 2.20 (s, 3H).

Example 9-2

Synthesis of Compound A1B9-C12 (Azobenzene Derivative 9)

10 mL of acetone, 1-bromododecane (0.548 g, 2.2 mmol), and potassium carbonate (1.10 g, 8 mmol) were added to Compound A1B9 (0.228 g, 1.0 mmol), and the mixture was stirred at 60° C. for 18 hours. After evaporating the solvent under reduced pressure, the resulting solid was purified by silica gel column chromatography (eluant: ethyl acetate:hexane=1:9), and recrystallized from acetone to obtain Compound A1B9-C12 (orange solid, 0.540 g, yield: 96%).

(22)

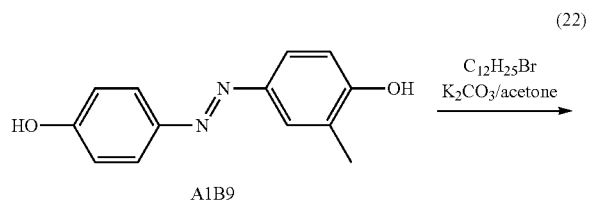

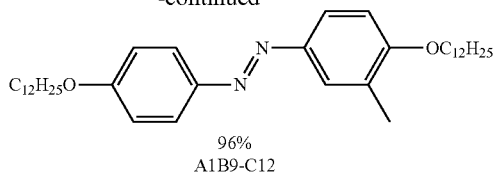

Compound A1B9-C12 was subjected to $^1$H NMR analysis and $^{13}$C NMR analysis to determine the structure.

$^1$H NMR (400 MHz, CDCl$_3$):

7.91 (d, J=9.0 Hz, 2H), 7.78-7.80 (m, 2H), 7.00 (d, J=9.0 Hz, 2H), 6.92 (d, J=8.3 Hz, 1H), 4.03-4.08 (m, 4H), 2.31 (s, 3H), 1.79-1.91 (m, 4H), 1.45-1.57 (m, 4H), 1.23-1.44 (m, 35H), 0.88-0.91 (m, 6H).

$^{13}$C NMR (100 MHz, CDCl$_3$):

161.2, 159.6, 146.8, 146.2, 127.6, 124.3, 123.6, 123.5, 114.7, 110.6, 68.4, 68.3, 31.9, 29.7, 29.6, 29.6, 29.4, 29.3, 29.3, 29.2, 26.1, 26.0, 22.7, 16.4, 14.1.

MS (MALDI-TOF MS): m/z 565.537 (calc. [M+H]$^+$=565.473).

Example 9-3

DSC Measurement of Compound A1B9-C12

The thermal phase transition temperature of Compound A1B9-C12 was determined by differential scanning calorimetry.

Cr 66 LC 72 Iso, Iso 72 LC 53 Cr

Example 9-4

Light Exposure Experiment for Compound A1B9-C12

The crystal-isotropic phase transition of Compound A1B9-C12 at 27° C. was observed using a polarizing optical microscope. The results are shown in FIG. 12.

Figure 12:
FIG. 12 represents a polarizing optical micrograph showing the crystal-isotropic phase transition of Compound A1B9-C12 at 27° C.

In FIG. 12, the left represents a polarizing optical micrograph before light exposure; the center represents a polarizing optical micrograph just after exposure to ultraviolet light (365 nm) for 270 seconds; and the right represents a polarizing optical micrograph after exposure to visible light (436 nm) for 2 seconds wherein the sample was exposed to ultraviolet light as stated above.

Example 9-5

Measurement of Dynamic Viscoelasticity of Compound A1B9-C12 During Light Exposure The dynamic viscoelasticity of Compound A1B9-C12 along with exposure to ultraviolet light (365 nm) was measured using an MCR rheometer (manufactured by Anton-Paar).

Figure 13:
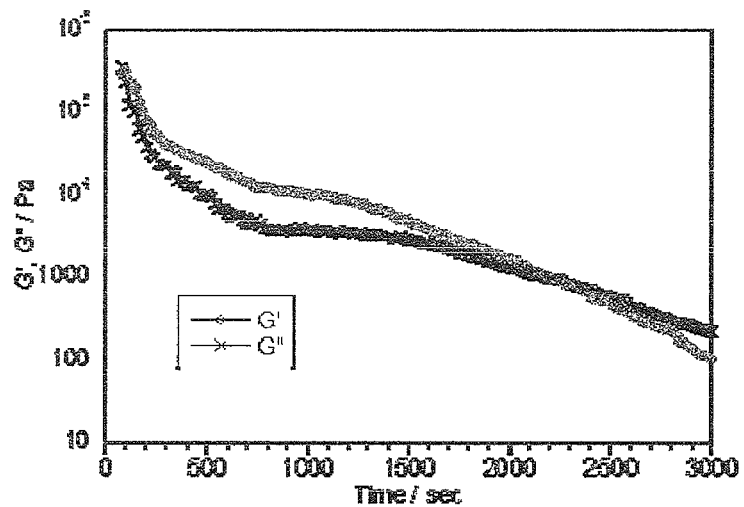
FIG. 13 represents a result of the dynamic viscoelasticity measurement results for Compound A1B9-C12 during light exposure.

In FIG. 13, the storage modulus (G') and the loss modulus (G") are plotted with respect to the light exposure time. As shown in FIG. 13, the modulus of elasticity decreased along with light exposure, and the relationship between the storage modulus (G') and the loss modulus (G") reversed. This suggests that Compound A1B9-C12 was melted due to light, and became liquid.

Example 10-1

Synthesis of Compound A1B9-C6 (Azobenzene Derivative 10)

10 mL of DMF, 1-bromohexane (0.99 g, 6 mmol), and potassium carbonate (0.69 g, 5 mmol) were added to Compound A1B9 (Intermediate 9) (0.228 g, 1.0 mmol), and the mixture was stirred at 80° C. for 2 hours, and then stirred at room temperature for 16 hours. The solvent was evaporated under reduced pressure, followed by extraction with ethyl acetate. The organic layer was washed with a saturated sodium chloride solution, dried over anhydrous magnesium sulfate, and filtered. After evaporating the solvent under reduced pressure, the resulting solid was purified by silica gel column chromatography (eluant: ethyl acetate:hexane=2:98) to obtain Compound A1B9-C6 (orange solid, 0.304 g, yield: 77%).

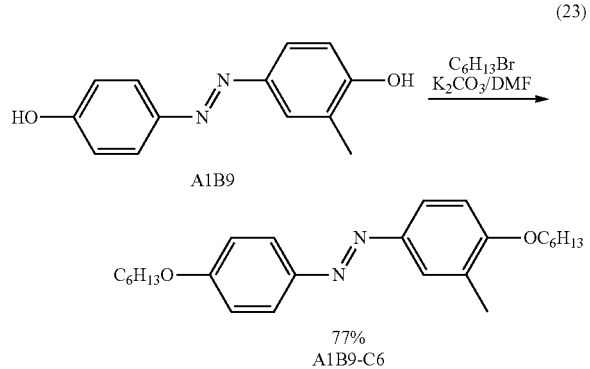

(23)

Compound A1B9-C6 was subjected to $^1$H NMR analysis and $^{13}$C NMR analysis to determine the structure.

$^1$H NMR (400 MHz, CDCl$_3$):
7.84 (d-d, J$_1$=6.9 Hz, J$_2$=2.1 Hz, 2H), 7.71-7.74 (m, 2H), 6.96 (d-d, J$_1$=6.9 Hz, J$_2$=2.1 Hz, 2H), 6.88 (d, J=9.3 Hz, 1H), 3.99-4.04 (m, 4H), 2.27 (s, 3H), 1.75-1.85 (m, 4H), 1.44-1.50 (m, 4H), 1.31-1.36 (m, 8H), 0.88-0.93 (m, 6H).

$^{13}$C NMR (100 MHz, CDCl$_3$):
161.2, 159.6, 146.7, 146.1, 127.6, 124.3, 123.6, 123.5, 114.7, 110.6, 68.3, 68.3, 31.6, 31.6, 29.2, 29.2, 25.8, 25.7, 22.6, 16.4, 14.0.

MS (MALDI-TOF MS): m/z 397.276 (calc. [M+H]$^+$=397.286).

Example 10-2

DSC Measurement of Compound A1B9-C6

The thermal phase transition temperature of Compound A1B9-C6 was determined by differential scanning calorimetry.
Cr 87 Iso, Iso 78 Cr Example 10-3

Light Exposure Experiment for Compound A1B9-C6

The crystal-isotropic phase transition of Compound A1B9-C6 at 23° C. was observed using a polarizing optical microscope. The results are shown in FIG. 14.

Figure 14:
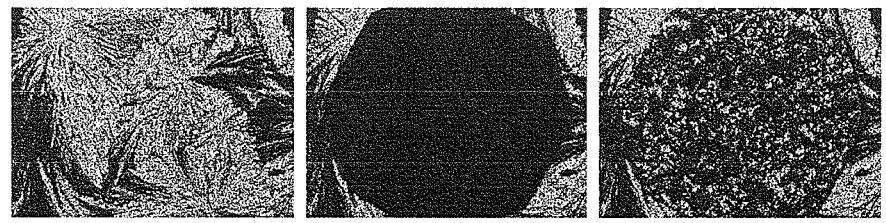
FIG. 14 represents a polarizing optical micrograph showing the crystal-isotropic phase transition of Compound A1B9-C6 at 23° C.

In FIG. 14, the left represents a polarizing optical micrograph before light exposure; the center represents a polarizing optical micrograph just after applying ultraviolet light (365 nm) for 4 seconds; and the right represents a polarizing optical micrograph after exposure to visible light (436 nm) for 1 second wherein the sample was exposed to ultraviolet light as stated above.

Example 11-1

Synthesis of Compound A1B9-C18 (Azobenzene Derivative 11)

5.5 mL of DMF, 1-bromooctadecane (2.2 g, 6.6 mmol), and potassium carbonate (1.52 g, 11 mmol) were added to Compound A1B9 (Intermediate 9) (0.228 g, 1.0 mmol), and the mixture was stirred at 80° C. for 2 hours, and then stirred at room temperature for 16 hours. The solvent was evaporated under reduced pressure, followed by extraction with ethyl acetate. The organic layer was washed with a saturated sodium chloride solution, dried over anhydrous magnesium sulfate, and filtered. After evaporating the solvent under reduced pressure, the resulting solid was purified by silica gel column chromatography (eluant: chloroform:hexane=2:8) to obtain Compound A1B9-C18 (light yellow solid, 0.56 g, yield: 76%).

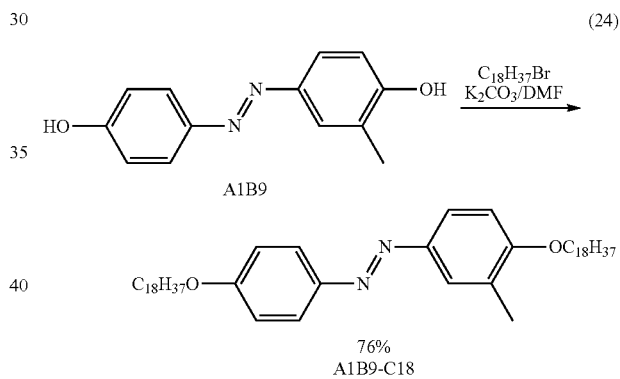

(24)

Compound A1B9-C18 was subjected to $^1$H NMR analysis and $^{13}$C NMR analysis to determine the structure.

$^1$H NMR (400 MHz, CDCl$_3$):
7.89 (d, J=9.0 Hz, 2H), 7.76-7.78 (m, 2H), 6.97 (d, J=9.0 Hz, 2H), 6.89 (d, J=8.4 Hz, 1H), 3.99-4.04 (m, 4H), 2.27 (s, 3H), 1.77-1.83 (m, 4H), 1.42-1.51 (m, 4H), 1.23-1.38 (m, 56H), 0.84-0.88 (m, 6H).

$^{13}$C NMR (100 MHz, CDCl$_3$):
161.3, 159.7, 146.6, 146.0, 127.6, 124.4, 123.7, 123.6, 114.7, 110.6, 68.4, 68.3, 31.9, 29.7, 29.7, 29.6, 29.4, 29.3, 29.2, 26.1, 26.0, 22.7, 16.4, 14.1.

MS (MALDI-TOF MS): m/z 733.840 (calc. [M+H]$^+$=733.661).

Example 11-2

DSC Measurement of Compound A1B9-C18

The thermal phase transition temperature of Compound A1B9-C18 was determined by differential scanning calorimetry.
Cr 84 Iso, Iso 70 Cr 68 Cr

Example 11-3

Light Exposure Experiment for Compound A1B9-C18

The crystal-isotropic phase transition of Compound A1B9-C18 at 25° C. was observed using a polarizing optical microscope. The results are shown in FIG. 15.

Figure 15:
FIG. 15 represents a polarizing optical micrograph showing the crystal-isotropic phase transition of Compound A1B9-C18 at 25° C.

In FIG. 15, the left represents a polarizing optical micrograph before light exposure; the center represents a polarizing optical micrograph just after exposure to ultraviolet light (365 nm) for 30 minutes; and the right represents a polarizing optical micrograph after exposure to visible light (436 nm) for 50 seconds wherein the sample was exposed to ultraviolet light as stated above.

Example 12-1

Synthesis of Compound A3B1 (Intermediate 10)

25 mL of 2.4N hydrochloric acid was added to 4-amino-m-cresol (2.46 g, 20 mmol). After the addition of a solution prepared by dissolving sodium nitrite (1.66 g, 24 mmol) in 2 mL of distilled water to the mixture while stirring the mixture at −6° C., the resulting mixture was stirred for 15 minutes. The resulting solution was added to a mixture (cooled to 0° C.) of 3,5-dimethylphenol (2.44 g, 20 mmol) and 8 mL of a 20% sodium hydroxide aqueous solution, and the mixture was stirred at room temperature for 16 hours. The resulting solution was made acidic using hydrochloric acid under cooling, and extracted with ethyl acetate. The organic layer was washed with a saturated sodium chloride solution, dried over anhydrous magnesium sulfate, and filtered. After evaporating the solvent under reduced pressure, the resulting solid was purified by silica gel column chromatography (eluant: ethyl acetate:hexane=1:2) to obtain Compound A3B1 (brown solid, 1.32 g, yield: 26%).

(25)

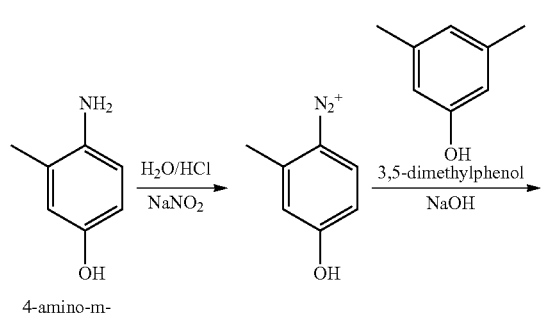

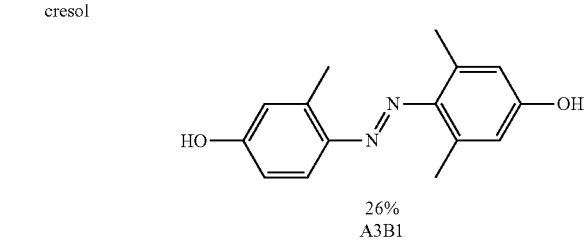

Compound A3B1 (Intermediate 10) was subjected to $^1$H NMR analysis to determine the structure.

$^1$H NMR (400 MHz, DMSO-d$_6$):
9.90 (s, 1H), 9.72 (s, 1H), 7.48 (d, J=8.8 Hz, 1H), 6.75 (d, J=2.4 Hz, 1H), 6.68 (d-d, J$_1$=8.8 Hz, J$_2$=2.4 Hz, 1H), 6.56 (s, 2H), 2.53 (s, 3H), 2.38 (s, 6H).

Example 12-2

Synthesis of Compound A3B1-C12 (Azobenzene Derivative 12)

10 mL of acetone, 1-bromododecane (0.548 g, 2.2 mmol), and potassium carbonate (1.10 g, 8 mmol) were added to Compound A3B1 (0.256 g, 1.0 mmol), and the mixture was stirred at 75° C. for 12 hours. After evaporating the solvent under reduced pressure, the resulting solid was purified by silica gel column chromatography (eluant: ethyl acetate:hexane=1:9), and recrystallized from acetone to obtain Compound A3B1-C12 (orange solid, 0.488 g, yield: 82%).

(26)

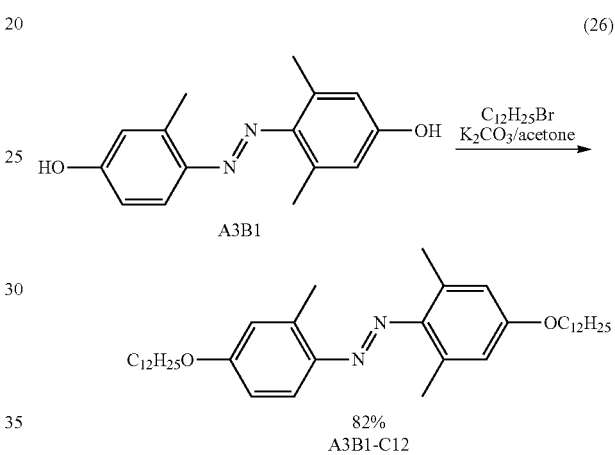

Compound A3B1-C12 was subjected to $^1$H NMR analysis and $^{13}$C NMR analysis to determine the structure.

$^1$H NMR (400 MHz, CDCl$_3$):
7.64 (d, J=8.9 Hz, 1H), 6.8 (d, J=2.8 Hz, 1H), 6.76 (d-d, J$_1$=8.9 Hz, J$_2$=2.8 Hz, 1H), 6.63 (s, 1H), 3.95-4.01 (m, 4H), 2.64 (s, 3H), 2.46 (s, 6H), 1.73-1.82 (m, 4H), 1.24-1.44 (m, 36H), 0.84-0.88 (m, 6H).

$^{13}$C NMR (100 MHz, CDCl$_3$):
161.1, 158.8, 145.7, 144.3, 140.1, 134.5, 116.5, 115.9, 115.0, 112.8, 68.2, 68.0, 31.9, 29.7, 29.6, 29.4, 29.3, 29.3, 29.2, 26.0, 22.7, 20.5, 18.3, 14.1.

MS (MALDI-TOF MS): m/z 593.570 (calc. [M+H]$^+$=593.505).

Example 12-3

DSC measurement of Compound A3B1-C12

The thermal phase transition temperature of Compound A3B1-C12 was determined by differential scanning calorimetry.
Cr 70 Iso, Iso 64 Cr

Example 12-4

Light Exposure Experiment for Compound A3B1-C12

Figure 16:
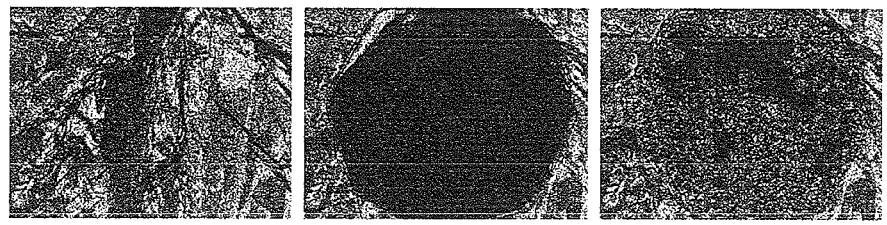
FIG. 16 represents a polarizing optical micrograph showing the crystal-isotropic phase transition of Compound A3B1-C12 at 42° C.

The crystal-isotropic phase transition of Compound A3B1-C12 at 42° C. was observed using a polarizing optical microscope. The results are shown in FIG. 16.

Example 13-1

Synthesis of Compound A3B2 (Intermediate 11)

25 mL of 2.4N hydrochloric acid was added to 4-amino-m-cresol (2.46 g, 20 mmol). After the addition of a solution prepared by dissolving sodium nitrite (1.66 g, 24 mmol) in 2 mL of distilled water to the mixture while stirring the mixture at −6° C., the resulting mixture was stirred for 15 minutes. The resulting solution was added to a mixture (cooled to 0° C.) of 6-isopropyl-m-cresol (3.00 g, 20 mmol) and 8 mL of a 20% sodium hydroxide aqueous solution, and the mixture was stirred at room temperature for 16 hours. The resulting solution was made acidic using hydrochloric acid under cooling, and extracted with ethyl acetate. The organic layer was washed with a saturated sodium chloride solution, dried over anhydrous magnesium sulfate, and filtered. After evaporating the solvent under reduced pressure, the resulting solid was purified by silica gel column chromatography (eluant: ethyl acetate:hexane=1:2) to obtain Compound A3B2 (brown solid, 2.30 g, yield: 40%).

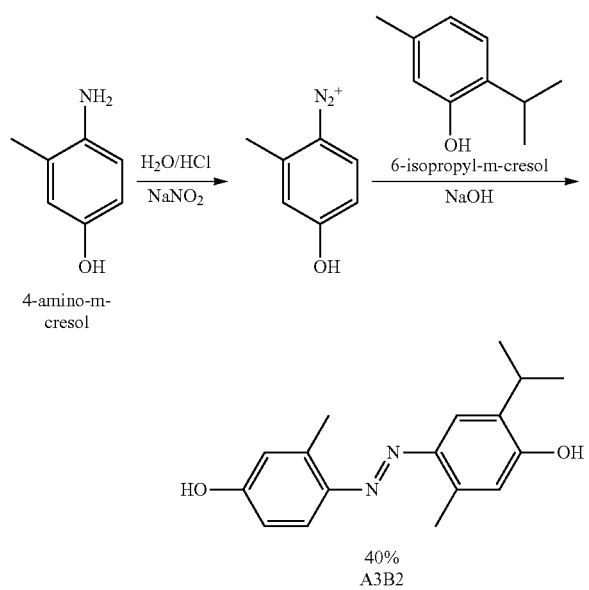

(27)

Compound A3B2 (Intermediate 11) was subjected to $^1$H NMR analysis to determine the structure.

$^1$H NMR (400 MHz, DMSO-$d_6$):

9.89 (s, 1H), 9.88 (s, 1H), 7.50 (d, J=8.7 Hz, 1H), 7.48 (s, 1H), 6.74 (s, 1H), 6.74 (d, J=2.7 Hz, 1H), 6.67 (d-d, $J_1$=8.8 Hz, $J_2$=2.7 Hz, 1H), 3.15 (septet, J=6.9 Hz, 1H), 2.59 (s, 3H), 2.54 (s, 3H), 1.17 (d, J=6.9 Hz, 6H).

Example 13-2

Synthesis of Compound A3B2-C12 (Azobenzene Derivative 13)

10 mL of acetone, 1-bromododecane (0.548 g, 2.2 mmol), and potassium carbonate (1.10 g, 8 mmol) were added to Compound A3B2 (0.284 g, 1.0 mmol), and the mixture was stirred at 75° C. for 12 hours. After evaporating the solvent under reduced pressure, the resulting solid was purified by silica gel column chromatography (eluant: ethyl acetate:hexane=1:9), and recrystallized from acetone to obtain Compound A3B2-C12 (orange solid, 0.507 g, yield: 82%).

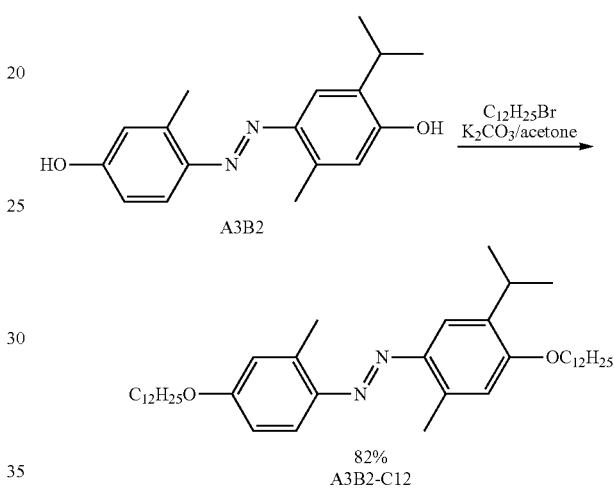

(28)

Compound A3B2-C12 was subjected to $^1$H NMR analysis and $^{13}$C NMR analysis to determine the structure.

$^1$H NMR (400 MHz, CDCl$_3$):

7.72 (d, J=9.0 Hz, 1H), 7.70 (s, 1H), 6.83 (d, J=2.4 Hz, 1H), 6.79 (d-d, $J_1$=8.9 Hz, $J_2$=2.7 Hz, 1H), 6.74 (s, 1H), 4.01-4.06 (m, 4H), 3.30 (septet, J=6.8 Hz, 1H), 2.73 (s, 3H), 2.71 (s, 3H), 1.78-1.88 (m, 4H), 1.45-1.57 (m, 4H), 1.23-1.44 (m, 28H), 0.88-0.92 (m, 6H).

$^{13}$C NMR (100 MHz, CDCl$_3$):

160.7, 158.6, 145.3, 144.7, 139.6, 137.2, 135.3, 117.6, 116.0, 114.3, 112.8, 112.7, 68.2, 68.1, 31.9, 29.7, 29.6, 29.6, 29.6, 29.4, 29.3, 29.3, 27.1, 26.2, 26.0, 22.7, 22.5, 18.0, 17.6, 14.1.

MS (MALDI-TOF MS): m/z 621.637 (calc. [M+H]$^+$=621.536).

Example 13-3

DSC Measurement of Compound A3B2-C12

The thermal phase transition temperature of Compound A3B2-C12 was determined by differential scanning calorimetry.

Cr1Cr2 60 Cr2 68 Iso, Iso 45 Cr1Cr2

Crystal polymorphs were present. Two types of crystals (Cr1 and Cr2) were melted at different temperatures during heating, and precipitated as mixed crystals during cooling.

Example 13-4

Light Exposure Experiment for Compound A3B2-C12

The crystal-isotropic phase transition of Compound A3B2-C12 at 26° C. was observed using a polarizing optical microscope. The results are shown in FIG. 17.

Figure 17:
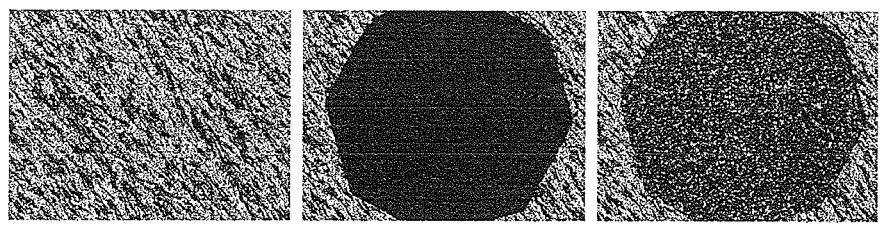
FIG. 17 represents a polarizing optical micrograph showing the crystal-isotropic phase transition of Compound A3B2-C12 at 26° C.

In FIG. 17, the left represents a polarizing optical micrograph before light exposure; the center represents a polarizing optical micrograph just after exposure to ultraviolet light (365 nm) for 221 seconds; and the right represents a polarizing optical micrograph after exposure to visible light (436 nm) for 2 seconds wherein the sample was exposed to ultraviolet light as stated above.

Example 13-4

Absorption Spectrum Measurement of Solution of Compound A3B2-C12

Compound A3B2-C12 was dissolved in chloroform, and the visible-ultraviolet absorption spectrum was measured at room temperature before and after light exposure.

Figure 18:
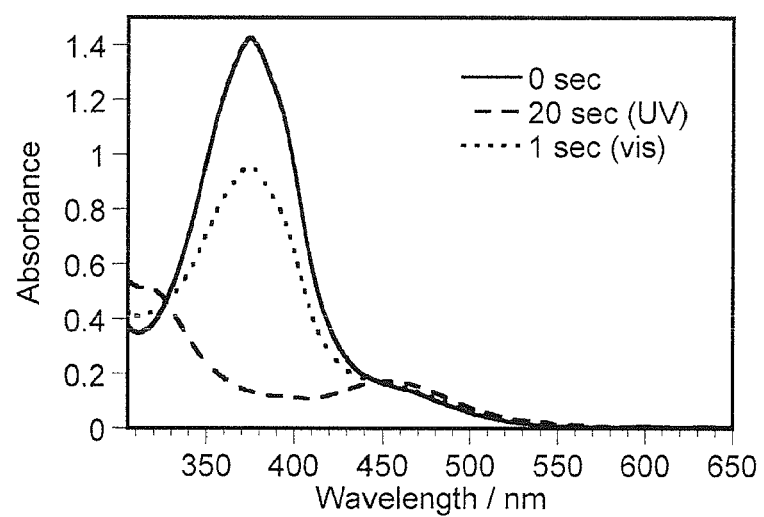
FIG. 18 represents the absorption spectrum of a chloroform solution of Compound A3B2-C12 measured at 23° C.

FIG. 18 shows the absorption spectrum of the chloroform solution of Compound A3B2-C12 measured at 23° C. In FIG. 18, "0 sec" represents the spectrum before light exposure; "20 sec (UV)" represents the spectrum after exposure to ultraviolet light (365 nm) for 20 seconds; and "1 sec (vis)" represents the spectrum after exposure to visible light (465 nm) for 1 second wherein the sample was exposed to ultraviolet light (365 nm) as stated above.

The change in spectrum shown in FIG. 18 suggests that Compound A3B2-C12 underwent trans-to-cis photoisomerization in the solution by exposure to ultraviolet light, and then underwent cis-to-trans photoisomerization by exposure to visible light.

Example 13-5

Absorption Spectrum Measurement of Thin Film of Compound A3B2-C12

Compound A3B2-C12 was enclosed in a glass sandwich cell, and the visible-ultraviolet absorption spectrum was measured at room temperature before and after light exposure.

Figure 19:
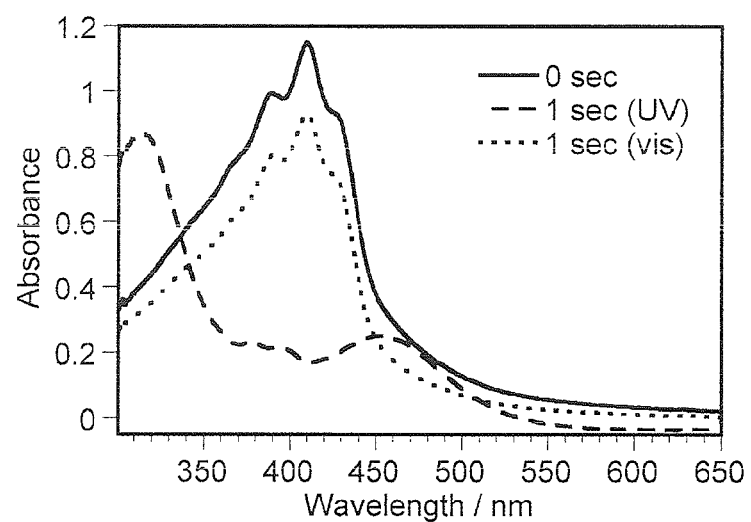
FIG. 19 represents the absorption spectrum of a thin film of Compound A3B2-C12 measured at 23° C.

FIG. 19 shows the absorption spectrum of a thin film of Compound A3B2-C12 measured at 23° C. In FIG. 19, "0 sec" represents the spectrum before light exposure; "1 sec (UV)" represents the spectrum after exposure to ultraviolet light (365 nm) for 1 second; and "1 sec (vis)" represents the spectrum after exposure to visible light (465 nm) for 1 second wherein the sample was exposed to ultraviolet light (365 nm) as stated above.

The change in spectrum shown in FIG. 19 suggests that Compound A3B2-C12 (crystal state) underwent trans-to-cis photoisomerization at room temperature by exposure to ultraviolet light, and then underwent cis-to-trans photoisomerization by exposure to visible light.

Example 14-1

Synthesis of Compound A3B3 (Intermediate 12)

25 mL of 2.4N hydrochloric acid was added to 4-amino-m-cresol (2.46 g, 20 mmol). After the addition of a solution prepared by dissolving sodium nitrite (1.66 g, 24 mmol) in 2 mL of distilled water to the mixture while stirring the mixture at −6° C., the resulting mixture was stirred for 15 minutes. The resulting solution was added to a mixture (cooled to 0° C.) of 2-methyl-5-isopropylphenol (3.00 g, 20 mmol) and 8 mL of a 20% sodium hydroxide aqueous solution, and the mixture was stirred at room temperature for 16 hours. The resulting solution was made acidic using hydrochloric acid under cooling, and extracted with ethyl acetate. The organic layer was washed with a saturated sodium chloride solution, dried over anhydrous magnesium sulfate, and filtered. After evaporating the solvent under reduced pressure, the resulting solid was purified by silica gel column chromatography (eluant: ethyl acetate:hexane=1:2) to obtain Compound A3B3 (brown solid, 1.29 g, yield: 23%).

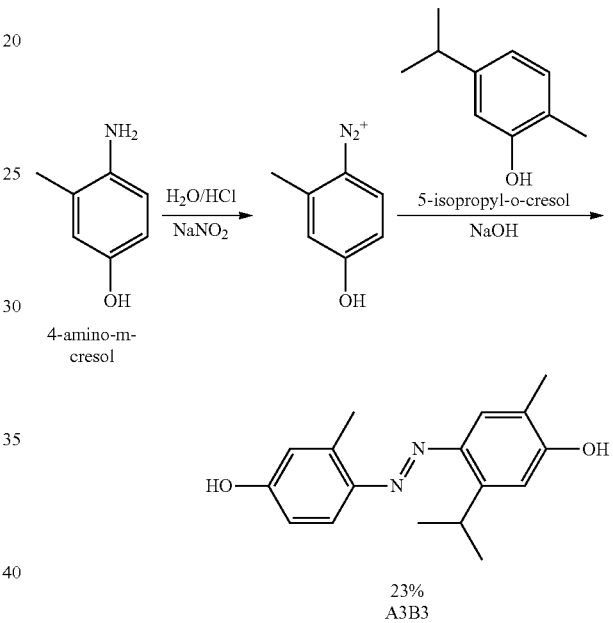

(29)

Compound A3B3 (Intermediate 12) was subjected to $^1$H NMR analysis to determine the structure.

$^1$H NMR (400 MHz, DMSO-d$_6$):

9.90 (s, 1H), 9.86 (s, 1H), 7.47 (d, J=8.8 Hz, 1H), 7.39 (s, 1H), 6.83 (s, 1H), 6.74 (d, J=2.4 Hz, 1H), 6.68 (d-d, J$_1$=8.7 Hz, J$_2$=2.6 Hz, 1H), 4.01 (septet, J=6.9 Hz, 1H), 2.60 (s, 3H), 2.12 (s, 3H), 1.24 (d, J=6.9 Hz, 6H).

Example 14-2

Synthesis of Compound A3B3-C12 (Azobenzene Derivative 14)

10 mL of acetone, 1-bromododecane (0.548 g, 2.2 mmol), and potassium carbonate (1.10 g, 8 mmol) were added to Compound A3B3 (0.284 g, 1.0 mmol), and the mixture was stirred at 75° C. for 5 hours. After evaporating the solvent under reduced pressure, the resulting solid was purified by silica gel column chromatography (eluant: ethyl acetate:hexane=1:9), and recrystallized from acetone to obtain Compound A3B3-C12 (orange solid, 0.140 g, yield: 23%).

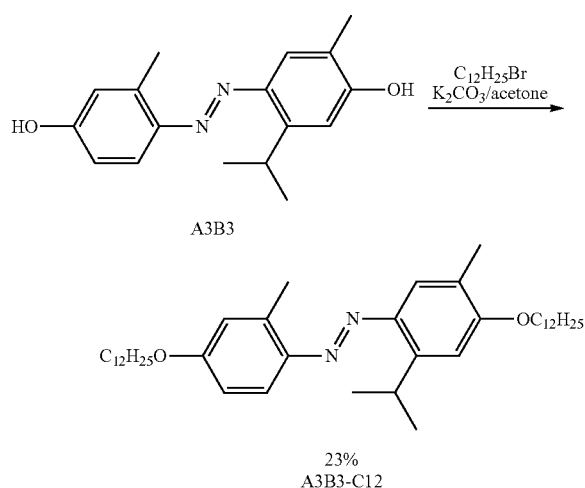

(30)

A3B3

23%
A3B3-C12

Compound A3B3-C12 was subjected to $^1$H NMR analysis and $^{13}$C NMR analysis to determine the structure.

$^1$H NMR (400 MHz, CDCl$_3$):

7.62 (d, J=8.8 Hz, 1H), 7.52 (s, 1H), 6.80 (d, J=2.6 Hz, 1H), 6.78 (s, 1H), 6.75 (d-d, J$_1$=8.8 Hz, J$_2$=2.6 Hz, 1H), 4.16 (septet, J=7.0 Hz, 1H), 4.03 (t, J=6.4 Hz, 2H), 3.98 (t, J=6.6 Hz, 2H), 2.70 (s, 3H), 2.21 (s, 3H), 1.75-1.83 (m, 4H), 1.30-1.58 (m, 42H), 0.85-0.88 (m, 6H).

$^{13}$C NMR (100 MHz, CDCl$_3$):

160.7, 159.9, 147.8, 145.3, 143.2, 139.6, 124.9, 117.9, 117.5, 115.9, 112.8, 107.6, 68.2, 68.1, 31.9, 29.7, 29.6, 29.6, 29.4, 29.3, 29.3, 29.3, 27.6, 26.1, 26.0, 24.0, 22.7, 18.0, 16.0, 14.1.

MS (MALDI-TOF MS): m/z 621.634 (calc. [M+H]$^+$=621.536).

Example 14-3

DSC Measurement of Compound A3B3-C12

The thermal phase transition temperature of Compound A3B3-C12 was determined by differential scanning calorimetry.

Cr1Cr2Cr3 61 Cr2Cr3 65 Cr3 70 Iso, Iso 46 Cr1Cr2Cr3

Crystal polymorphs were present. Three types of crystals (Cr1, Cr2, and Cr3) were melted at different temperatures during heating, and precipitated as mixed crystals during cooling.

Example 14-4

Light Exposure Experiment for Compound A3B3-C12

The crystal-isotropic phase transition of Compound A3B3-C12 at 40° C. was observed using a polarizing optical microscope. The results are shown in FIG. 20.

Figure 20:
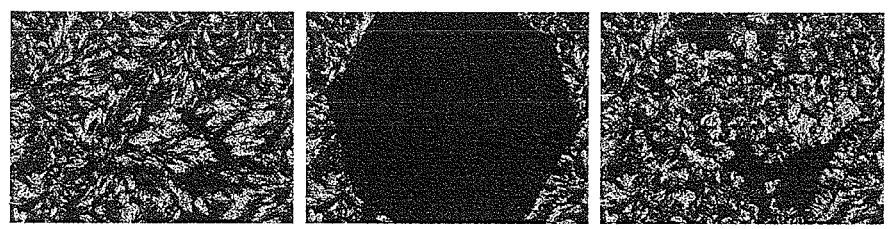
FIG. 20 represents a polarizing optical micrograph showing the crystal-isotropic phase transition of Compound A3B3-C12 at 40° C.

In FIG. 20, the left represents a polarizing optical micrograph before light exposure; the center represents a polarizing optical micrograph just after exposure to ultraviolet light (365 nm) for 60 seconds; and the right represents a polarizing optical micrograph after exposure to visible light (436 nm) for 600 seconds wherein the sample was exposed to ultraviolet light as stated above.

Example 15-1

Synthesis of Intermediate (Intermediate 13) of Compound A3B4-C12

50 mL of N,N-dimethylformamide, 1-bromododecane (11.1 g, 45 mmol), and potassium carbonate (10.4 g, 75 mmol) were added to 3-methyl-4-nitrophenol (2.27 g, 15 mmol). The mixture was heated to 80° C. and stirred for 23 hours. After confirming disappearance of 3-methyl-4-nitrophenol by thin-layer chromatography (TLC), the mixture was allowed to cool at room temperature, and distilled water was poured into the mixture, following by extraction with n-hexane. The organic phase was washed once with distilled water, and washed once with a saturated sodium chloride aqueous solution.

The organic phase was dried over anhydrous magnesium sulfate. After removing a solid by filtration, the solvent was evaporated under reduced pressure. The resulting oil-like residue was purified by silica gel column chromatography (eluant: hexane:chloroform=7:3) to obtain Intermediate 13 (light yellow liquid, 4.58 g, yield: 92.9%).

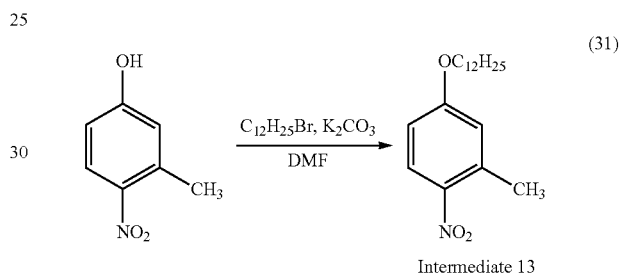

(31)

Intermediate 13

Intermediate 13 was subjected to $^1$H NMR analysis and $^{13}$C NMR analysis to determine the structure.

TLC: Rf=0.62 (CHCl$_3$-Hexane, 1:1), $^1$H NMR (400 MHz, CDCl$_3$): d 8.10 (d, J=7.4 Hz, 1H), 6.79-6.82 (m, 2H), 4.04 (t, J=6.5 Hz, 2H), 2.65 (s, 3H), 1.82 (m, 2H), 1.24-1.50 (m, 18H), 0.90 (t, J=6.7 Hz, 3H)

Example 15-2

Synthesis of Compound A3B4-C12 (Azobenzene Derivative 15)

Intermediate 13 (643 mg, 2.0 mmol) was dissolved in 20 mL of anhydrous tetrahydrofuran (THF). 5.0 mL of an anhydrous THF solution of lithium aluminum hydride (1.0 mol/L) was added to the solution at room temperature over about 5 minutes, and the mixture was stirred at room temperature for 1.5 hours. After addition of 50 mL of distilled water to the reaction mixture, most of the THF was evaporated under reduced pressure. The resulting residue was extracted with hexane. The combined organic phase was washed once with distilled water, and washed once with a saturated sodium chloride aqueous solution.

The organic phase was dried over anhydrous magnesium sulfate. After removing a solid by filtration, the solvent was evaporated under reduced pressure. The resulting orange solid was purified by silica gel column chromatography (eluant: hexane:chloroform=3:1) to obtain Compound A3B4-C12 (orange solid, 130 mg, yield: 22.5%).

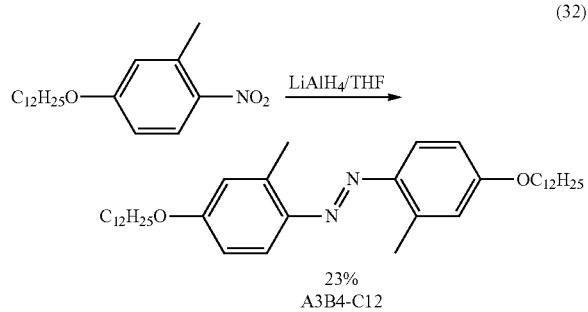

(32)

Compound A3B4-C12 was subjected to $^1$H NMR analysis and $^{13}$C NMR analysis to determine the structure.

TLC: Rf=0.48 (CHCl$_3$-Hexane, 1:3), $^1$H NMR (400 MHz, CDCl$_3$):

7.65 (d, J=8.9 Hz, 2H), 6.81 (d, J=2.7, 2H), 6.76 (dd, J$_1$=8.9 Hz, J$_2$=2.8 Hz, 2H), 4.00 (t, J=6.6 Hz, 4H), 2.70 (s, 6H), 1.76-1.83 (m, 4H), 1.43-1.48 (m, 4H), 1.27-1.35 (m, 32H), 0.88 (t, J=6.7 Hz, 6H);

$^{13}$C NMR (100 MHz, CDCl$_3$):

160.8, 145.5, 139.8, 117.2, 115.9, 112.8, 68.2, 31.9, 29.7, 29.6, 29.6, 29.6, 29.4, 29.3, 29.3, 26.0, 22.7, 17.9, 14.1.

MS (MALDI-TOF MS): m/z 579.660 (calc. [M+H]$^+$=579.489).

Example 15-3

DSC Measurement of Compound A3B4-C12

The thermal phase transition temperature of Compound A3B4-C12 was determined by differential scanning calorimetry.
Cr 95 Iso, Iso 89 Cr Example 15-4

Light Exposure Experiment 1 for Compound A3B4-C12

The crystal-isotropic phase transition of Compound A3B4-C12 at 70° C. was observed using an optical microscope. The results are shown in FIG. 21.

Figure 21:
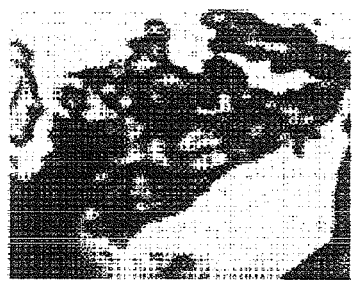
FIG. 21 represents an optical micrograph showing the crystal-isotropic phase transition of Compound A3B4-C12 at 70° C.
Figure 21:
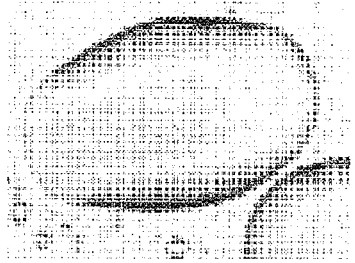
Figure 21:
Figure 21:
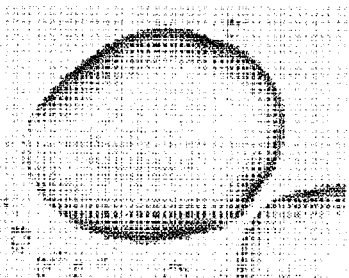

In FIG. 21, (a) represents an optical micrograph showing a crystal phase at 70° C.; (b) represents an optical micrograph showing a state after exposure to ultraviolet light (365 nm) at 70° C.; (c) represents an optical micrograph showing a state where the sample is exposed to visible light (490 nm) at 70° C. after exposure to ultraviolet light; and (d) represents an optical micrograph showing a state where the sample is second exposed to ultraviolet light at 70° C. after exposure to visible light.

Example 15-5

Light Exposure Experiment 2 for Compound A3B4-C12

The crystal-isotropic phase transition of Compound A3B4-C12 at 70° C. was observed using a polarizing optical microscope. The results are shown in FIG. 22.

Figure 22:
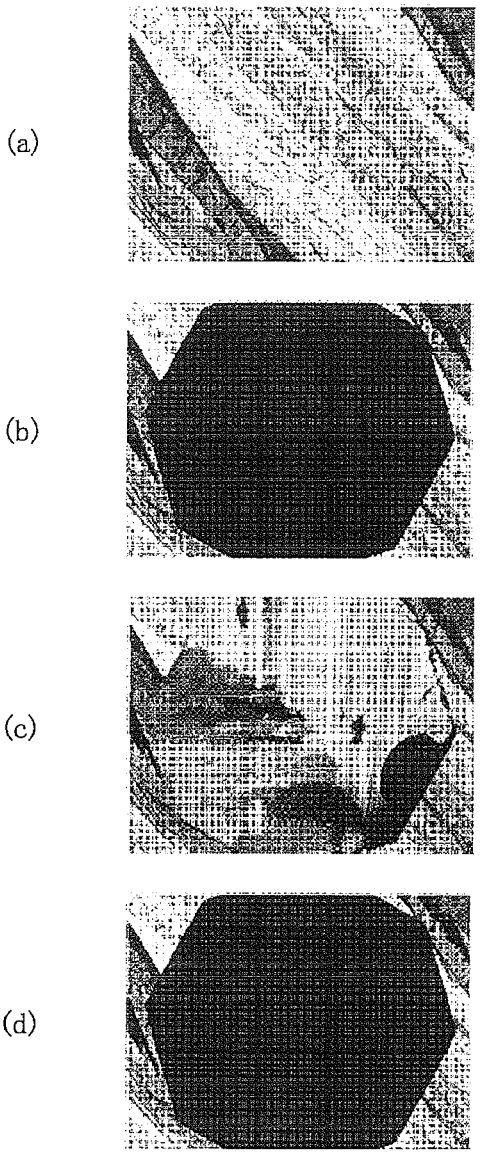
FIG. 22 represents a polarizing optical micrograph showing the crystal-isotropic phase transition of Compound A3B4-C12 at 70° C.

In FIG. 22, (a) represents a polarizing optical micrograph showing a crystal phase at 70° C.; (b) represents a polarizing optical micrograph showing a state where the sample is exposed to ultraviolet light (365 nm) at 70° C.; (c) represents a polarizing optical micrograph showing a state where the sample is exposed to visible light (490 nm) at 70° C. after exposure to ultraviolet light; and (d) represents a polarizing optical micrograph showing a state where the sample is second exposed to ultraviolet light at 70° C. after exposure to visible light.

Example 15-6

Light Exposure Experiment 3 for Compound A3B4-C12

The crystal-isotropic phase transition of Compound A3B4-C12 at 61° C. was observed using a polarizing optical microscope. The results are shown in FIG. 23.

Figure 23:
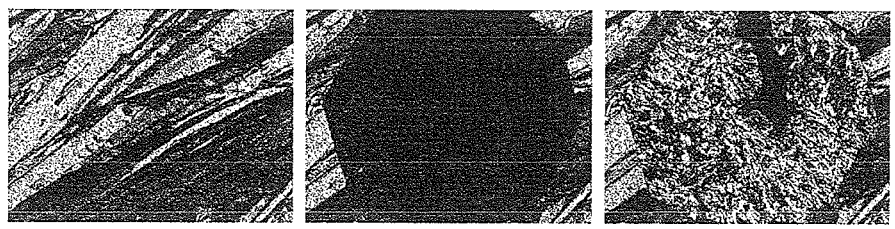
FIG. 23 represents a polarizing optical micrograph showing the crystal-isotropic phase transition of Compound A3B4-C12 at 61° C.

In FIG. 23, the left represents a polarizing optical micrograph before light exposure; the center represents a polarizing optical micrograph just after exposure to ultraviolet light (365 nm) for 840 seconds; and the right represents a polarizing optical micrograph after exposure to visible light (436 nm) for 2 seconds wherein the sample was exposed to ultraviolet light as stated above.

Example 16-1

Synthesis of Compound A3B5 (Intermediate 14)

125 mL of 2.4N hydrochloric acid was added to 4-amino-m-cresol (12.3 g, 100 mmol). After the addition of a solution (cooled to −7° C.) prepared by dissolving sodium nitrite (8.28 g, 120 mmol) in 10 mL of distilled water to the mixture while stirring the mixture at −7° C., the resulting mixture was stirred for 15 minutes. The resulting solution was added to a mixture (cooled to −7° C.) of 6-tert-butyl-o-cresol (16.4 g, 100 mmol), 40 mL of a 20% sodium hydroxide aqueous solution, and 10 mL of methanol. The mixture was stirred at −7° C. for 1 hour, and then stirred at room temperature for 16 hours. The resulting solution was extracted with chloroform in an alkaline state. After adjusting the pH of the alkaline aqueous layer to 5, the aqueous layer was extracted with ethyl acetate. The organic layer was washed with a saturated sodium chloride solution, dried over anhydrous magnesium sulfate, and filtered. After evaporating the solvent under reduced pressure, the resulting solid was purified by silica gel column chromatography (eluant: ethyl acetate:hexane=1:2), and recrystallized from an ethyl acetate/hexane mixed solvent to obtain Compound A3B5 (brown solid, 8.25 g, yield: 28%).

(33)

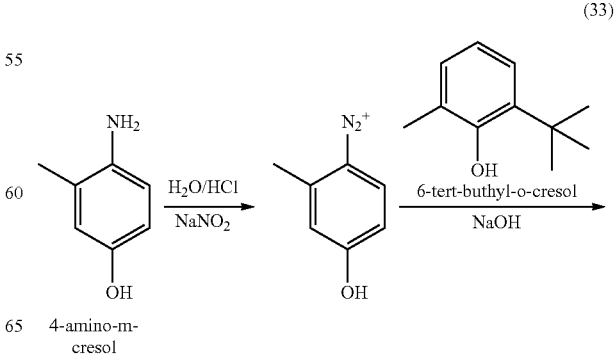

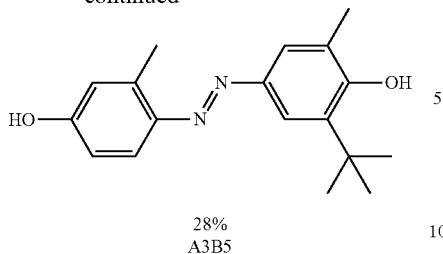

28%
A3B5

Compound A3B5 (Intermediate 14) was subjected to $^1$H NMR analysis to determine the structure.

$^1$H NMR (400 MHz, CDCl$_3$):
7.87 (m, 2H), 7.66 (s, 1H), 6.86 (d, J=7.5 Hz, 1H), 6.78 (s, 1H), 5.18 (s, 2H), 2.64 (s, 3H), 2.32 (s, 3H), 1.45 (s, 9H).

Example 16-2

Synthesis of Compound A3B5-C12 (Azobenzene Derivative 16)

10 mL of acetone, 1-bromododecane (0.548 g, 2.2 mmol), and potassium carbonate (1.10 g, 8 mmol) were added to Compound A3B5 (0.232 g, 0.78 mmol), and the mixture was stirred at 70° C. for 21 hours. After evaporating the solvent under reduced pressure, the resulting solid was purified by silica gel column chromatography (eluant: ethyl acetate:hexane=1:9). A solid that precipitated during the evaporation of the solvent was filtered off, and washed with methanol to obtain Compound A3B5-C12 (orange solid, 0.372 g, yield: 75%).

(34)

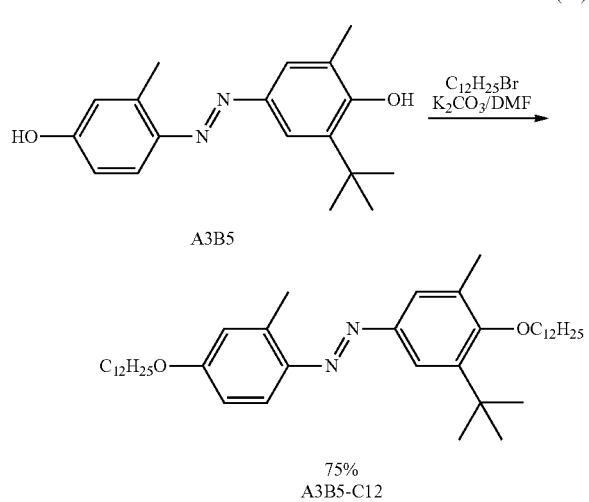

75%
A3B5-C12

Compound A3B5-C12 was subjected to $^1$H NMR analysis and $^{13}$C NMR analysis to determine the structure.

$^1$H NMR (400 MHz, CDCl$_3$):
8.18 (m, 1H), 7.96 (s, 1H), 7.75 (s, 1H), 6.82-6.84 (m, 2H), 4.03 (t, J=6.6 Hz, 2H), 3.85 (t, J=6.8 Hz, 2H), 2.68 (s, 3H), 2.37 (s, 3H), 1.75-1.86 (m, 4H), 1.25-1.49 (m, 45H), 0.85-0.88 (m, 6H).

$^{13}$C NMR (100 MHz, CDCl$_3$):
161.4, 159.3, 148.2, 144.9, 143.4, 140.5, 132.2, 122.4, 121.5, 117.2, 116.0, 112.8, 72.6, 68.2, 35.3, 31.9, 30.9, 30.0, 29.7, 29.6, 29.6, 29.6, 29.6, 29.4, 29.3, 29.2, 26.0, 26.0, 22.7, 17.8, 17.6, 14.1.

MS (MALDI-TOF MS): m/z 635.639 (calc. [M+H]$^+$=635.552).

Example 16-3

DSC Measurement of Compound A3B5-C12

The thermal phase transition temperature of Compound A3B5-C12 was determined by differential scanning calorimetry.
Cr 72 Iso, Iso 28 Cr Example 16-4

Light Exposure Experiment for Compound A3B5-C12

The crystal-isotropic phase transition of Compound A3B5-C12 at 40° C. was observed using a polarizing optical microscope. The results are shown in FIG. 24.

Figure 24:
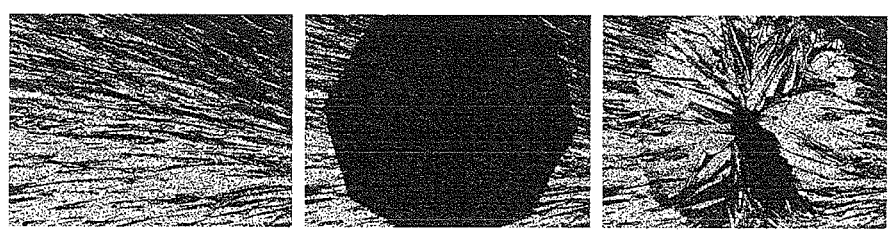
FIG. 24 represents a polarizing optical micrograph showing the crystal-isotropic phase transition of Compound A3B5-C12 at 40° C.

In FIG. 24, the left represents a polarizing optical micrograph before light exposure; the center represents a polarizing optical micrograph just after exposure to ultraviolet light (365 nm) for 40 seconds, and the right represents a polarizing optical micrograph after exposure to visible light (436 nm) for 120 seconds wherein the sample was exposed to ultraviolet light as stated above.

Example 17-1

Synthesis of Compound A4B1 (Intermediate 15)

25 mL of 2.4N hydrochloric acid was added to 4-amino-o-cresol (2.46 g, 20 mmol). After the addition of a solution prepared by dissolving sodium nitrite (1.66 g, 24 mmol) in 5 mL of distilled water to the mixture while stirring the mixture at −6° C., the resulting mixture was stirred for 15 minutes. The resulting solution was added to a mixture (cooled to 0° C.) of 3,5-dimethylphenol (2.44 g, 20 mmol) and 8 mL of a 20% sodium hydroxide aqueous solution, and the mixture was stirred at room temperature for 16 hours. The resulting solution was made acidic using hydrochloric acid under cooling, and extracted with ethyl acetate. The organic layer was washed with a saturated sodium chloride solution, dried over anhydrous magnesium sulfate, and filtered. After evaporating the solvent under reduced pressure, the resulting solid was purified by silica gel column chromatography (eluant: ethyl acetate:hexane=3:7) to obtain Compound A4B1 (brown solid, 2.46 g, yield: 48%).

(35)

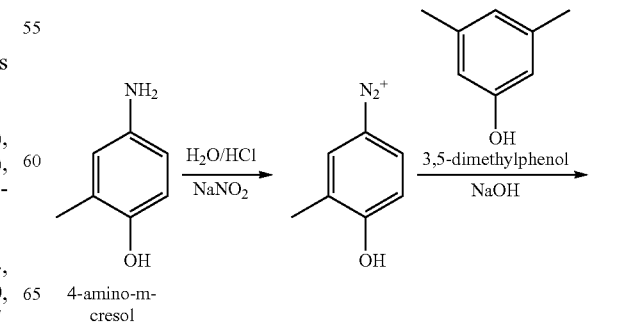

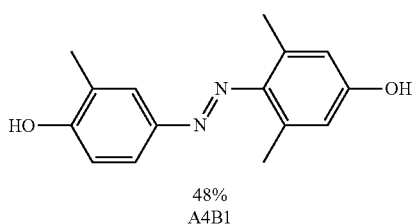

48%
A4B1

Compound A4B1 (Intermediate 15) was subjected to $^1$H NMR analysis to determine the structure.

$^1$H NMR (400 MHz, DMSO-d$_6$):

9.82 (s, 2H), 7.55 (d, J=2.4 Hz, 1H), 7.50 (d-d, J$_1$=8.4 Hz, J$_2$=2.4 Hz, 1H), 6.90 (d, J=8.4 Hz, 1H), 6.53 (s, 2H), 2.32 (s, 6H), 2.19 (s, 3H).

Example 17-2

Synthesis of Compound A4B1-C12 (Azobenzene Derivative 17)

11 mL of DMF, 1-bromododecane (3.3 g, 13 mmol), and potassium carbonate (3.04 g, 22 mmol) were added to Compound A4B1 (0.513 g, 2.0 mmol), and the mixture was stirred at 80° C. for 2 hours, and then stirred at room temperature for 16 hours. The solvent was evaporated under reduced pressure, followed by extraction with ethyl acetate. The organic layer was washed with a saturated sodium chloride solution, dried over anhydrous magnesium sulfate, and filtered. After evaporating the solvent under reduced pressure, the resulting solid was purified by silica gel column chromatography (eluant: ethyl acetate:hexane=5:95) to obtain Compound A4B1-C12 (orange solid, 0.386 g, yield: 33%).

(36)

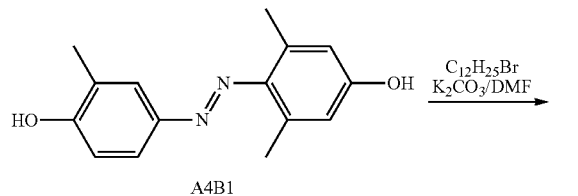

A4B1

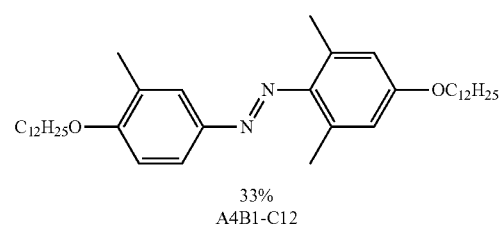

33%
A4B1-C12

Compound A4B1-C12 was subjected to $^1$H NMR analysis and $^{13}$C NMR analysis to determine the structure.

$^1$H NMR (400 MHz, CDCl$_3$):

7.68-7.71 (m, 2H), 6.88 (d, J=8.6 Hz, 1H), 6.62 (s, 2H), 4.02 (t, J=6.4 Hz, 2H), 3.96 (t, J=6.6 Hz, 2H), 2.39 (s, 6H), 2.28 (s, 3H), 1.73-1.85 (m, 4H), 1.25-1.47 (m, 36H), 0.84-0.88 (m, 6H).

$^{13}$C NMR (100 MHz, CDCl$_3$):

159.5, 158.6, 146.5, 144.8, 133.8, 127.5, 123.5, 122.8, 114.9, 110.5, 68.3, 68.0, 31.9, 29.7, 29.6, 29.6, 29.4, 29.3, 29.3, 29.3, 26.1, 26.0, 22.7, 19.9, 16.4, 14.1.

MS (MALDI-TOF MS): m/z 593.575 (calc. [M+H]$^+$=593.505).

Example 17-3

DSC Measurement of Compound A4B1-C12

The thermal phase transition temperature of Compound A4B1-C12 was determined by differential scanning calorimetry.

Cr1Cr2 66 Cr2 72 Iso, Iso 60 Cr1Cr2

Crystal polymorphs were present. Two types of crystals (Cr1 and Cr2) were melted at different temperatures during heating, and precipitated as mixed crystals during cooling.

Example 17-4

Light Exposure Experiment for Compound A4B1-C12

The crystal-isotropic phase transition of Compound A4B1-C12 at 40° C. was observed using a polarizing optical microscope. The results are shown in FIG. 25.

Figure 25:
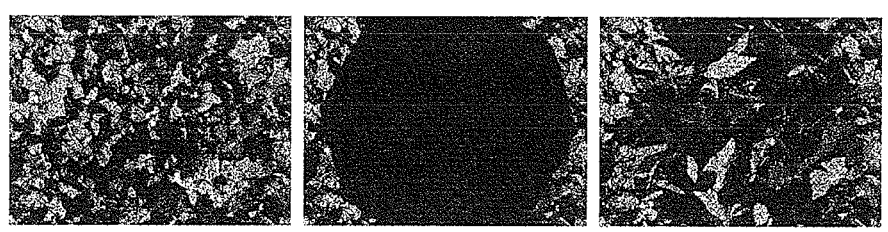
FIG. 25 represents a polarizing optical micrograph showing the crystal-isotropic phase transition of Compound A4B1-C12 at 40° C.

In FIG. 25, the left represents a polarizing optical micrograph before light exposure; the center represents a polarizing optical micrograph just after exposure to ultraviolet light (365 nm) for 33 seconds; and the right represents a polarizing optical micrograph after exposure to visible light (436 nm) for 15 seconds wherein the sample was exposed to ultraviolet light as stated above.

Example 18-1

Synthesis of Compound A4B2 (Intermediate 16)

25 mL of 2.4N hydrochloric acid was added to 4-amino-o-cresol (2.46 g, 20 mmol). After the addition of a solution prepared by dissolving sodium nitrite (1.66 g, 24 mmol) in 5 mL of distilled water to the mixture while stirring the mixture at −6° C., the resulting mixture was stirred for 15 minutes. The resulting solution was added to a mixture (cooled to 0° C.) of 2-isopropyl-5-methylphenol (3.04 g, 20 mmol) and 37 mL of a 20% sodium hydroxide aqueous solution, and the mixture was stirred at room temperature for 16 hours. The resulting solution was made acidic using hydrochloric acid under cooling, and extracted with ethyl acetate. The organic layer was washed with a saturated sodium chloride solution, dried over anhydrous magnesium sulfate, and filtered. After evaporating the solvent under reduced pressure, the resulting solid was purified by silica gel column chromatography (eluant: ethyl acetate:hexane=4:6), and recrystallized from ethanol to obtain Compound A4B2 (brown solid, 2.90 g, yield: 51%).

(37)

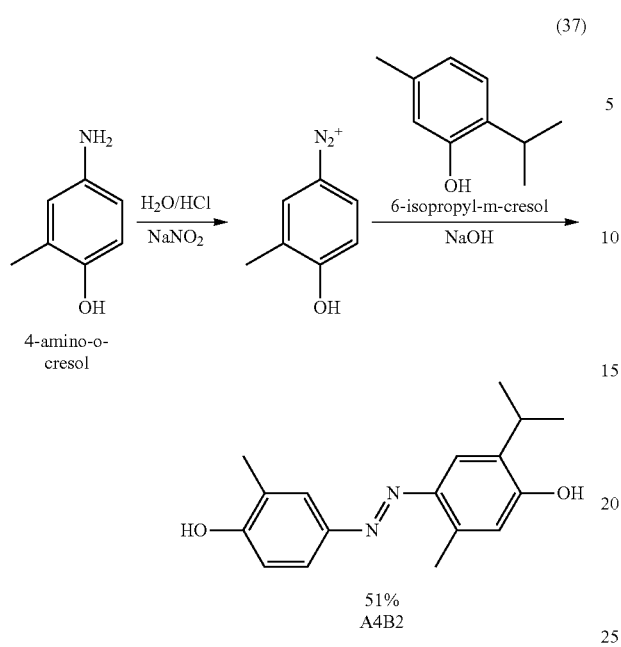

Compound A4B2 (Intermediate 16) was subjected to $^1$H NMR analysis to determine the structure.

$^1$H NMR (400 MHz, DMSO-$d_6$):

9.93 (s, 2H), 7.76 (d, J=2.4 Hz, 1H), 7.54 (d-d, $J_1$=8.4 Hz, $J_2$=2.4 Hz, 1H), 7.47 (s, 1H), 6.90 (d, J=8.4 Hz, 1H), 6.75 (s, 1H), 3.15 (septet, J=6.90, 1H), 2.54 (s, 3H), 2.19 (s, 3H), 1.16 (d, J=6.9 Hz, 6H).

Example 18-2

Synthesis of Compound A4B2-C12 (Azobenzene Derivative 18)

27.5 mL of DMF, 1-bromododecane (8.25 g, 33 mmol), and potassium carbonate (7.59 g, 55 mmol) were added to Compound A4B2 (1.49 g, 5.0 mmol), and the mixture was stirred at 80° C. for 2 hours, and then stirred at room temperature for 16 hours. The solvent was evaporated under reduced pressure, followed by extraction with ethyl acetate. The organic layer was washed with a saturated sodium chloride solution, dried over anhydrous magnesium sulfate, and filtered. After evaporating the solvent under reduced pressure, the resulting solid was purified by silica gel column chromatography (eluant: ethyl acetate:hexane=2:98) to obtain Compound A4B2-C12 (orange solid, 1.64 g, yield: 53%).

(38)

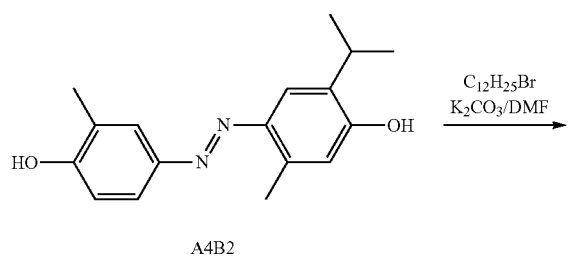

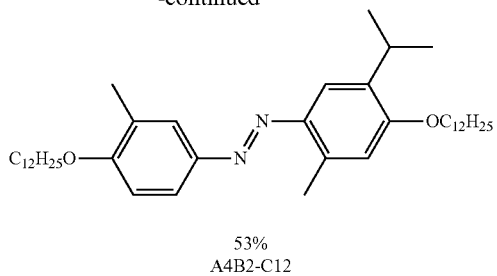

Compound A4B2-C12 was subjected to $^1$H NMR analysis and $^{13}$C NMR analysis to determine the structure.

$^1$H NMR (400 MHz, CDCl$_3$):

7.74 (d-d, $J_1$=8.5 Hz, $J_2$=2.4 Hz, 1H), 7.71 (d, J=2.4 Hz, 1H), 6.87 (d, J=8.6 Hz, 1H), 6.71 (s, 1H), 3.26 (septet, J=6.90, 1H), 2.67 (s, 3H), 2.28 (s, 3H), 1.77-1.84 (m, 4H), 1.44-1.49 (m, 4H), 1.22-1.41 (m, 38H), 0.84-0.88 (m, 6H).

$^{13}$C NMR (100 MHz, CDCl$_3$):

159.2, 158.9, 146.5, 144.2, 137.7, 135.5, 127.4, 123.8, 123.0, 113.9, 112.8, 110.6, 68.3, 68.1, 31.9, 29.7, 29.6, 29.6, 29.4, 29.3, 29.3, 29.3, 27.2, 26.2, 26.1, 22.7, 22.5, 17.5, 16.4, 14.1.

MS (MALDI-TOF MS): m/z 621.607 (calc. [M+H]$^+$=621.536).

Example 18-3

DSC Measurement of Compound A4B2-C12

The thermal phase transition temperature of Compound A4B2-C12 was determined by differential scanning calorimetry.

Cr1Cr2 79 Cr2 91 Iso, Iso 64 Cr1Cr2

Crystal polymorphs were present. Two types of crystals (Cr1 and Cr2) were melted at different temperatures during heating, and precipitated as mixed crystals during cooling.

Example 18-4

Light Exposure Experiment for Compound A4B2-C12

The crystal-isotropic phase transition of Compound A4B2-C12 at 40° C. was observed using a polarizing optical microscope. The results are shown in FIG. 26.

Figure 26:
FIG. 26 represents a polarizing optical micrograph showing the crystal-isotropic phase transition of Compound A4B2-C12 at 40° C.

In FIG. 26, the left represents a polarizing optical micrograph before light exposure; the center represents a polarizing optical micrograph just after exposure to ultraviolet light (365 nm) for 121 seconds; and the right represents a polarizing optical micrograph after exposure to visible light (436 nm) for 11 seconds wherein the sample was exposed to ultraviolet light as stated above.

Example 19-1

Synthesis of Compound A4B3 (Intermediate 17)

25 mL of 2.4N hydrochloric acid was added to 4-amino-o-cresol (2.46 g, 20 mmol). After the addition of a solution prepared by dissolving sodium nitrite (1.66 g, 24 mmol) in 2 mL of distilled water to the mixture while stirring the mixture at −6° C., the resulting mixture was stirred for 15 minutes. The resulting solution was added to a mixture (cooled to −6° C.) of 5-isopropyl-o-cresol (3.0 g, 20 mmol) and 8 mL of a 20% sodium hydroxide aqueous solution, and the mixture was stirred at room temperature for 16 hours. The resulting solution was made acidic using hydrochloric acid under cooling, and extracted with ethyl acetate. The organic layer was washed with a saturated sodium chloride solution, dried over anhydrous magnesium sulfate, and filtered. After evaporating the solvent under reduced pressure, the resulting solid was purified by silica gel column chromatography (eluant: ethyl acetate:hexane=1:1) to obtain Compound A4B3 (brown solid, 1.50 g, yield: 26%).

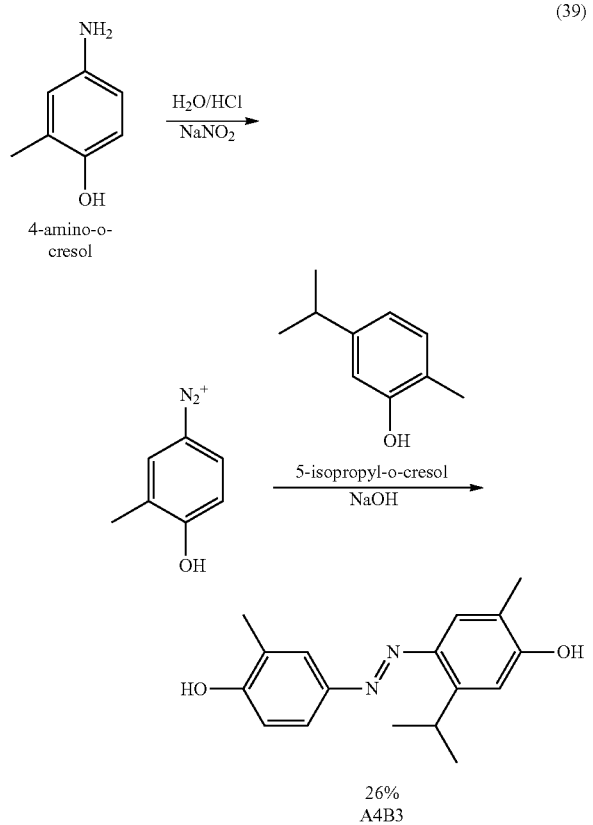

(39)

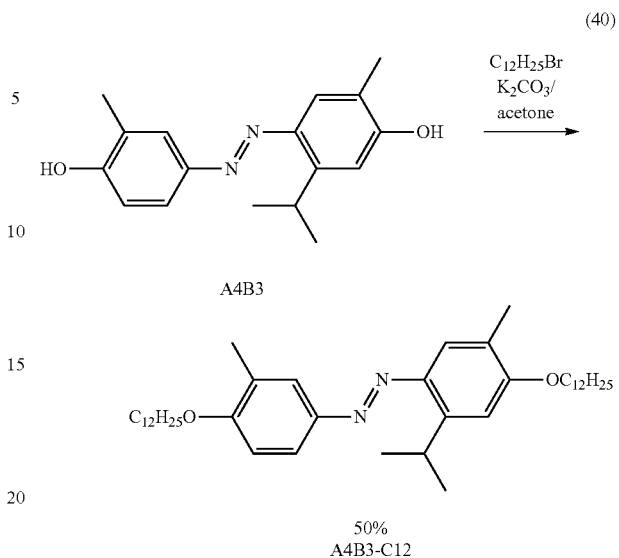

(40)

Compound A4B3 (Intermediate 17) was subjected to $^1$H NMR analysis to determine the structure.

$^1$H NMR (400 MHz, CDCl$_3$):

7.69 (d, J=1.7 Hz, 1H), 7.64 (d-d, J$_1$=8.4 Hz, J$_2$=2.4 Hz, 1H), 7.48 (s, 1H), 6.85 (d, J=8.4 Hz, 1H), 6.78 (s, 1H), 5.31 (s, 1H), 5.19 (s, 1H), 4.06 (septet, J=6.9 Hz, 1H), 2.32 (s, 3H), 2.23 (s, 3H), 1.28 (d, J=7.0 Hz, 6H).

Example 19-2

Synthesis of Compound A4B3-C12 (Azobenzene Derivative 19)

10 mL of acetone, 1-bromododecane (0.548 g, 2.2 mmol), and potassium carbonate (1.1 g, 8 mmol) were added to Compound A4B3 (0.284 g, 1 mmol), and the mixture was stirred at 70° C. for 20 hours. After evaporating the solvent under reduced pressure, the resulting solid was purified by silica gel column chromatography (eluant: ethyl acetate:hexane=1:9), and recrystallized from acetone to obtain Compound A4B3-C12 (orange solid, 0.31 g, yield: 50%).

Compound A4B3-C12 was subjected to $^1$H NMR analysis and $^{13}$C NMR analysis to determine the structure.

$^1$H NMR (400 MHz, CDCl$_3$):

8.23 (s, 1H), 8.08 (d-d, J$_1$=8.8 Hz, J$_2$=2.4 Hz, 1H), 7.86 (d, J=2.4 Hz, 1H), 6.88 (d, J=8.8 Hz, 1H), 6.79 (s, 1H), 3.96-4.09 (m, 5H), 2.28 (s, 3H), 2.24 (s, 3H), 1.78-1.86 (m, 4H), 1.44-1.51 (m, 4H), 1.18-1.35 (m, 38H), 0.84-0.88 (m, 6H).

$^{13}$C NMR (100 MHz, CDCl$_3$):

160.1, 159.2, 148.0, 146.5, 142.8, 127.5, 125.1, 123.9, 122.9, 117.8, 110.6, 107.7, 68.3, 68.1, 31.9, 29.7, 29.6, 29.6, 29.4, 29.4, 29.3, 29.3, 29.3, 27.6, 26.1, 26.1, 24.0, 22.7, 16.4, 15.9, 14.1.

MS (MALDI-TOF MS): m/z 621.609 (calc. [M+H]$^+$=621.536).

Example 19-3

DSC Measurement of Compound A4B3-C12

The thermal phase transition temperature of Compound A4B3-C12 was determined by differential scanning calorimetry.

Cr 42 Cr 52 Iso, Iso 19 Cr

Example 19-4

Light Exposure Experiment for Compound A4B3-C12

The crystal-isotropic phase transition of Compound A4B3-C12 at 26° C. was observed using a polarizing optical microscope. The results are shown in FIG. 27.

Figure 27:
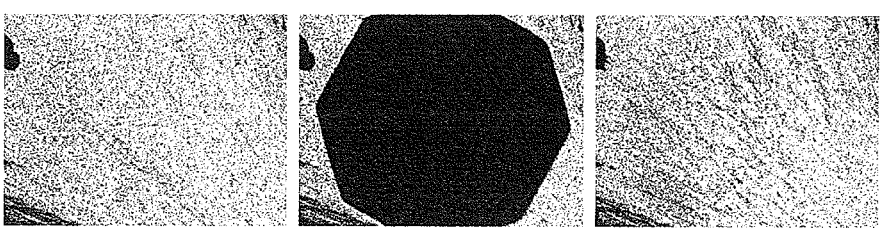
FIG. 27 represents a polarizing optical micrograph showing the crystal-isotropic phase transition of Compound A4B3-C12 at 26° C.

In FIG. 27, the left represents a polarizing optical micrograph before light exposure; the center represents a polarizing optical micrograph just after exposure to ultraviolet light (365 nm) for 6 seconds; and the right represents a polarizing optical micrograph after exposure to visible light (436 nm) for 780 seconds wherein the sample was exposed to ultraviolet light as stated above.

Example 20-1

Synthesis of Compound A4B4 (Intermediate 18)

25 mL of 2.4N hydrochloric acid was added to 4-amino-o-cresol (2.46 g, 20 mmol). After the addition of a solution prepared by dissolving sodium nitrite (1.66 g, 24 mmol) in 5 mL of distilled water to the mixture while stirring the mixture at −6° C., the resulting mixture was stirred for 15 minutes. The resulting solution was added to a mixture (cooled to 0° C.) of m-cresol (2.16 g, 20 mmol) and 37 mL of a 20% sodium hydroxide aqueous solution, and the mixture was stirred at room temperature for 16 hours. The resulting solution was made acidic using hydrochloric acid under cooling, and extracted with ethyl acetate. The organic layer was washed with a saturated sodium chloride solution, dried over anhydrous magnesium sulfate, and filtered. After evaporating the solvent under reduced pressure, the resulting solid was purified by silica gel column chromatography (eluant: ethyl acetate:hexane=4:6), and recrystallized from ethanol to obtain Compound A4B4 (brown solid, 1.59 g, yield: 33%).

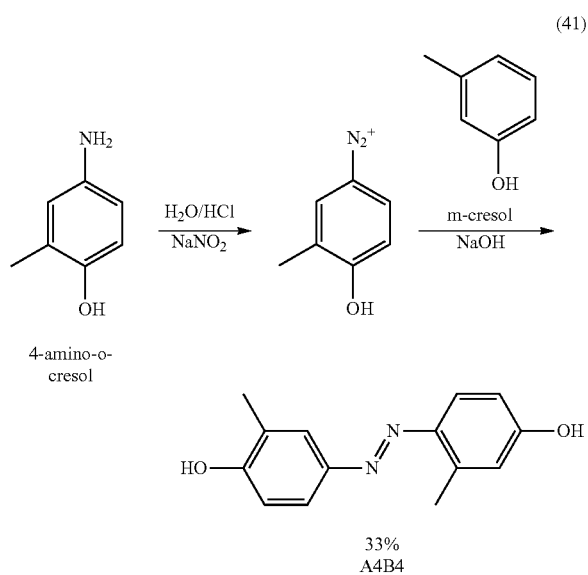

(41)

Compound A4B4 (Intermediate 18) was subjected to $^1$H NMR analysis to determine the structure.

$^1$H NMR (400 MHz, DMSO-$d_6$):
9.97 (s, 2H), 7.59 (d, J=2.2 Hz, 1H), 7.54 (d-d, $J_1$=8.4 Hz, $J_2$=2.2 Hz, 1H), 7.49 (d, J=8.8 Hz, 1H), 6.90 (d, J=8.4 Hz, 1H), 6.73 (d, J=2.6 Hz, 1H), 6.66 (d-d, $J_1$=8.8 Hz, $J_2$=2.6 Hz, 1H), 2.57 (s, 3H), 2.19 (s, 3H).

Example 20-2

Synthesis of Compound A4B4-C12 (Azobenzene Derivative 20)

11 mL of DMF, 1-bromododecane (3.3 g, 13 mmol), and potassium carbonate (3.04 g, 22 mmol) were added to Compound A4B4 (0.485 g, 2 mmol), and the mixture was stirred at 80° C. for 2 hours, and then stirred at room temperature for 16 hours. After evaporating the solvent under reduced pressure, the resulting solid was purified by silica gel column chromatography (eluant: ethyl acetate:hexane=5:95) to obtain Compound A4B4-C12 (orange solid, 0.92 g, yield: 80%).

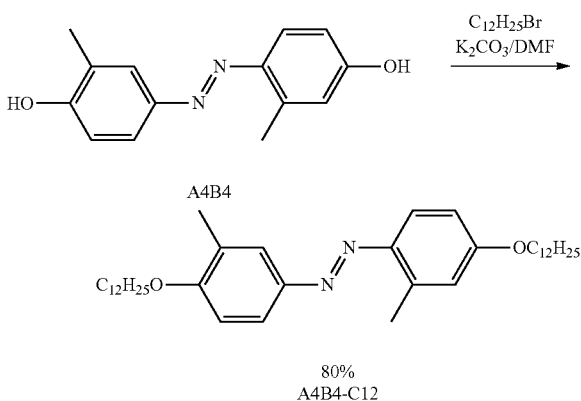

(42)

Compound A4B4-C12 was subjected to $^1$H NMR analysis and $^{13}$C NMR analysis to determine the structure.

$^1$H NMR (400 MHz, CDCl$_3$):
7.10-7.73 (m, 2H), 7.66 (d, J=8.9 Hz, 1H), 6.87 (d, J=8.5 Hz, 1H), 6.79 (d, J=2.6 Hz, 1H), 6.75 (d-d, $J_1$=8.8 Hz, $J_2$=26 Hz, 1H), 3.97-4.03 (m, 4H), 2.68 (s, 3H), 2.27 (s, 3H), 1.74-1.85 (m, 4H), 1.25-1.59 (m, 36H), 0.84-0.88 (m, 6H).

$^{13}$C NMR (100 MHz, CDCl$_3$):
161.2, 159.4, 146.4, 144.8, 140.3, 127.5, 123.8, 123.2, 117.2, 116.0, 112.8, 110.6, 77.0, 68.3, 68.2, 31.9, 29.7, 29.6, 29.6, 29.4, 29.3, 29.3, 29.2, 26.1, 26.0, 22.7, 17.8, 16.4, 14.1.

MS (MALDI-TOF MS): m/z 579.545 (calc. [M+H]$^+$=579.489).

Example 20-3

DSC Measurement of Compound A4B4-C12

The thermal phase transition temperature of Compound A4B4-C12 was determined by differential scanning calorimetry.

Cr1Cr2 61 Cr2 70 Iso, Iso 51 Cr1Cr2

Crystal polymorphs were present. Two types of crystals (Cr1 and Cr2) were melted at different temperatures during heating, and precipitated as mixed crystals during cooling.

Example 20-4

Light Exposure Experiment for Compound A4B4-C12

The crystal-isotropic phase transition of Compound A4B4-C12 at 35° C. was observed using a polarizing optical microscope. The results are shown in FIG. 28.

Figure 28:
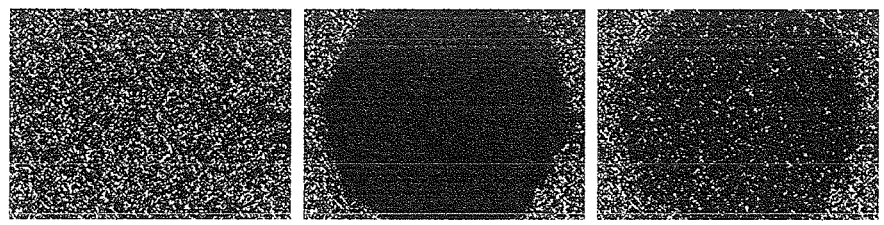
FIG. 28 represents a polarizing optical micrograph showing the crystal-isotropic phase transition of Compound A4B4-C12 at 35° C.

In FIG. 28, the left represents a polarizing optical micrograph before light exposure; the center represents a polarizing optical micrograph just after exposure to ultraviolet light (365 nm) for 80 seconds; and the right represents a polarizing optical micrograph after exposure to visible light (436 nm) for 2 seconds wherein the sample was exposed to ultraviolet light as stated above.

Example 21-1

Synthesis of Compound A4B5 (Intermediate 19)

25 mL of 2.4N hydrochloric acid was added to 4-amino-o-cresol (2.46 g, 20 mmol). After the addition of a solution prepared by dissolving sodium nitrite (1.66 g, 24 mmol) in 5 mL of distilled water to the mixture while stirring the mixture at −6° C., the resulting mixture was stirred for 15 minutes. The resulting solution was added to a mixture (cooled to 0° C.) of 6-tert-butyl-o-cresol (3.28 g, 20 mmol) and 37 mL of a 20% sodium hydroxide aqueous solution, and the mixture was stirred at room temperature for 16 hours. The resulting solution was made acidic using hydrochloric acid under cooling, and extracted with chloroform, and the organic layer was extracted with a sodium hydroxide aqueous solution. The resulting alkaline aqueous layer was made acidic using hydrochloric acid, and extracted with ethyl acetate. The organic layer was washed with a saturated sodium chloride solution, dried over anhydrous magnesium sulfate, and filtered. After evaporating the solvent under reduced pressure, the resulting solid was purified by silica gel column chromatography (eluant: ethyl acetate:hexane=2:8), and recrystallized from ethanol to obtain Compound A4B5 (brown solid, 1.69 g, yield: 28%).

pound A4B5 (0.596 g, 2 mmol), and the mixture was stirred at 80° C. for 2 hours, and then stirred at room temperature for 16 hours. The solvent was evaporated under reduced pressure, followed by extraction with ethyl acetate. The organic layer was washed with a saturated sodium chloride solution, dried over anhydrous magnesium sulfate, and filtered. After evaporating the solvent under reduced pressure, the resulting solid was purified by silica gel column chromatography (eluant: ethyl acetate:hexane=3:7) to obtain Compound A4B5-C12 (orange solid, 1.03 g, yield: 81%).

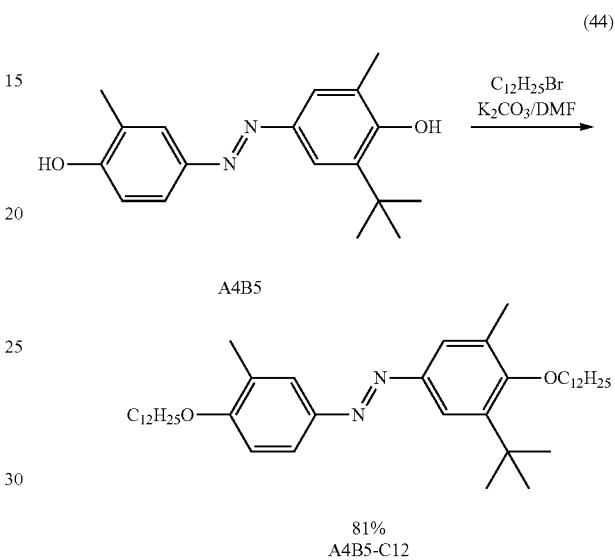

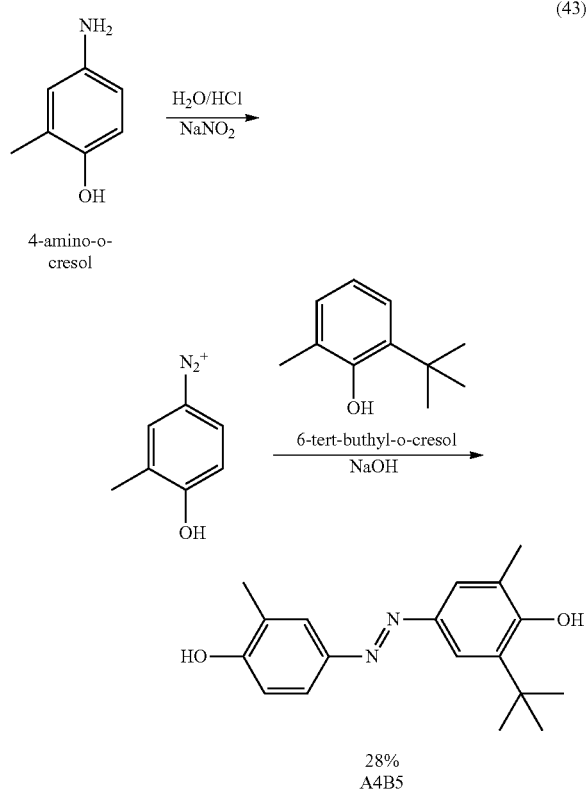

Compound A4B5 (Intermediate 19) was subjected to $^1$H NMR analysis to determine the structure.

$^1$H NMR (400 MHz, DMSO-d$_6$):
10.00 (s, 1H), 8.79 (s, 1H), 7.59-7.60 (m, 2H), 7.54 (d-d, J$_1$=8.5 Hz, J$_2$=2.4 Hz, 1H), 7.47 (d, J=1.8 Hz, 1H), 6.90 (d, J=8.5 Hz, 1H), 2.27 (s, 3H), 2.19 (s, 3H), 1.41 (s, 9H).

Example 21-2

Synthesis of Compound A4B5-C12 (Azobenzene Derivative 21)

11 mL of DMF, 1-bromododecane (3.3 g, 13 mmol), and potassium carbonate (3.04 g, 22 mmol) were added to Com- Compound A4B5-C12 was subjected to $^1$H NMR analysis and $^{13}$C NMR analysis to determine the structure.

$^1$H NMR (400 MHz, CDCl$_3$):
7.85 (d-d, J$_1$=8.5 Hz, J$_2$=2.4 Hz, 1H), 7.80-7.82 (m, 2H), 7.65 (d, J=1.9 Hz, 1H), 6.90 (d, J=8.5 Hz, 1H), 4.03 (t, J=6.4 Hz, 2H), 3.84 (t, J=6.8 Hz, 2H), 2.36 (s, 3H), 2.28 (s, 3H), 1.78-1.86 (m, 4H), 1.45-1.52 (m, 4H), 1.44 (s, 9H), 1.23-1.40 (m, 32H), 0.85-0.88 (m, 6H).

$^{13}$C NMR (100 MHz, CDCl$_3$):
159.9, 159.5, 147.7, 146.1, 143.5, 132.3, 127.6, 123.8, 122.2, 121.6, 110.6, 72.6, 68.3, 35.3, 31.9, 31.0, 30.0, 29.7, 29.6, 29.6, 29.6, 29.4, 29.3, 29.2, 26.1, 26.0, 22.7, 17.6, 16.4, 14.1.

MS (MALDI-TOF MS): m/z 635.604 (calc. [M+H]$^+$=635.552).

Example 21-3

DSC Measurement of Compound A4B5-C12

The thermal phase transition temperature of Compound A4B5-C12 was determined by differential scanning calorimetry.
Cr 45 Iso, Iso 13 Cr Example 21-4

Light Exposure Experiment for Compound A4B5-C12

The crystal-isotropic phase transition of Compound A4B5-C12 at 22° C. was observed using a polarizing optical microscope. The results are shown in FIG. 29.

Figure 29:
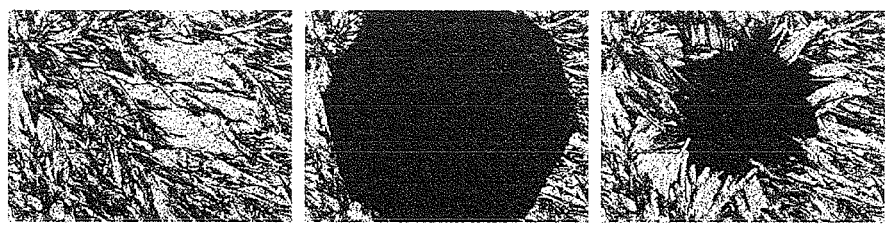
FIG. 29 represents a polarizing optical micrograph showing the crystal-isotropic phase transition of Compound A4B5-C12 at 22° C.

In FIG. 29, the left represents a polarizing optical micrograph before light exposure; the center represents a polarizing optical micrograph just after exposure to ultraviolet light (365 nm) for 35 seconds; and the right represents a polarizing optical micrograph after exposure to visible light (436 nm) for 600 seconds wherein the sample was exposed to ultraviolet light as stated above.

Example 22-1

Synthesis of Compound A4B6 (Intermediate 20)

25 mL of 2.4N hydrochloric acid was added to 4-amino-o-cresol (2.46 g, 20 mmol). After the addition of a solution prepared by dissolving sodium nitrite (1.66 g, 24 mmol) in 2 mL of distilled water to the mixture while stirring the mixture at −6° C., the resulting mixture was stirred for 15 minutes. The resulting solution was added to a mixture (cooled to 0° C.) of 2-isopropylphenol (2.72 g, 20 mmol) and 8 mL of a 20% sodium hydroxide aqueous solution, and the mixture was stirred at room temperature for 1 hour. The resulting solution was made acidic using hydrochloric acid under cooling, and extracted with ethyl acetate. The organic layer was washed with a saturated sodium chloride solution, dried over anhydrous magnesium sulfate, and filtered. After evaporating the solvent under reduced pressure, the resulting solid was purified by silica gel column chromatography (eluant: ethyl acetate:hexane=1:2), and recrystallized from a chloroform/hexane mixed solvent to obtain Compound A4B6 (brown solid, 0.76 g, yield: 14%).

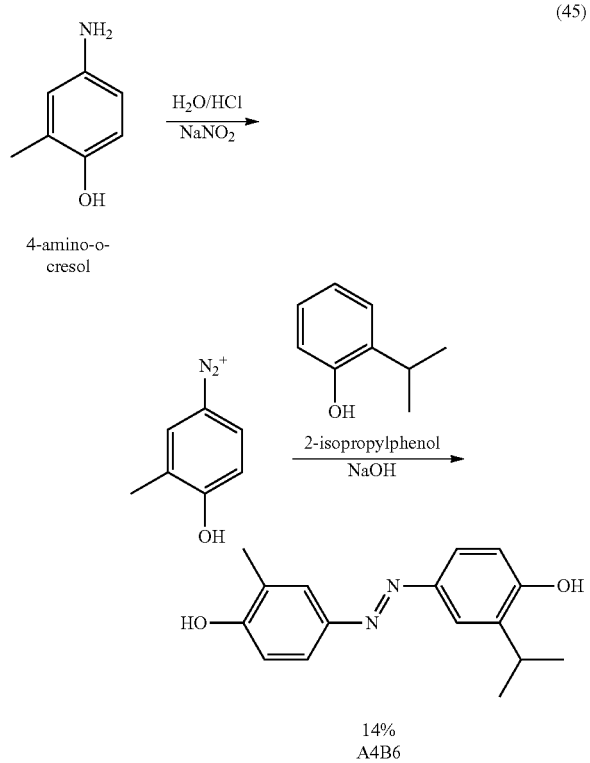

(45)

Compound A4B6 (Intermediate 20) was subjected to $^1$H NMR analysis to determine the structure.

$^1$H NMR (400 MHz, CDCl$_3$):

7.79 (d, J=2.4 Hz, 1H), 7.70 (d, J=2.4 Hz, 1H), 7.66 (d-d, J$_1$=8.4 Hz, J$_2$=2.4 Hz, 1H), 7.62 (d-d, J$_1$=8.4 Hz, J$_2$=2.4 Hz, 1H), 6.85 (d, J=8.4 Hz, 1H), 6.82 (d, J=8.4 Hz, 1H), 5.15 (s, 1H), 5.11 (s, 1H), 3.24 (septet, J=6.9 Hz, 1H), 2.31 (s, 3H), 1.31 (d, J=6.9 Hz, 6H).

Example 22-2

Synthesis of Compound A4B6-C12 (Azobenzene Derivative 22)

10 mL of acetone, 1-bromododecane (0.548 g, 2.2 mmol), and potassium carbonate (1.10 g, 8 mmol) were added to Compound A4B6 (0.270 g, 1.0 mmol), and the mixture was stirred at 70° C. for 20 hours. After evaporating the solvent under reduced pressure, the resulting solid was purified by silica gel column chromatography (eluant: ethyl acetate:hexane=1:9), and recrystallized from acetone to obtain Compound A4B6-C12 (orange solid, 0.607 g, yield: 94%).

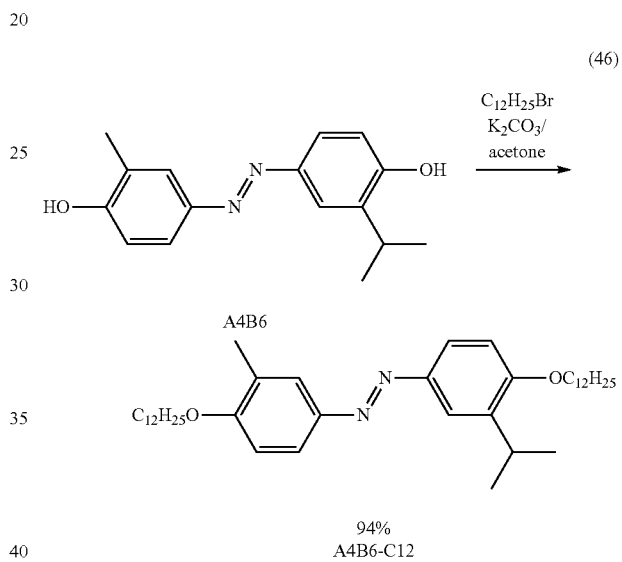

(46)

Compound A4B6-C12 was subjected to $^1$H NMR analysis and $^{13}$C NMR analysis to determine the structure.

$^1$H NMR (400 MHz, CDCl$_3$):

7.80 (d, J=2.4 Hz, 1H), 7.69-7.40 (m, 3H), 6.90 (d, J=8.7 Hz, 1H), 6.88 (d, J=9.3 Hz, 1H), 4.02 (t, J=6.4 Hz, 4H), 3.35 (septet, J=6.9 Hz, 1H), 2.27 (s, 3H), 1.78-1.85 (m, 4H), 1.25-1.60 (m, 42H), 0.85-0.88 (m, 6H).

$^{13}$C NMR (100 MHz, CDCl$_3$):

159.5, 158.6, 146.4, 146.1, 137.7, 127.6, 123.6, 123.4, 122.0, 120.7, 111.0, 110.6, 68.3, 68.3, 31.9, 29.7, 29.6, 29.6, 29.4, 29.3, 29.3, 29.3, 27.2, 26.2, 26.1, 22.7, 22.5, 16.4, 14.1.

MS (MALDI-TOF MS): m/z 607.567 (calc. [M+H]$^+$=607.520).

Example 22-3

DSC Measurement of Compound A4B6-C12

The thermal phase transition temperature of Compound A4B6-C12 was determined by differential scanning calorimetry.

Cr 87 Iso, Iso 51 Cr

Example 22-4

Light Exposure Experiment for Compound A4B6-C12

The crystal-isotropic phase transition of Compound A4B6-C12 at 40° C. was observed using a polarizing optical microscope. The results are shown in FIG. 30.

Figure 30:
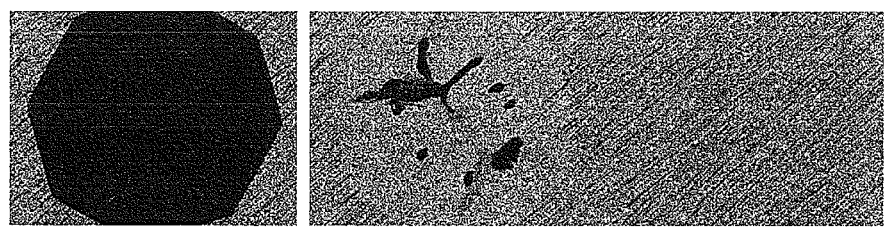
FIG. 30 represents a polarizing optical micrograph showing the crystal-isotropic phase transition of Compound A4B6-C12 at 40° C.

In FIG. 30, the left represents a polarizing optical micrograph before light exposure; the center represents a polarizing optical micrograph just after exposure to ultraviolet light (365 nm) for 35 seconds; and the right represents a polarizing optical micrograph after exposure to visible light (436 nm) for 3 seconds wherein the sample was exposed to ultraviolet light as stated above.

Example 23-1

Synthesis of Compound A4B7 (Intermediate 21)

25 mL of 2.4N hydrochloric acid was added to 4-amino-o-cresol (2.46 g, 20 mmol). After the addition of a solution prepared by dissolving sodium nitrite (1.66 g, 24 mmol) in 2 mL of distilled water to the mixture while stirring the mixture at −6° C., the resulting mixture was stirred for 15 minutes. The resulting solution was added to a mixture (cooled to 0° C.) of 2,6-diisopropylphenol (3.56 g, 20 mmol) and 8 mL of a 20% sodium hydroxide aqueous solution, and the mixture was stirred for 1 hour in an ice bath. The resulting solution was made acidic using hydrochloric acid under cooling, and a solid precipitate was filtered off, and washed with water. The solid was dissolved in acetone, and the solution was dried over anhydrous magnesium sulfate, and filtered. After evaporating the solvent under reduced pressure, the resulting solid was purified by silica gel column chromatography (eluant: ethyl acetate:hexane=1:2), and recrystallized from a chloroform/hexane mixed solvent to obtain Compound A4B7 (red solid, 1.61 g, yield: 26%).

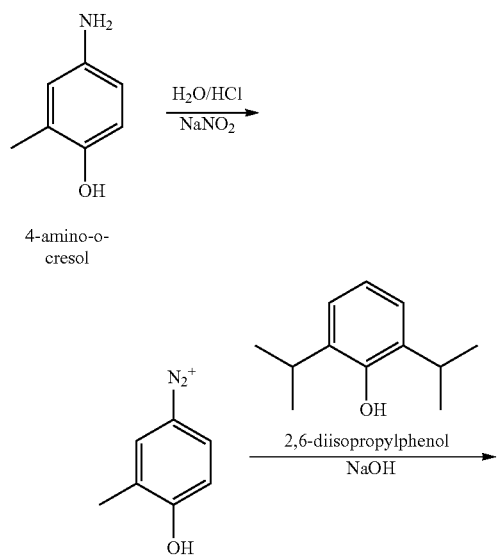

(47)

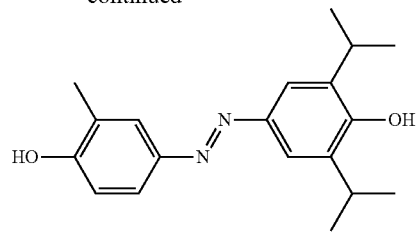

26%
A4B7

Compound A4B7 (Intermediate 21) was subjected to $^1$H NMR analysis to determine the structure.

$^1$H NMR (400 MHz, CDCl$_3$):

7.71 (d, J=2.3 Hz, 1H), 7.67 (d-d, J$_1$=8.4 Hz, J$_2$=2.2 Hz, 1H), 7.66 (s, 2H), 6.85 (d, J=8.4 Hz, 1H), 5.22 (s, 1H), 5.11 (s, 1H), 3.18 (septet, J=6.8 Hz, 2H), 2.31 (s, 3H), 1.32 (d, J=6.8 Hz, 6H).

Example 23-2

Synthesis of Compound A4B7-C12 (Azobenzene Derivative 23)

10 mL of acetone, 1-bromododecane (0.548 g, 2.2 mmol), and potassium carbonate (1.10 g, 8 mmol) were added to Compound A4B7 (0.312 g, 1.0 mmol), and the mixture was stirred at 80° C. for 20 hours. After evaporating the solvent under reduced pressure, the resulting solid was purified by silica gel column chromatography (eluant: ethyl acetate:hexane=1:9), and recrystallized from acetone to obtain Compound A4B7-C12 (yellow solid, 0.636 g, yield: 98%).

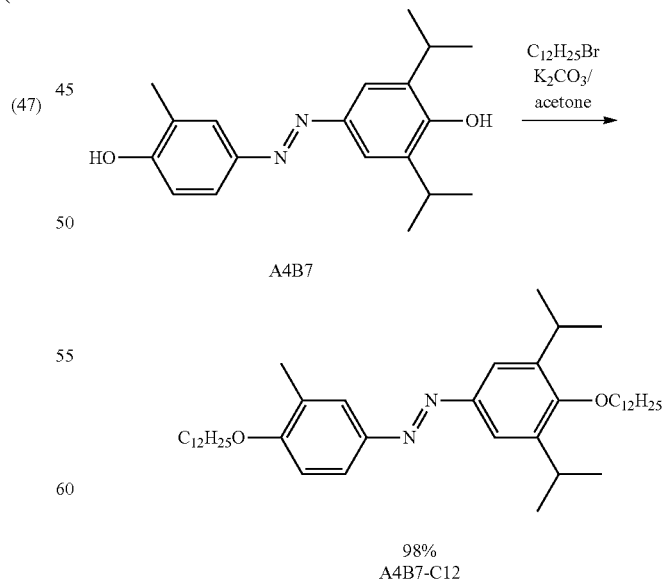

(48)

Compound A4B7-C12 was subjected to $^1$H NMR analysis and $^{13}$C NMR analysis to determine the structure.

¹H NMR (400 MHz, CDCl₃):

7.74-7.77 (m, 2H), 7.65 (s, 2H), 6.89 (d, J=8.6 Hz, 1H), 4.03 (t, J=6.4 Hz, 2H), 3.75 (t, J=6.6 Hz, 2H), 3.33 (septet, J=6.8 Hz, 2H), 2.28 (s, 3H), 1.77-1.86 (m, 4H), 1.25-1.58 (m, 48H), 0.84-0.88 (m, 6H).

¹³C NMR (100 MHz, CDCl₃):

159.8, 155.8, 149.2, 146.2, 142.8, 127.6, 123.8, 123.8, 118.7, 110.6, 75.1, 68.3, 31.9, 30.4, 29.7, 29.6, 29.6, 29.5, 29.4, 29.3, 29.3, 26.8, 26.1, 26.1, 24.0, 22.7, 16.3, 14.1.

MS (MALDI-TOF MS): m/z 649.598 (calc. [M+H]⁺=649.567).

Example 23-3

DSC Measurement of Compound A4B7-C12

The thermal phase transition temperature of Compound A4B7-C12 was determined by differential scanning calorimetry.

Cr 32 Cr 45 Iso, Iso 4 Cr

Example 23-4

Light Exposure Experiment 1 for Compound A4B7-C12

The crystal-isotropic phase transition of Compound A4B7-C12 at 26° C. was observed using a polarizing optical microscope. The results are shown in FIG. 31.

Figure 31:
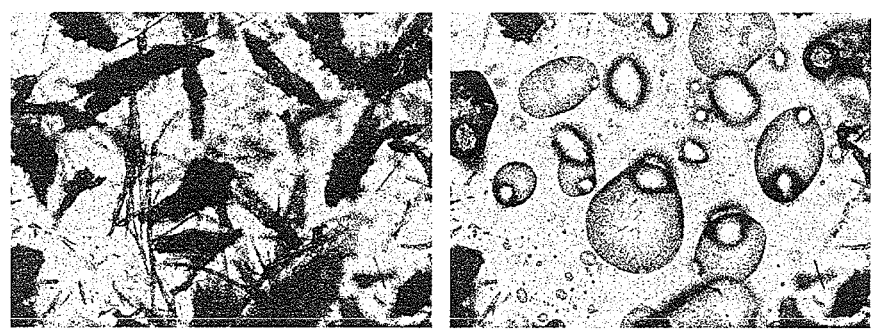
FIG. 31 represents a polarizing optical micrograph showing the crystal-isotropic phase transition of Compound A4B7-C12 at 26° C.

In FIG. 31, the left represents a polarizing optical micrograph before light exposure; and the right represents a polarizing optical micrograph just after exposure to ultraviolet light (365 nm) for 100 seconds.

Example 23-5

Light Exposure Experiment 2 for Compound A4B7-C12

The crystal-isotropic phase transition of Compound A4B7-C12 at 23° C. was observed using a polarizing optical microscope. The results are shown in FIG. 32.

Figure 32:
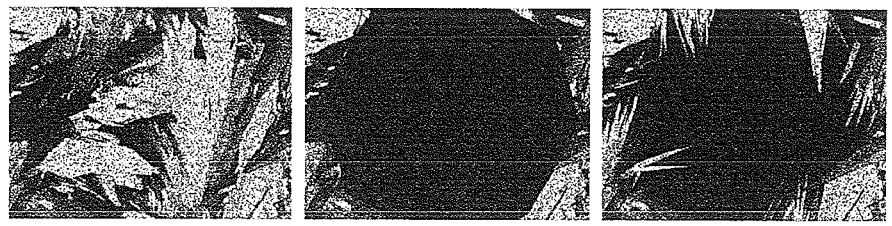
FIG. 32 represents a polarizing optical micrograph showing the crystal-isotropic phase transition of Compound A4B7-C12 at 23° C.

In FIG. 32, the left represents a polarizing optical micrograph before light exposure; the center represents a polarizing optical micrograph just after exposure to ultraviolet light (365 nm) for 24 seconds; and the right represents a polarizing optical micrograph after exposure to visible light (436 nm) for 300 seconds wherein the sample was exposed to ultraviolet light as stated above.

Example 24-1

Synthesis of Compound A4B8 (Intermediate 22)

25 mL of 2.4N hydrochloric acid was added to 4-amino-o-cresol (2.46 g, 20 mmol). After the addition of a solution prepared by dissolving sodium nitrite (1.66 g, 24 mmol) in 2 mL of distilled water to the mixture while stirring the mixture at −6° C., the resulting mixture was stirred for 15 minutes. The resulting solution was added to a mixture (cooled to 0° C.) of 2-tert-butylphenol (3.00 g, 20 mmol) and 8 mL of a 20% sodium hydroxide aqueous solution, and the mixture was stirred for 1 hour in an ice bath. The resulting solution was made acidic using hydrochloric acid under cooling, and extracted with ethyl acetate. The organic layer was washed with water, dried over anhydrous magnesium sulfate, and filtered. After evaporating the solvent under reduced pressure, the resulting solid was purified by silica gel column chromatography (eluant: ethyl acetate:hexane=1:2), and recrystallized from a chloroform/hexane mixed solvent to obtain Compound A4B8 (red solid, 0.92 g, yield: 16%).

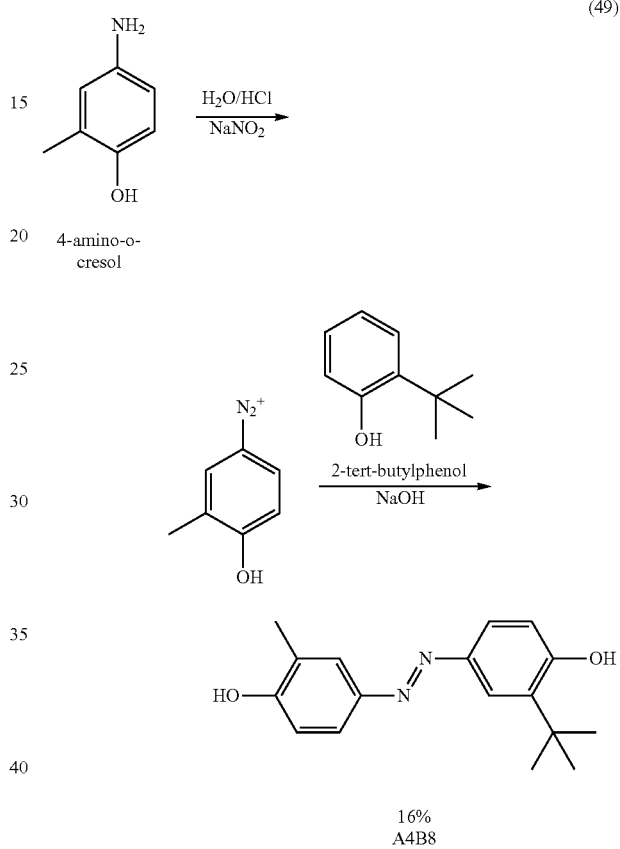

(49)

Compound A4B8 (Intermediate 22) was subjected to ¹H NMR analysis to determine the structure.

¹H NMR (400 MHz, CDCl₃):

7.87 (d, J=2.4 Hz, 1H), 7.62-7.70 (m, 3H), 6.86 (d, J=8.3 Hz, 1H), 6.76 (d, J=8.2 Hz, 1H), 5.35 (s, 1H), 5.18 (s, 1H), 2.31 (s, 3H), 1.45 (s, 9H).

Example 24-2

Synthesis of Compound A4B8-C12 (Azobenzene Derivative 24)

10 mL of acetone, 1-bromododecane (0.548 g, 2.2 mmol), and potassium carbonate (1.10 g, 8 mmol) were added to Compound A4B8 (0.284 g, 1.0 mmol), and the mixture was stirred at 70° C. for 20 hours. After evaporating the solvent under reduced pressure, the resulting solid was purified by silica gel column chromatography (eluant: ethyl acetate:hexane=1:9), and recrystallized from acetone to obtain Compound A4B8-C12 (yellow solid, 0.531 g, yield: 86%).

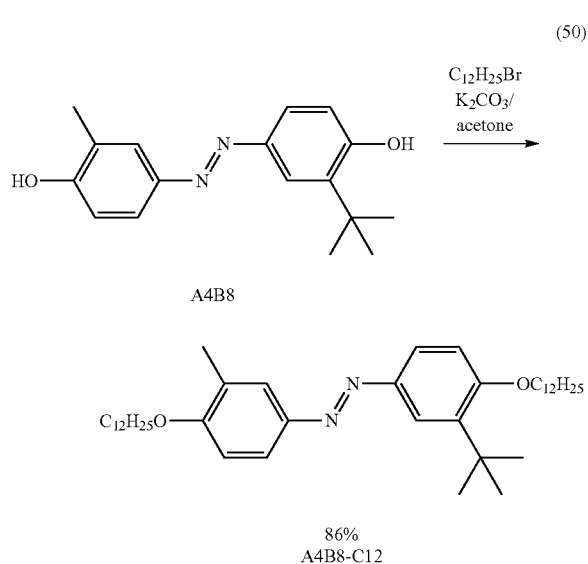

(50)

A4B8

86%
A4B8-C12

Compound A4B8-C12 was subjected to $^1$H NMR analysis and $^{13}$C NMR analysis to determine the structure.

$^1$H NMR (400 MHz, CDCl$_3$):

7.90 (d, J=2.4, 1H), 7.73-7.76 (m, 3H), 6.93 (d, J=8.8 Hz, 1H), 6.88 (d, J=8.5 Hz, 1H), 4.00-4.06 (m, 4H), 2.27 (s, 3H), 1.78-1.89 (m, 4H), 1.25-1.63 (m, 45H), 0.84-0.88 (m, 6H).

$^{13}$C NMR (100 MHz, CDCl$_3$):

160.2, 159.5, 146.1, 146.1, 138.7, 127.6, 123.6, 123.4, 122.1, 121.6, 111.8, 110.6, 68.3, 35.1, 31.9, 29.7, 29.6, 29.6, 29.5, 29.4, 29.3, 29.3, 26.3, 26.1, 22.7, 16.4, 14.1.

MS (MALDI-TOF MS): m/z 621.613 (calc. [M+H]$^+$=621.536).

Example 24-3

DSC Measurement of Compound A4B8-C12

The thermal phase transition temperature of Compound A4B8-C12 was determined by differential scanning calorimetry.

Cr 97 Iso, Iso 60 Cr

Example 24-4

Light Exposure Experiment for Compound A4B8-C12

The crystal-isotropic phase transition of Compound A4B8-C12 at 50° C. was observed using a polarizing optical microscope. The results are shown in FIG. 33.

Figure 33:
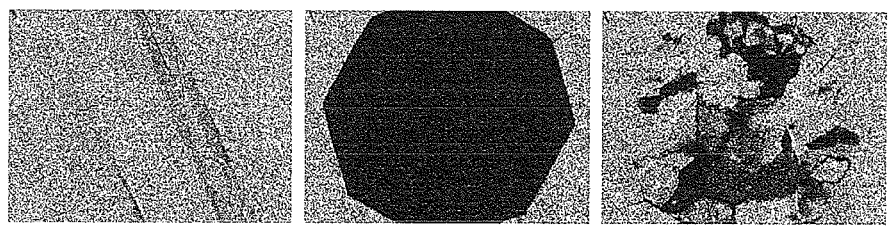
FIG. 33 represents a polarizing optical micrograph showing the crystal-isotropic phase transition of Compound A4B8-C12 at 50° C.

In FIG. 33, the left represents a polarizing optical micrograph before light exposure; the center represents a polarizing optical micrograph just after exposure to ultraviolet light (365 nm) for 51 seconds; and the right represents a polarizing optical micrograph after exposure to visible light (436 nm) for 3 seconds wherein the sample was exposed to ultraviolet light as stated above.

Example 25-1

Synthesis of Compound A4B9 (Intermediate 23)

25 mL of 2.4N hydrochloric acid was added to 4-amino-o-cresol (2.46 g, 20 mmol). After the addition of a solution prepared by dissolving sodium nitrite (1.66 g, 24 mmol) in 2 mL of distilled water to the mixture while stirring the mixture at −6° C., the resulting mixture was stirred for 15 minutes. The resulting solution was added to a mixture (cooled to 0° C.) of o-cresol (2.16 g, 20 mmol) and 8 mL of a 20% sodium hydroxide aqueous solution, and the mixture was stirred at room temperature for 16 hours. The resulting solution was made acidic using hydrochloric acid under cooling, and extracted with ethyl acetate. The organic layer was washed with a saturated sodium chloride solution, dried over anhydrous magnesium sulfate, and filtered. After evaporating the solvent under reduced pressure, the resulting solid was purified by silica gel column chromatography (eluant: ethyl acetate:hexane=1:2) to obtain Compound A4B9 (brown solid, 0.216 g, yield: 4%).

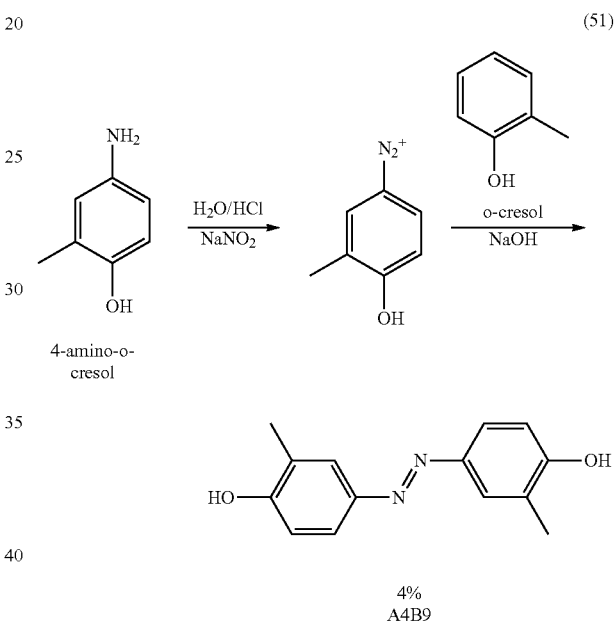

(51)

4%
A4B9

Compound A4B9 (Intermediate 23) was subjected to $^1$H NMR analysis to determine the structure.

$^1$H NMR (400 MHz, DMSO-d$_6$):

10.02 (s, 2H), 7.60 (d, J=2.0 Hz, 2H), 7.54 (d-d, J$_1$=8.5 Hz, J$_2$=2.4 Hz, 2H), 6.91 (d, J=8.5 Hz, 2H), 2.19 (s, 6H).

Example 25-2

Synthesis of Compound A4B9-C12 (Azobenzene Derivative 25)

10 mL of acetone, 1-bromododecane (0.548 g, 2.2 mmol), and potassium carbonate (1.10 g, 8 mmol) were added to Compound A4B9 (0.242 g, 1.0 mmol), and the mixture was stirred at 75° C. for 26 hours. After evaporating the solvent under reduced pressure, the resulting solid was purified by silica gel column chromatography (eluant: ethyl acetate:hexane=1:9), and recrystallized from acetone to obtain Compound A4B9-C12 (orange solid, 0.208 g, yield: 36%).

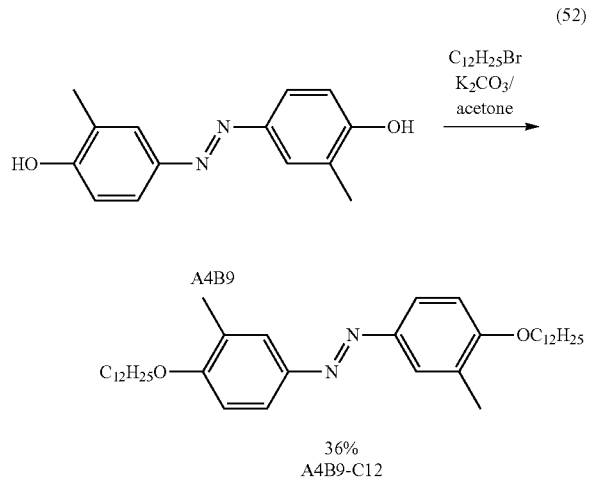

Compound A4B9-C12 was subjected to $^1$H NMR analysis and $^{13}$C NMR analysis to determine the structure.

$^1$H NMR (400 MHz, CDCl$_3$):
7.90 (d-d, $J_1$=8.6 Hz, $J_2$=2.0 Hz, 2H), 7.86 (d, J=2.0 Hz, 2H), 6.93 (d, J=8.8 Hz, 2H), 4.05-4.08 (m, 4H), 2.31 (s, 6H), 1.82-1.88 (m, 4H), 1.47-1.55 (m, 4H), 1.23-1.44 (m, 32H), 0.88-0.91 (m, 6H).

$^{13}$C NMR (100 MHz, CDCl$_3$):
159.6, 146.0, 127.6, 123.6, 123.5, 110.6, 68.3, 31.9, 29.7, 29.6, 29.6, 29.4, 29.3, 29.3, 26.1, 22.7, 16.4, 14.1.

MS (MALDI-TOF MS): m/z 579.511 (calc. [M+H]$^+$=579.489).

Example 25-3

DSC Measurement of Compound A4B9-C12

The thermal phase transition temperature of Compound A4B9-C12 was determined by differential scanning calorimetry.
Cr 54 Cr 83 Iso, Iso 62 Cr 51 Cr Example 25-4

Light Exposure Experiment for Compound A4B9-C12

The crystal-isotropic phase transition of Compound A4B9-C12 at 45° C. was observed using a polarizing optical microscope. The results are shown in FIG. 34.

Figure 34:
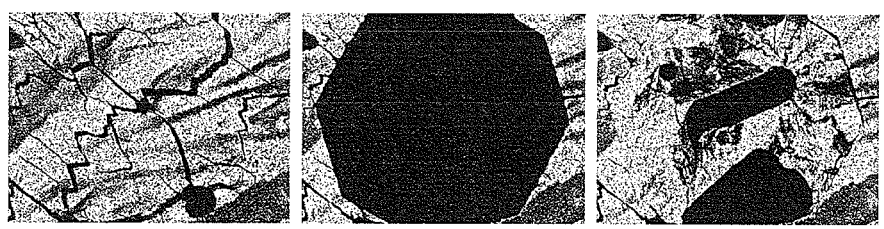
FIG. 34 represents a polarizing optical micrograph showing the crystal-isotropic phase transition of Compound A4B9-C12 at 45° C.

In FIG. 34, the left represents a polarizing optical micrograph before light exposure; the center represents a polarizing optical micrograph just after exposure to ultraviolet light (365 nm) for 270 seconds; and the right represents a polarizing optical micrograph after exposure to visible light (436 nm) for 3 seconds wherein the sample was exposed to ultraviolet light as stated above.

Application examples using the photosensitive azobenzene compounds according to the present invention are described below.

Example 26

Pattern Formation of Compound A1B7-C12 Using Photomask

A powdery sample of Compound A1B7-C12 was placed on a slide, and melted by heating at 70° C. A cover glass (22 mm×22 mm) was placed thereon to prepare a sandwich cell. The sandwich cell was cooled to room temperature to precipitate crystals. After placing a photomask on the cell, the cell was exposed to ultraviolet light (a high-pressure mercury lamp; 365 nm) from above at room temperature for 10 minutes. After the exposure, the photomask was removed. The cell was placed between two polarizers so that the polarization directions of the polarizers were adjusted to be orthogonal to each other, and then the sample was observed.

Figure 35:
FIG. 35 represents a photograph of the sandwich cell including Compound A1B7-C12 which was exposed to ultraviolet light (365 nm) through a photomask.

FIG. 35 shows a photograph of the sandwich cell including Compound A1B7-C12 which was exposed to ultraviolet light (365 nm) through the photomask, wherein the sandwich cell was placed between two polarizers so that the polarization directions thereof were orthogonal to each other.

The dark area is where Compound A1B7-C12 was in a liquid state, and the light yellow area is where Compound A1B7-C12 remained in a crystal state.

Specifically, light passed through Compound A1B7-C12 in a crystal state where Compound A1B7-C12 has birefringence (light yellow (bright) area). Contrary, light did not pass through Compound A1B7-C12 in a liquid state where Compound A1B7-C12 does not have birefringence (dark area). It is possible to form a bright/dark pattern by exposure to pattern light as illustrated in FIG. 35. A display or a recording device can be produced by utilizing this phenomenon.

Example 27

Pattern Formation of Compound A1B9-C12 Using Photomask

A powdery sample of Compound A1B9-C12 was placed on a slide, and melted by heating at 90° C. A cover glass (22 mm×22 mm) was placed thereon to prepare a sandwich cell. The sandwich cell was cooled to room temperature to precipitate crystals. After placing a photomask on the cell, the cell was exposed to ultraviolet light (a high-pressure mercury lamp; 365 nm) from above at room temperature for 10 minutes. After the exposure, the photomask was removed. The cell was placed between two polarizers so that the polarization directions of the polarizers were adjusted to be orthogonal to each other, and then the sample was observed.

Figure 36:
FIG. 36 represents a photograph of the sandwich cell including Compound A1B9-C12 which was exposed to ultraviolet light (365 nm) through a photomask.

FIG. 36 shows a photograph of the sandwich cell including Compound A1B9-C12 which was exposed to ultraviolet light (365 nm) through the photomask, wherein the sandwich cell was placed between two polarizers so that the polarization directions thereof were orthogonal to each other.

The dark area is where Compound A1B9-C12 was in a liquid state, and the light yellow area is where Compound A1B9-C12 remained in a crystal state.

Specifically, light passed through Compound A1B9-C12 in a crystal state where Compound A1B9-C12 has birefringence (light yellow (bright) area). Contrary, light did not pass through Compound A1B9-C12 in a liquid state where Compound A1B9-C12 does not have birefringence (dark area). It is possible to form a bright/dark pattern by exposure to pattern light as illustrated in FIG. 36. A display or a recording device can be produced by utilizing this phenomenon.

Example 28

Pattern Formation 1 of Compound A3B2-C12 Using Photomask

A powdery sample of Compound A3B2-C12 was placed on a slide, and melted by heating at 90° C. A cover glass (22 mm×22 mm) was placed thereon to prepare a sandwich cell.

The sandwich cell was cooled to room temperature to precipitate crystals. After placing a photomask on the cell, the cell was exposed to ultraviolet light (a high-pressure mercury lamp; 365 nm) from above at room temperature for 10 minutes. After the exposure, the photomask was removed. The cell was placed between two polarizers so that the polarization directions of the polarizers were adjusted to be orthogonal to each other, and then the sample was observed.

Figure 37:
FIG. 37 represents a photograph of the sandwich cell including Compound A3B2-C12 which was exposed to ultraviolet light (365 nm) through a photomask.

FIG. 37 shows a photograph of the sandwich cell including Compound A3B2-C12 which was exposed to ultraviolet light (365 nm) through the photomask, wherein the sandwich cell was placed between two polarizers so that the polarization directions thereof were orthogonal to each other.

The dark area is where Compound A3B2-C12 was in a liquid state, and the light yellow area is where Compound A3B2-C12 remained in a crystal state.

Specifically, light passed through Compound A3B2-C12 in a crystal state where Compound A3B2-C12 has birefringence (light yellow (bright) area). Contrary, light did not pass through Compound A3B2-C12 in a liquid state where Compound A3B2-C12 does not have birefringence (dark area). It is possible to form a bright/dark pattern by exposure to pattern light as illustrated in FIG. 37. A display or a recording device can be produced by utilizing this phenomenon.

Example 29

Pattern Formation 2 of Compound A3B2-C12 Using Photomask

A chloroform solution of Compound A3B2-C12 was spin-coated onto a cover glass (18 mm×18 mm) to form a crystalline thin film. After placing a photomask on the thin film, the thin film was exposed to ultraviolet light (a high-pressure mercury lamp; 365 nm) from above through the photomask at room temperature for 3 minutes. After the exposure, the photomask was removed. Nitrogen gas was blown against the surface of the thin film for 20 seconds using a nitrogen blower to remove the melted compound, and the sample was observed using an optical microscope.

Figure 38:
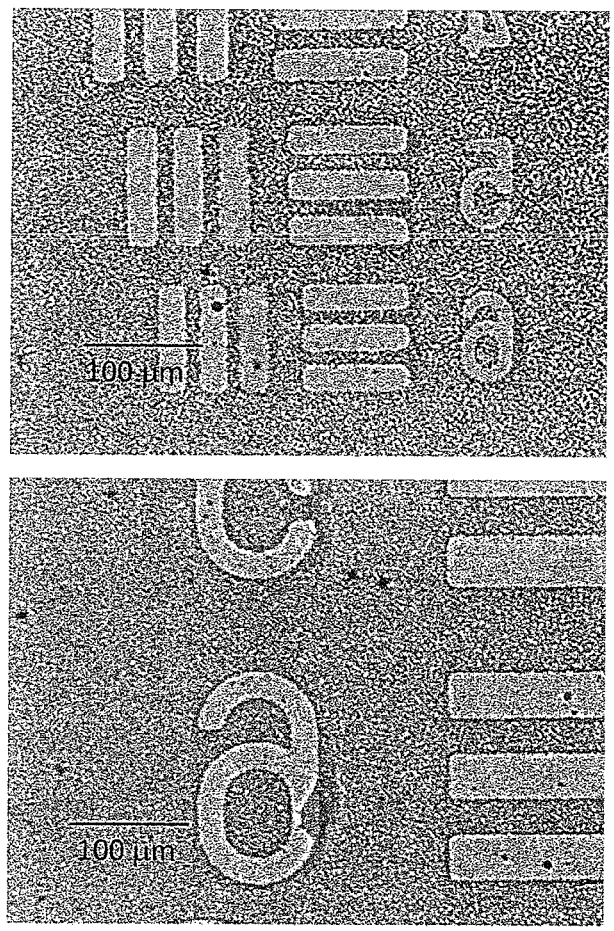
FIG. 38 represents an optical micrograph of the glass substrate on which a pattern was formed using a thin film of Compound A3B2-C12.

FIG. 38 shows an optical micrograph of the glass substrate on which a pattern was formed by the thin film of Compound A3B2-C12. As shown in FIG. 38, the area covered with the photomask remained in a crystal state, and the area where the compound changed into liquid was removed to form a pattern.

Example 30

Adhesion Test Using Compound A3B2-C12

Two quartz plates (13 mm×40 mm) were arranged so as to overlapped in part (13 mm). Compound A3B2-C12 was placed between the overlapping area, and pressed while being melted at 70° C. to bond the quartz plates. After cooling the sample to room temperature, a weight was suspended from one end, and the other end was raised to measure the weight at which adhesive failure occurred. Adhesive failure occurred at the weight of 1.8 kg.

A weight (5 g) was suspended from one end of substrates that were bonded in the same manner as described above, and the substrates were exposed to ultraviolet light (365 nm, 300 mW/cm²). Peeling occurred in 1 minute 15 seconds and one of the substrates fell.

The separated substrates by exposure to ultraviolet light were bonded again, and were exposed to visible light (465 nm) 3 minutes. As a result, adhesion was restored. When the weight was suspended from one end, and the other end was raised, adhesive failure occurred at the weight of 1.8 kg.

The above examples suggest that the adhesion of the compounds decreases by exposure to ultraviolet light, and is restored by exposure to visible light.

Figure 39:
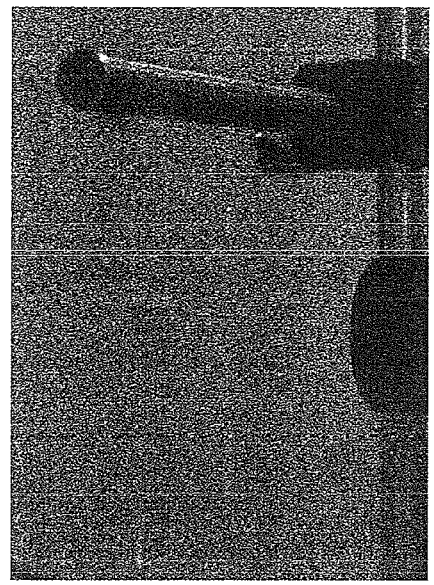
FIG. 39 represents a photograph of the adhesion test sample.

FIG. 39 shows a photograph of the adhesion test sample. Two quartz plates (13 mm×40 mm) were arranged so as to overlap in part (13 mm). Compound A3B2-C12 was placed between the overlapping area, and the adhesion test was performed. The adhesion test was performed on condition that the upper part of the sample was secured and that a weight was suspended from the lower part of the sample. The sample was exposed to light from the right side of the sample so that the entire bonding area was exposed.

Example 31

Pattern Formation of Compound A3B4-C12 Using Photomask

A crystalline thin film of Compound A3B4-C12 was formed on a glass substrate. A photomask with a 40 μm gap pattern was placed on the sample, and the sample was exposed to ultraviolet light (365 nm) at 65° C.

Figure 40:
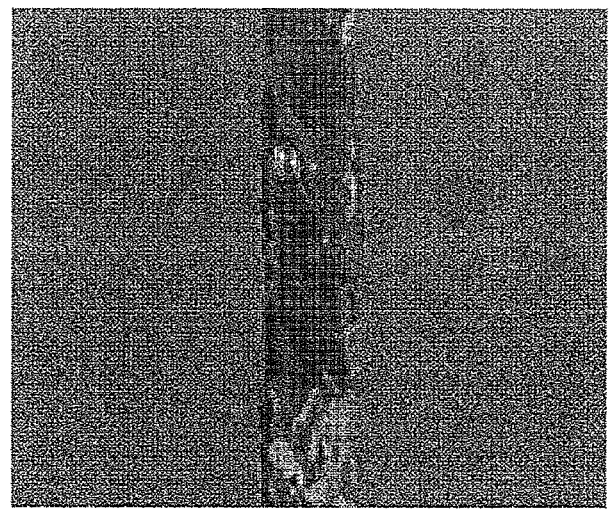
FIG. 40 represents an optical micrograph of a crystalline thin film of Compound A3B4-C12 in an area exposed to ultraviolet light.

FIG. 40 shows an optical micrograph of the area exposed to ultraviolet light. The area covered with the photomask remained in a crystal state to form a line with a width of 40 μm.

The invention claimed is:

1. An azobenzene derivative represented by the general formula (1),

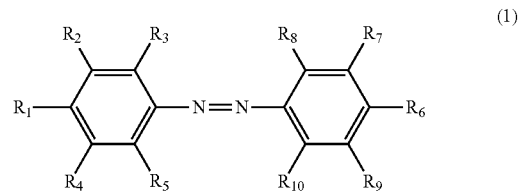

wherein $R_1$ and $R_6$ are independently an alkoxy group with 6 to 18 carbon atoms, and $R_2$ to $R_5$ and $R_7$ to $R_{10}$ are independently a hydrogen atom or an optionally branched alkyl group with 1 to 4 carbon atoms, with the proviso that the case where all of $R_2$ to $R_5$ and $R_7$ to $R_{10}$ are hydrogen atoms is excluded.

2. The photosensitive azobenzene derivative according to claim 1, wherein at least one of $R_2$, $R_4$, $R_7$, and $R_9$ is an optionally branched alkyl group with 1 to 4 carbon atoms.

3. The photosensitive azobenzene derivative according to claim 1, the photosensitive azobenzene derivative being capable of undergoing phase transition between a solid phase and a liquid phase by light exposure.

4. The azobenzene derivative according to claim 3, the azobenzene derivative undergoing phase transition from a solid phase to a liquid phase by exposure to ultraviolet light with a wavelength of 300 to 400 nm.

5. The azobenzene derivative according to claim 4, the azobenzene derivative undergoing reversible phase transition to the solid phase by exposure of the liquid phase to visible light with a wavelength of 400 to 700 nm.

6. An optical device comprising the azobenzene derivative according to claim 3.

7. A display device comprising the azobenzene derivative according to claim 3.

8. A recording device comprising the azobenzene derivative according to claim 3.

9. A pattern-forming material comprising the azobenzene derivative according to claim 3.

10. The photosensitive azobenzene derivative according to claim 1, the photosensitive azobenzene derivative changing in adhesion by light exposure.

11. The azobenzene derivative according to claim 9, wherein an adhesion thereof decreases by exposure to ultraviolet light with a wavelength of 300 to 400 nm and is restored by exposure to visible light with a wavelength of 400 to 700 nm.

12. An adhesive comprising the azobenzene derivative according to claim 10.

* * * * *